US009547794B2

United States Patent
Matsuzaki

(10) Patent No.: US 9,547,794 B2
(45) Date of Patent: Jan. 17, 2017

(54) IMAGE PROCESSING DEVICE, INFORMATION STORAGE DEVICE, AND IMAGE PROCESSING METHOD

(71) Applicant: OLYMPUS CORPORATION, Shibuya-ku, Tokyo (JP)

(72) Inventor: Hiroshi Matsuzaki, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/480,570

(22) Filed: Sep. 8, 2014

(65) Prior Publication Data

US 2014/0376792 A1 Dec. 25, 2014

Related U.S. Application Data

(63) Continuation of application No. PCT/JP2013/056273, filed on Mar. 7, 2013.

(30) Foreign Application Priority Data

Mar. 8, 2012 (JP) .................. 2012-051559
May 17, 2012 (JP) .................. 2012-113618

(51) Int. Cl.
*G06K 9/00* (2006.01)
*A61B 1/00* (2006.01)
(Continued)

(52) U.S. Cl.
CPC ....... *G06K 9/00765* (2013.01); *A61B 1/00009* (2013.01); *A61B 1/041* (2013.01); *G06K 9/00751* (2013.01); *G06K 9/6289* (2013.01)

(58) Field of Classification Search
CPC combination set(s) only.
See application file for complete search history.

(56) References Cited

U.S. PATENT DOCUMENTS 6,697,523 B1 *  2/2004  Divakaran ........ G06F 17/30802
                                                    382/173
7,110,454 B1 *  9/2006  Chakraborty .......... H04N 5/147
                                                    348/700
(Continued)

FOREIGN PATENT DOCUMENTS

CN        102096917 A      6/2011
JP        2006320650 A    11/2006
(Continued)

OTHER PUBLICATIONS

Extended European Search Report dated Dec. 1, 2015, issued in European Application No. 13778652.1.
(Continued)

*Primary Examiner* — Anand Bhatnagar
(74) *Attorney, Agent, or Firm* — Holtz, Holtz & Volek PC

(57) ABSTRACT

An image summarization device includes a first image summarization section that performs a first image summarization process based on a similarity between a plurality of images to acquire a first summary image sequence, a second image summarization section that performs a second image summarization process based on a target object/scene recognition process on each image among the plurality of images to acquire a second summary image sequence, and an integration processing section that performs an integration process on the first summary image sequence and the second summary image sequence, or performs an integration process on the first image summarization process and the second image summarization process to acquire an output summary image sequence.

20 Claims, 27 Drawing Sheets

(51) Int. Cl.
*A61B 1/04* (2006.01)
*G06K 9/62* (2006.01)

(56) References Cited

U.S. PATENT DOCUMENTS

| | | | |
|---|---|---|---|
| 7,120,873 B2* | 10/2006 | Li | G06F 17/30787 273/440.1 |
| 8,204,317 B2* | 6/2012 | Barbieri | G06F 17/30843 382/224 |
| 8,279,343 B2* | 10/2012 | Uemukai | G11B 27/034 348/461 |
| 8,606,083 B2* | 12/2013 | Girgensohn | G11B 27/034 386/278 |
| 8,655,036 B2* | 2/2014 | Valadez | A61B 6/03 128/922 |
| 8,869,198 B2* | 10/2014 | Riveiro Insua | H04N 21/8549 382/190 |
| 2004/0088723 A1* | 5/2004 | Ma | G06F 17/30787 725/19 |
| 2007/0124282 A1* | 5/2007 | Wittkotter | G06F 17/30858 |
| 2007/0171279 A1 | 7/2007 | Hasegawa et al. | |
| 2007/0195165 A1 | 8/2007 | Hirakawa | |
| 2008/0212881 A1 | 9/2008 | Hirakawa | |
| 2009/0041356 A1* | 2/2009 | Barbieri | G06K 9/00751 382/190 |
| 2009/0051695 A1 | 2/2009 | Matsuda | |
| 2009/0162025 A1* | 6/2009 | Girgensohn | G11B 27/034 386/241 |
| 2009/0245692 A1 | 10/2009 | Okutomi et al. | |
| 2010/0067808 A1 | 3/2010 | Matsuzaki | |
| 2010/0194992 A1 | 8/2010 | Kouno | |
| 2012/0207369 A1* | 8/2012 | Valadez | A61B 6/03 382/131 |
| 2012/0218394 A1 | 8/2012 | Yoshino et al. | |
| 2012/0281969 A1* | 11/2012 | Jiang | G11B 27/11 386/278 |
| 2014/0376817 A1 | 12/2014 | Yaguchi | |
| 2015/0030254 A1 | 1/2015 | Yaguchi | |

FOREIGN PATENT DOCUMENTS

| | | |
|---|---|---|
| JP | 2007195586 A | 8/2007 |
| JP | 2007257287 A | 10/2007 |
| JP | 2008146460 A | 6/2008 |
| JP | 2009005020 A | 1/2009 |
| JP | 2009050321 A | 3/2009 |
| JP | 2010069208 A | 4/2010 |
| JP | 2010158308 A | 7/2010 |
| JP | 2010183290 A | 8/2010 |
| JP | 2011024763 A | 2/2011 |
| JP | 2011104011 A | 6/2011 |
| JP | 2011175599 A | 9/2011 |
| JP | 2011200283 A | 10/2011 |

OTHER PUBLICATIONS

Bezerra, et al., "Low Cost Soccer Video Summaries Based on Visual Rhythm", Proceedings of the ACM International Multimedia Conference and Exhibition—MIR '06; Oct. 26-27, 2006; pp. 71-77; 3, 3.2 and 5.2.

Yun, et al., "Face Detection for video summary using illumination-compensation and morphological processing", Pattern Recognition Letters, Elsevier, Amersterdam, NL; vol. 30, No. 9, Jul. 1, 2009; pp. 856-860; 2, 3.2, 6, Figure 1.

Yun, et al., "Robust Face Detection for Video Summary Using Illumination-Compensation and Morphological Processing", Third International Conference on Natural Computation (ICNC 2007), Aug. 24, 2007; pp. 710-714; 2, 3.2 and 6.

International Search Report (ISR) dated Jun. 18, 2013 issued in International Application No. PCT/JP2013/056273.

Related U.S. Appl. No. 14/479,235, filed Sep. 5, 2014, Title: "Image Processing Device, Information Storage Device, and Image Processing Method", First Named Inventor: Yoichi Yaguchi.

U.S. Appl. No. 14/479,235, First Named Inventor: Yoichi Yaguchi, Title: "Image Processing Device, Information Storage Device, and Image Processing Method", filed Sep. 5, 2014.

U.S. Appl. No. 14/514,062, filed Oct. 14, 2014, First Named Inventor: Yoichi Yaguchi, Title: "Image Processing Device, Information Storage Device, and Image Processing Method".

Partial Supplementary European Search Report dated Mar. 1, 2016, issued in counterpart European Application No. 13758100.5.

Yanwei, et al., "Multi-View Video Summarization", IEEE Transactions on Multimedia, vol. 12, No. 7, Nov. 2010, pp. 717-729.

Li, et al., "Online redundant image elimination and its application to wireless capsule endoscopy", Signal, Image and Video Processing, 8.8 (2012), pp. 1497-1506.

Szczypiński, et al., "A model of deformable rings for interpretation of wireless capsule endoscopic videos", Medical Image Analysis, 13.2 (2009), pp. 312-324.

* cited by examiner

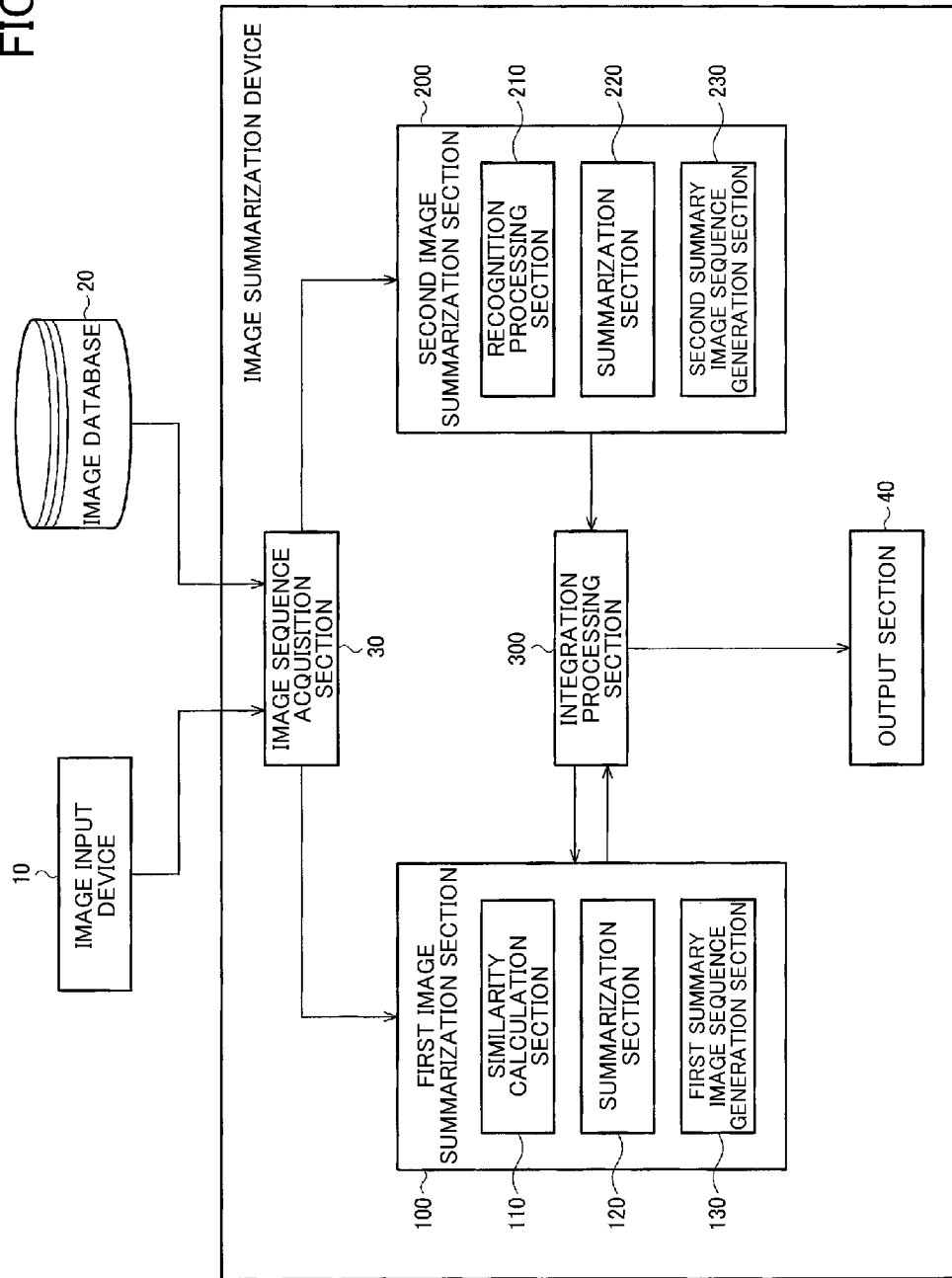

ALLOWED TO REMAIN IN SUMMARY IMAGE SEQUENCE    DELETED    SET TO BE PARTIAL IMAGE SEQUENCE

DETERMINATION TARGET IMAGE r

COVERAGE-
REQUIRING AREA

IMAGE PROCESSING DEVICE, INFORMATION STORAGE DEVICE, AND IMAGE PROCESSING METHOD

CROSS REFERENCE TO RELATED APPLICATION

This application is a continuation of International Patent Application No. PCT/JP2013/056273, having an international filing date of Mar. 7, 2013, which designated the United States, the entirety of which is incorporated herein by reference. Japanese Patent Application No. 2012-051559 filed on Mar. 8, 2012 and Japanese Patent Application No. 2012-113618 filed on May 17, 2012 are also incorporated herein by reference in their entirety.

BACKGROUND

The present invention relates to an image processing device, an information storage device, an image processing method, and the like.

When still images are continuously captured in time series at given time intervals, or when a spatial object is covered by a number of images, or when a movie is captured, and each image that forms the movie is used as a still image, for example, a very large number of temporally or spatially continuous images (hereinafter may be referred to as "image sequence") are acquired. In such a case, it is likely that the images that are closely situated in the image sequence (i.e., images that are close to each other temporally or spatially) are similar images, and it is not likely that it is necessary to check all of a large number of images in order to determine the captured information. Since the number of images may typically be tens of thousands or more, it takes time for the user to check all of the images.

Therefore, it has been desired to summarize the original image sequence using an image sequence that includes a smaller number of images by deleting images from the original image sequence. This process is hereinafter referred to as "image summarization process". For example, JP-A-2009-5020 discloses an image summarization method that extracts a scene change boundary image included in the image sequence, or an image that represents the image sequence, and allows images from which the information represented by the image sequence can be easily determined to remain.

For example, when applying the image summarization technique in the medical field, it is necessary to prevent a situation in which an area that cannot be observed occurs due to deletion of an image in order to prevent a situation in which a disease is missed. In particular, it is necessary to ensure that an important area such as a lesion area or an abnormal area can be reliably observed.

SUMMARY

According to one aspect of the invention, there is provided an image processing device comprising:

a first image summarization section that performs a first image summarization process based on a similarity between a plurality of images to acquire a first summary image sequence;

a second image summarization section that performs a second image summarization process based on a target object/scene recognition process on each image among the plurality of images to acquire a second summary image sequence; and an integration processing section that performs an integration process on the first summary image sequence and the second summary image sequence, or performs an integration process on the first image summarization process and the second image summarization process to acquire an output summary image sequence.

According to another aspect of the invention, there is provided an image processing device comprising:

an image sequence acquisition section that acquires an image sequence that includes a plurality of images; and a processing section that performs an image summarization process that acquires a summary image sequence based on a first deletion determination process and a second deletion determination process that delete some of the plurality of images included in the image sequence acquired by the image sequence acquisition section, the processing section setting an attention image sequence that includes one attention image or a plurality of attention images included in the plurality of images, selecting a first reference image from the attention image sequence, selecting a first determination target image from the plurality of images, and performing the first deletion determination process that determines whether or not the first determination target image can be deleted based on first deformation information that represents deformation between the first reference image and the first determination target image, the processing section setting a partial image sequence from the image sequence, a plurality of images that have been determined to be allowed to remain by the first deletion determination process being consecutively arranged in the partial image sequence, and the processing section selecting a second reference image and a second determination target image from the partial image sequence, and performing the second deletion determination process that determines whether or not the second determination target image can be deleted based on second deformation information that represents deformation between the second reference image and the second determination target image.

According to another aspect of the invention, there is provided a computer-readable storage device with an executable program stored thereon, wherein the program instructs a computer to function as:

a first image summarization section that performs a first image summarization process based on a similarity between a plurality of images to acquire a first summary image sequence;

a second image summarization section that performs a second image summarization process based on a target object/scene recognition process on each image among the plurality of images to acquire a second summary image sequence; and an integration processing section that performs an integration process on the first summary image sequence and the second summary image sequence, or performs an integration process on the first image summarization process and the second image summarization process to acquire an output summary image sequence.

According to another aspect of the invention, there is provided a computer-readable storage device with an executable program stored thereon, wherein the program instructs a computer to function as:

an image sequence acquisition section that acquires an image sequence that includes a plurality of images; and a processing section that performs an image summarization process that acquires a summary image sequence based on a first deletion determination process and a second deletion determination process that delete some of the plurality of images included in the image sequence acquired by the image sequence acquisition section, the processing section setting an attention image sequence that includes one attention image or a plurality of attention images included in the plurality of images, selecting a first reference image from the attention image sequence, selecting a first determination target image from the plurality of images, and performing the first deletion determination process that determines whether or not the first determination target image can be deleted based on first deformation information that represents deformation between the first reference image and the first determination target image, the processing section setting a partial image sequence from the image sequence, a plurality of images that have been determined to be allowed to remain by the first deletion determination process being consecutively arranged in the partial image sequence, and the processing section selecting a second reference image and a second determination target image from the partial image sequence, and performing the second deletion determination process that determines whether or not the second determination target image can be deleted based on second deformation information that represents deformation between the second reference image and the second determination target image.

According to another aspect of the invention, there is provided an image processing method that performs a first image summarization process based on a similarity between a plurality of images to acquire a first summary image sequence, and performs a second image summarization process based on a target object/scene recognition process on each image among the plurality of images to acquire a second summary image sequence, the image processing method comprising:

performing an integration process on the first summary image sequence and the second summary image sequence, or performing an integration process on the first image summarization process and the second image summarization process to acquire an output summary image sequence.

According to another aspect of the invention, there is provided an image processing method comprising:

acquiring an image sequence that includes a plurality of images;

setting an attention image sequence that includes one attention image or a plurality of attention images included in the plurality of images;

selecting a first reference image from the attention image sequence, and selecting a first determination target image from the plurality of images;

performing a first deletion determination process that determines whether or not the first determination target image can be deleted based on first deformation information that represents deformation between the first reference image and the first determination target image;

setting a partial image sequence from the image sequence, a plurality of images that have been determined to be allowed to remain by the first deletion determination process being consecutively arranged in the partial image sequence;

selecting a second reference image and a second determination target image from the partial image sequence;

performing a second deletion determination process that determines whether or not the second determination target image can be deleted based on second deformation information that represents deformation between the second reference image and the second determination target image; and performing an image summarization process that deletes some of the plurality of images included in the image sequence based on the first deletion determination process and the second deletion determination process to acquire a summary image sequence.

BRIEF DESCRIPTION OF THE DRAWINGS

FIG. 11 illustrates another system configuration example of an image summarization device according to one embodiment of the invention.

DESCRIPTION OF EXEMPLARY EMBODIMENTS

Figure 1:
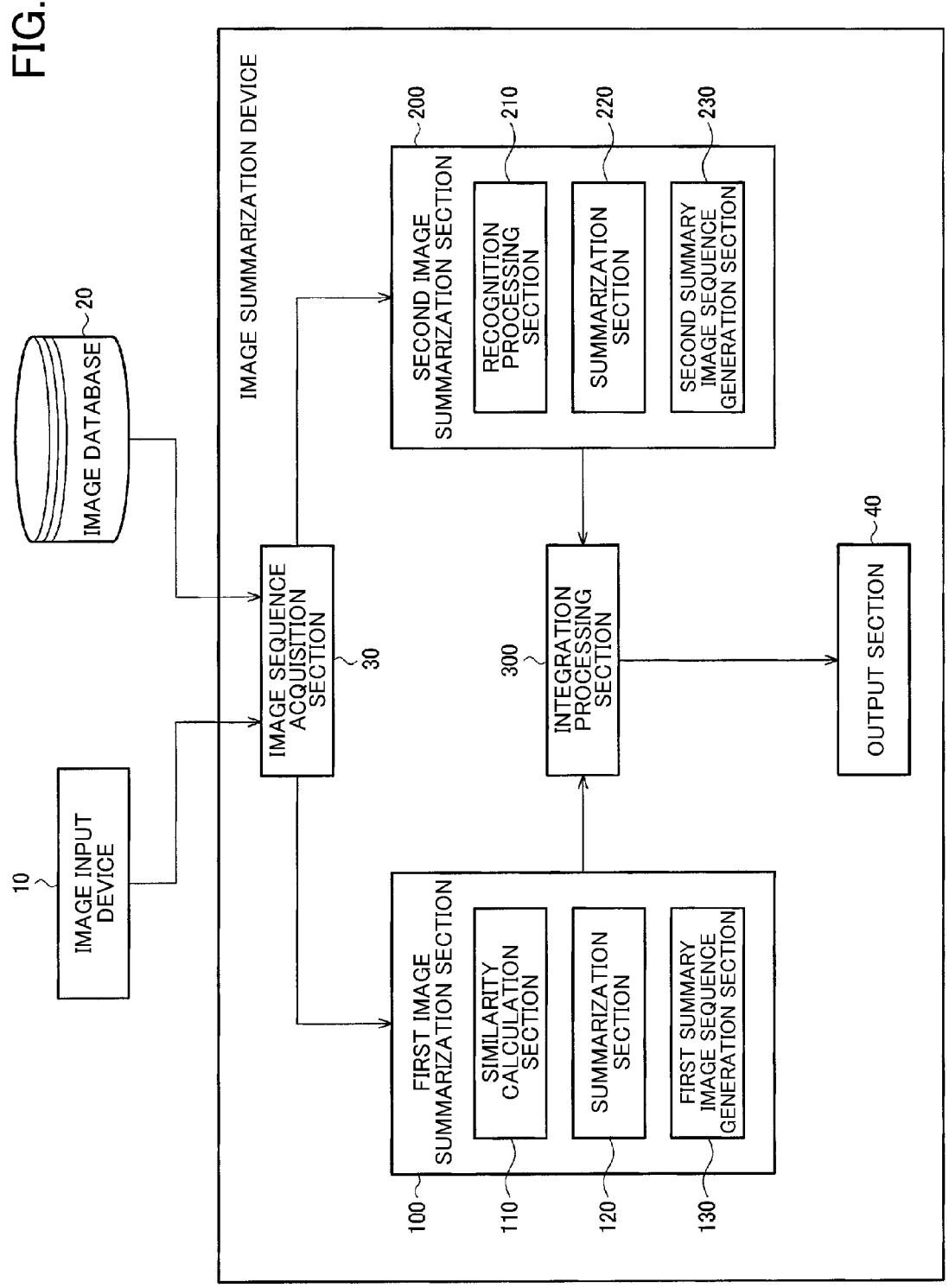
FIG. 1 illustrates a system configuration example of an image summarization device according to one embodiment of the invention.

According to one embodiment of the invention, there is provided an image processing device comprising:

a first image summarization section that performs a first image summarization process based on a similarity between a plurality of images to acquire a first summary image sequence;

a second image summarization section that performs a second image summarization process based on a target object/scene recognition process on each image among the plurality of images to acquire a second summary image sequence; and an integration processing section that performs an integration process on the first summary image sequence and the second summary image sequence, or performs an integration process on the first image summarization process and the second image summarization process to acquire an output summary image sequence.

According to one embodiment of the invention, the integration process is performed on the first image summarization process based on the similarity and the second image summarization process based on the target object/scene recognition process to acquire the output summary image sequence. This makes it possible to implement an image summarization process that achieves the advantages obtained when using the similarity and the advantages obtained when using the target object/scene recognition process. Therefore, it is possible to implement efficient image summarization, and improve convenience to the user, for example.

According to another embodiment of the invention, there is provided an image processing device comprising:

an image sequence acquisition section that acquires an image sequence that includes a plurality of images; and a processing section that performs an image summarization process that acquires a summary image sequence based on a first deletion determination process and a second deletion determination process that delete some of the plurality of images included in the image sequence acquired by the image sequence acquisition section, the processing section setting an attention image sequence that includes one attention image or a plurality of attention images included in the plurality of images, selecting a first reference image from the attention image sequence, selecting a first determination target image from the plurality of images, and performing the first deletion determination process that determines whether or not the first determination target image can be deleted based on first deformation information that represents deformation between the first reference image and the first determination target image, the processing section setting a partial image sequence from the image sequence, a plurality of images that have been determined to be allowed to remain by the first deletion determination process being consecutively arranged in the partial image sequence, and the processing section selecting a second reference image and a second determination target image from the partial image sequence, and performing the second deletion determination process that determines whether or not the second determination target image can be deleted based on second deformation information that represents deformation between the second reference image and the second determination target image.

According to this embodiment of the invention, the attention image sequence is set, the first deletion determination process is performed based on the attention image sequence, and the second deletion determination process is performed based on the results of the first deletion determination process. Since the first deletion determination process and the second deletion determination process are performed based on the deformation information about images, it is possible to implement an image summarization process that takes account of both the attention image and the deformation information. Since the process in the subsequent stage is performed using the results of the process in the preceding stage, the image summarization process can be effectively performed as compared with the case where each process is performed independently.

According to another embodiment of the invention, there is provided a computer-readable storage device with an executable program stored thereon, wherein the program instructs a computer to function as each section described above.

According to another embodiment of the invention, there is provided an image processing method that performs a first image summarization process based on a similarity between a plurality of images to acquire a first summary image sequence, and performs a second image summarization process based on a target object/scene recognition process on each image among the plurality of images to acquire a second summary image sequence, the image processing method comprising:

performing an integration process on the first summary image sequence and the second summary image sequence, or performing an integration process on the first image summarization process and the second image summarization process to acquire an output summary image sequence.

According to another embodiment of the invention, there is provided an image processing method comprising:

acquiring an image sequence that includes a plurality of images;

setting an attention image sequence that includes one attention image or a plurality of attention images included in the plurality of images;

selecting a first reference image from the attention image sequence, and selecting a first determination target image from the plurality of images;

performing a first deletion determination process that determines whether or not the first determination target image can be deleted based on first deformation information that represents deformation between the first reference image and the first determination target image;

setting a partial image sequence from the image sequence, a plurality of images that have been determined to be allowed to remain by the first deletion determination process being consecutively arranged in the partial image sequence;

selecting a second reference image and a second determination target image from the partial image sequence;

performing a second deletion determination process that determines whether or not the second determination target image can be deleted based on second deformation information that represents deformation between the second reference image and the second determination target image; and performing an image summarization process that deletes some of the plurality of images included in the image sequence based on the first deletion determination process and the second deletion determination process to acquire a summary image sequence.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Method

A method used in connection with several exemplary embodiments of the invention is described below. It is desirable to perform the image summarization process when an image sequence that includes a large number of temporally or spatially continuous images has been acquired, and the user performs a process (e.g., medical practice (e.g., diagnosis) when the image sequence is an endoscopic image sequence) using the image sequence. This is because the number of images included in the image sequence is very large, and it takes time for the user to check all of the images included in the image sequence to make a determination. Moreover, it is likely that similar images are included in the image sequence, and the amount of information that can be acquired is limited even if such similar images are thoroughly checked.

Specific examples of such an image sequence include an image sequence captured using a capsule endoscope. The capsule endoscope is a capsule-shaped endoscope that includes a small camera, and captures an image at given time intervals (e.g., twice a second). The capsule endoscope remains inside a body for several hours (tens or more hours in some cases) until it is discharged from the body, and several tens of thousands of captured images are acquired during a single examination. When the capsule endoscope moves inside a living body, the capsule endoscope may stop or move backward due to the motion of the living body, for example. Therefore, a large number of captured images may include a number of images that capture a similar object, and are not useful for finding a lesion or the like.

A known image summarization process may extract a scene change boundary image or an image that represents the image sequence. However, such a known image summarization process does not take account of the relationship between the object captured within the deletion target image and the object captured within the image that is allowed to remain when deleting an image. Therefore, the object that is captured within an image included in the image sequence that is not subjected to the image summarization process may not be captured within each image included in the image sequence obtained by the image summarization process.

This is particularly undesirable when applying the image summarization process in the medical field. This is because it is necessary to prevent a situation in which the attention area (e.g., lesion) is missed as much as possible. In order to prevent a situation in which the attention area is missed, it is desirable to capture a wide range inside a living body, and prevent a situation in which an object range that cannot be observed occurs due to deletion of a given image during the image summarization process.

Several aspects of the invention propose implementing an image summarization process from the viewpoint of preventing a situation in which an area that cannot be observed occurs due to deletion of an image. Specifically, the image summarization process is performed based on the similarity between a plurality of images included in an image sequence that is subjected to the image summarization process. It is possible to implement the image summarization process based on the relationship between a plurality of images by utilizing the similarity between the plurality of images.

The similarity may be calculated in various ways. For example, a reference image (i.e., an image that is allowed to remain (an image that may be allowed to remain depending on the reference image setting method)) and a determination target image (i.e., a deletion determination target image) may be selected from an image sequence, and the image summarization process may be performed based on deformation information about the reference image and the determination target image. Specifically, the reference image is deformed to calculate a coverage area within the determination target image (see FIG. 2). The object captured within the reference image corresponds to the object captured within the coverage area within the determination target image. Specifically, an area (hereinafter referred to as "non-coverage area") within the determination target image other than the coverage area cannot be covered by the reference image when the determination target image is deleted.

Therefore, the degree by which an object range that cannot be observed occurs is controlled by calculating the ratio of the coverage area with respect to the determination target image as the coverage ratio, and determining whether or not to delete the determination target image based on the calculated coverage ratio, for example. For example, the determination target image is deleted when the coverage ratio is equal to or larger than a threshold value, and is not deleted when the coverage ratio is less than the threshold value. In this case, the degree by which an area that cannot be observed occurs can be controlled corresponding to the threshold value.

As another example of the image summarization process that utilizes the deformation information, whether or not the determination target image can be deleted may be determined based on the results of a erosion process on the non-coverage area utilizing a structural element (corresponding to an attention area) (see FIGS. 23A to 23E). The details of the erosion process are described later. In this case, at least part of an area captured within the determination target image having a size equal to or larger than the size of the structural element is necessarily captured within the reference image even if the determination target image is deleted. Therefore, when the entire attention area is captured within the determination target image, at least part of the attention area can be observed within the reference image irrespective of the position of the attention area within the determination target image, and a situation in which the attention area is missed can be prevented.

Note that the similarity need not necessarily be calculated using the deformation information. The similarity between images may be calculated using another method.

However, since the image summarization process that utilizes the similarity is performed based on the relationship between the images, the object, the scene, or the like captured within the processing target image may not be taken into consideration. Therefore, when it is desired to capture a specific imaging target (e.g., the observation target of the doctor when using a capsule endoscope (a lesion or the like in a narrow sense)) within an image, it is useful to perform an image summarization process from the viewpoint of whether or not the imaging target is captured within an image in addition to the image summarization process based on the similarity.

Accordingly, several aspects of the invention propose a method that performs a first image summarization process based on the similarity, and a second image summarization process based on a target object/scene recognition process, and performs an integration process that acquire an output summary image sequence through integration. This makes it possible to implement an image summarization process that can achieve the advantages of the first image summarization process and the second image summarization process. Specifically, it is possible to implement an image summarization process that allows the user to efficiently observe the observation target object/scene while preventing a situation in which an object range that cannot be observed occurs.

Specific examples of the above method are described below in connection with first to fourth embodiments. The first embodiment illustrates an example in which a first summary image sequence is acquired by a first image summarization process, a second summary image sequence is acquired by a second image summarization process, and the first summary image sequence and the second summary image sequence are integrated by an integration process. The second embodiment illustrates an example in which the first summary image sequence and the second summary image sequence are acquired, the second summary image sequence is updated (i.e., the number of summary images included in the second summary image sequence is reduced (in a narrow sense)) based on the first summary image sequence, and the first summary image sequence and the updated second summary image sequence are integrated.

The third embodiment and the fourth embodiment illustrate an example in which the first image summarization process and the second image summarization process are integrated instead of integrating the first summary image sequence and the second summary image sequence. In the third embodiment, the first image summarization process is performed based on the results of the second image summarization process (second summary image sequence in a narrow sense). Specifically, the summary image included in the first summary image sequence is determined using the results of the second image summarization process in addition to the similarity instead of determining the summary image included in the first summary image sequence based on the similarity (see the first embodiment and the second embodiment).

The fourth embodiment illustrates an example in which a feedback process is performed by combining the method according to the third embodiment and the second summary image sequence update process according to the second embodiment. Specifically, the first image summarization process is performed based on the results of the second image summarization process to acquire the first summary image sequence. The second summary image sequence update process is performed based on the acquired first summary image sequence. The first image summarization process is then performed based on the updated second summary image sequence to acquire the first summary image sequence, and the acquired first summary image sequence is set to be the output summary image sequence. When the update process could not be performed, the first summary image sequence that has been acquired is set to be the output summary image sequence (see the third embodiment).

Note that an image sequence obtained by the first image summarization process based on the similarity is referred to as "first summary image sequence", and each image included in the first summary image sequence is referred to as "similarity summary image". An image sequence obtained by the second image summarization process based on the target object/scene recognition process is referred to as "second summary image sequence", and each image included in the second summary image sequence is referred to as "object summary image". An image sequence that is finally output based on the process including the integration process and the like is referred to as "output summary image sequence", and each image included in the output summary image sequence is referred to as "output summary image".

When the process that utilizes the deformation information as the similarity is performed, and the attention area detection process is used as the recognition process, a method other than the methods according to the first to fourth embodiments may also be employed. The deletion determination process that utilizes only the coverage ratio does not take account of whether or not the attention image (i.e., an image in which the attention area is captured) can be deleted in the same manner as the process that utilizes only the similarity. For example, when the coverage ratio of the attention image by another image (e.g., another attention image or an image other than the attention image) is high, it is determined that the attention image can be deleted. Therefore, all of the attention images may be deleted from the image sequence, and it may be impossible to observe the attention area from the summary image sequence obtained by the image summarization process.

When using the deletion determination process that utilizes the structural element, an image in which the entire attention area is captured may be deleted, and an image in which only part of the attention area is captured may be allowed to remain. Such a situation is undesirable from the viewpoint of observation of the attention area.

It may be possible to perform an effective image summarization process can be performed using the process that utilizes the deformation information (e.g., the process that utilizes the coverage ratio and/or the structural element). However, when it is desired to mainly observe a specific attention area (e.g., a lesion when using a capsule endoscope), it is useful to perform the process from the viewpoint of whether or not the attention area is captured. Specifically, it is possible to deal with the problem that may occur when performing the process that utilizes the deformation information by allowing the attention image to (necessarily in a narrow sense) remain in the summary image sequence.

Figure 16A:
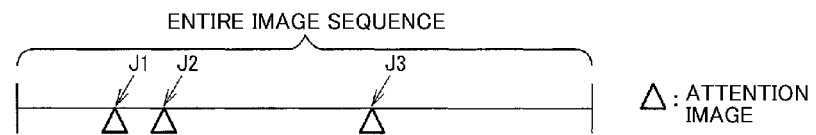
FIGS. 16A to 16D are views illustrating an image summarization process according to one embodiment of the invention.
Figure 16B:

Therefore, several aspects of the invention propose a method that sets one image or a plurality of images included in the acquired image sequence in which the attention area is captured to be an attention image sequence, and performs the image deletion determination process that utilizes the deformation information based on the attention image sequence to acquire the summary image sequence. However, when the attention image sequence is calculated as illustrated to FIG. 16A, and the image sequence is independently calculated by performing the image summarization process based on the deformation information, the images may be closely situated (see I1 in FIG. 16B) if the sum-set is merely calculated. In this case, an image that is sufficiently covered by another image may be allowed to remain in the summary image sequence, and the effect of reducing the number of images through the image summarization process may decrease. Therefore, the effect of reducing the number of images through the image summarization process is improved by performing a first deletion determination process based on the attention image sequence, and performing a second deletion determination process based on the results of the first deletion determination process (two-step process). The first deletion determination process and the second deletion determination process utilize the deformation information, and the details thereof are described later.

Figure 30:
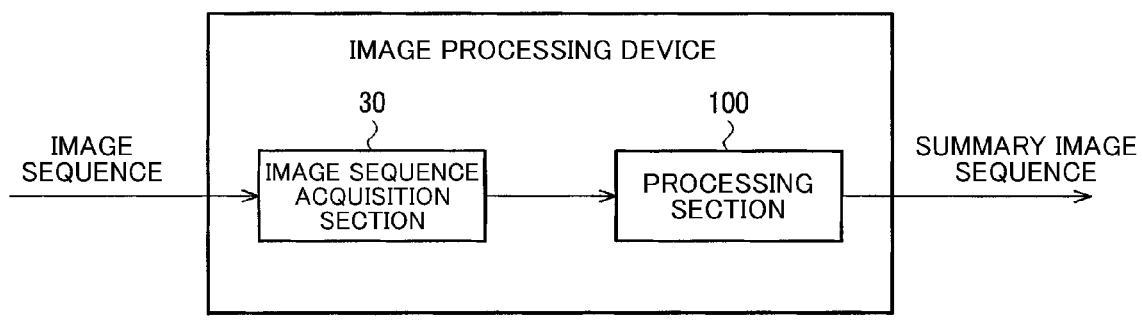
FIG. 30 illustrates a basic system configuration example of an image processing device.

An image processing device according to one embodiment of the invention may include a processing section 100 and an image sequence acquisition section 30 (see FIG. 30). The image sequence acquisition section 30 acquires an image sequence that includes a plurality of images. The processing section 100 sets an attention image sequence that includes one attention image or a plurality of attention images included in the plurality of images, selects a first reference image from the attention image sequence, selects a first determination target image from the plurality of images, and performs a first deletion determination process that determines whether or not the first determination target image can be deleted based on first deformation information that represents deformation between the first reference image and the first determination target image. The processing section 100 sets a partial image sequence from the image sequence, a plurality of images that have been determined to be allowed, to remain by the first deletion determination process being consecutively arranged in the partial image sequence. The processing section 100 selects a second reference image and a second determination target image from the partial image sequence, and performs a second deletion determination process that determines whether or not the second determination target image can be deleted based on second deformation information that represents deformation between the second reference image and the second determination target image.

A fifth embodiment illustrates a basic method. In the fifth embodiment, the first deletion determination process and the second deletion determination process are performed based on the coverage ratio. Note that the first deletion determination process and the second deletion determination process may be implemented in various ways (e.g., the structural element may be used). Such a modification will be described in connection with a sixth embodiment. The reference image (second reference image) and the determination target image (second determination target image) used for the second deletion determination process may also be selected in various ways. Such a modification will be described in connection with a seventh embodiment.

2. First Embodiment

The method according to the first embodiment is described below. A system configuration example of an image summarization device will be described first, and specific examples of the first image summarization process and the second image summarization process will then be described. The integration process will be described thereafter.

2.1 System Configuration Example

FIG. 1 illustrates a configuration example of the image summarization device according to the first embodiment. As illustrated in FIG. 1, the image summarization device includes an image sequence acquisition section 30, a first image summarization section 100, a second image summarization section 200, an integration processing section 300, and an output section 40. Note that the configuration of the image summarization device is not limited to the configuration illustrated in FIG. 1. Various modifications may be made, such as omitting some (e.g., output section 40) of the elements illustrated in FIG. 1, or adding other elements.

The image sequence acquisition section 30 acquires image sequence data that is subjected to the image summarization process. The image sequence acquisition section 30 acquires a plurality of temporally or spatially continuous images as the image sequence data. The image sequence acquisition section 30 acquires the image sequence data from an image input device 10, an image database 20, or the like. The image input device 10 may be an imaging device that captures an image (e.g., digital camera or capsule endoscope). The image database 20 is a database that stores a large number of images. The image database 20 stores image data acquired by an imaging device or the like. Note that the image database 20 may be provided at position remote from the image summarization device. For example, the image database 20 may be implemented by a server or the like that is connected to the image summarization device through a network. The image input device 10 and the image database 20 are normally provided separately from the image summarization device. Note that the image input device 10 and the image database 20 may be included in the image summarization device.

The first image summarization section 100 performs the first image summarization process based on the similarity. The first image summarization section 100 may include a similarity calculation section 110, a summarization section 120, and a first summary image sequence generation section 130. Note that the configuration of the first image summarization section 100 is not limited to the configuration illustrated in FIG. 1. Various modifications may be made, such as omitting some of the elements illustrated in FIG. 1, or adding other elements.

The similarity calculation section 110 calculates the similarity between images among the images included in the image sequence acquired by the image sequence acquisition section 30. The summarization section 120 performs a summarization process (i.e., a process that determines a similarity summary image that is allowed to remain in the first summary image sequence, and a deletion target image) based on the calculated similarity. The first summary image sequence generation section 130 generates the first summary image sequence that is output from the first image summarization section 100 based on the summarization process performed by the summarization section 120. Note that the details of the first image summarization process are described later.

The second image summarization section 200 performs the second image summarization process based on the target object/scene recognition process. The second image summarization section 200 may include a recognition processing section 210, a summarization section 220, and a second summary image sequence generation section 230. Note that the configuration of the second image summarization section 200 is not limited to the configuration illustrated in FIG. 1. Various modifications may be made, such as omitting some of the elements illustrated in FIG. 1, or adding other elements.

The recognition processing section 210 performs a recognition process that determines whether or not the image included in the image sequence acquired by the image sequence acquisition section 30 includes the target object, or determines whether or not the image included in the image sequence acquired by the image sequence acquisition section 30 captures the target scene. The recognition process may be implemented in various ways. For example, a template that represents the target object or the target scene may be stored, and a matching process that utilizes the template may be performed. The summarization section 220 performs a summarization process (i.e., a process that determines an object summary image that is allowed to remain in the second summary image sequence, and a deletion target image) based on the recognition results of the recognition processing section 210. Specifically, the summarization section 220 performs a segmentation process taking account of an area in which an identical target object or an identical scene is continuously captured, and selects at least one image from the generated segment (consecutive image sequence) as the object summary image. The second summary image sequence generation section 230 generates the second summary image sequence that is output from the second image summarization section 200 based on the summarization process performed by the summarization section 220. Note that the details of the second image summarization process are described later.

The integration processing section 300 performs the integration process based on the process performed by the first image summarization section 100 and the process performed by the second image summarization section 200. In the first embodiment, the integration processing section 300 performs the integration process on the first summary image sequence and the second summary image sequence. The details thereof are described later.

The output section 40 outputs the output summary image sequence acquired as the results of the integration process performed by the integration processing section 300. The output section 40 may be a display section that is implemented by a liquid crystal display, an organic EL display, or the like. In this case, the output section 40 may display the output summary image included in the output summary image sequence, for example. Note that the image summarization device need not necessarily include a display section or the like that serves as an interface with the user. The output section 40 (display section) may be provided separately from the image summarization device.

2.2 First Image Summarization Process

The first image summarization process based on the similarity is described below. The similarity may be the motion vector between images, the SSD, the SAD, a correlation value (e.g., normalized cross-correlation), or the like. Arbitrary information may be used as the similarity as long as the information is normally calculated as the similarity between a plurality of images.

The image summarization process based on the similarity may be implemented using a known method that detects a scene change by performing a sorting process in ascending order of the similarity, and performing a selection process up to the set number.

Figure 2:
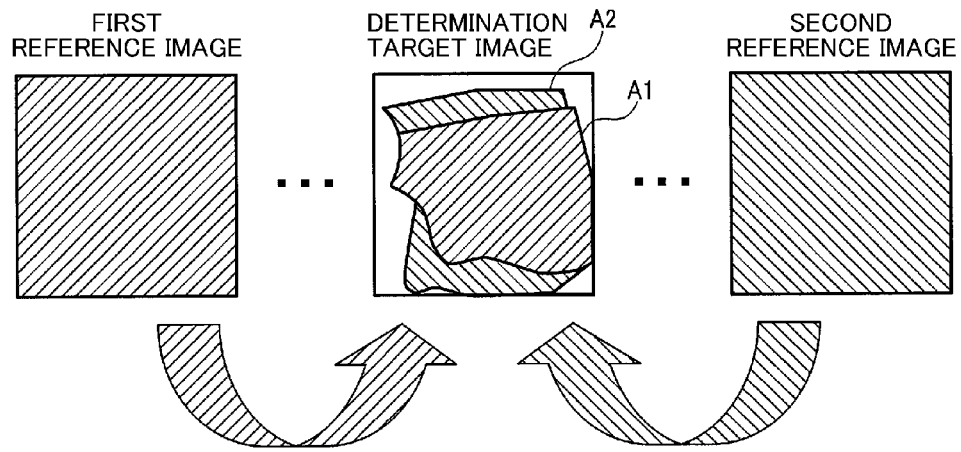
FIG. 2 is a view illustrating a coverage ratio calculation method.

As illustrated in FIG. 2, the coverage ratio of the determination target image by the reference image (i.e., the similarity summary image that is allowed to remain in the first summary image sequence, or a candidate image for the similarity summary image) may be used as the similarity, and whether or not the determination target image can be deleted may be determined based on the coverage ratio to implement the image summarization process. The method that utilizes the coverage ratio is described in detail below.

The method that utilizes the coverage ratio deforms the reference image using the deformation information about the reference image and the determination target image, and projects the reference image onto the determination target image. The deformation information refers to information that represents a state in which the object captured within the reference image is deformed within the determination target image. The deformation information may be calculated from deformation estimation, the motion vector, or the like, or a non-rigid deformation parameter estimated by the method disclosed in JP-A-2011-24763 may be used as the deformation information, for example.

FIG. 2 illustrates an example in which a first reference image that precedes the determination target image, and a second reference image that follows the determination target image are set to be the reference image. An area within the determination target image that is indicated by A1 is an area obtained by deforming the first reference image, and an area within the determination target image that is indicated by A2 is an area obtained by deforming the second reference image. In this case, an area that corresponds to the sum-set of the area indicated by A1 and the area indicated by A2 may be calculated as the coverage area, and the ratio of the coverage area to the entire determination target image may be used as the coverage ratio, for example.

Whether or not the determination target image can be deleted may be determined by comparing the coverage ratio with a threshold value that is set in advance. Note that the threshold value may be set by the system, or may be determined based on an input performed by the user. Specifically, when the coverage ratio is less than the threshold value, it is determined that the determination target image cannot be deleted. When the coverage ratio is equal to or more than the threshold value, it is determined that the determination target image can be deleted. When the coverage ratio is equal to or more than the threshold value, an area of the object range captured within the determination target image that is represented by the threshold value is captured within at least one of the first reference image and the second reference image. Therefore, when the first reference image and the second reference image are allowed to remain as the similarity summary image, the area captured within the determination target image is sufficiently covered even when the determination target image is deleted.

Figure 3A:
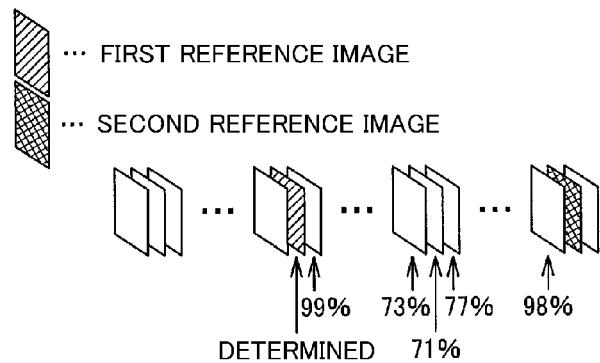
FIGS. 3A and 3B are views illustrating a specific example of a first image summarization process.
Figure 3B:
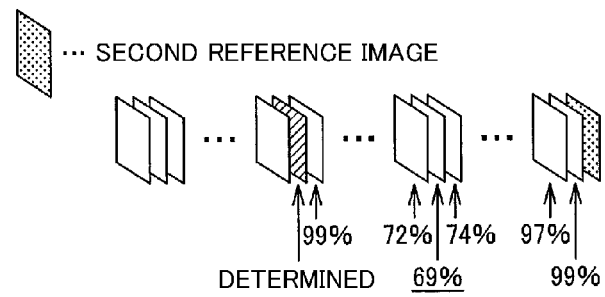

FIGS. 3A and 3B illustrate the process that selects the first reference image, the second reference image, and the determination target image. Note that it has been determined that the first reference image is selected as the similarity summary image. On the other hand, the second reference image is a candidate for the similarity summary image, and it has not been determined that the second reference image is selected as the similarity summary image.

In FIG. 3A, the kth image of the image sequence is selected as the first reference image. The first to (k−1)th images have been determined to be selected as the similarity summary image, or deleted, and the kth to Nth mages are the processing target. In this case, the (k+2)th image is selected as the second reference image.

The determination target image is sequentially selected from the first image among the images situated between the first reference image and the second reference image. The first reference image is deformed based on the deformation information about the first reference image and the determination target image, and the second reference image is deformed based on the deformation information about the second reference image and the determination target image to calculate the coverage ratio. Whether or not the determination target image can be deleted is determined based on the calculated coverage ratio.

When it has been determined that all of the images situated between the first reference image and the second reference image can be deleted (see FIG. 3A) (threshold value=70%) (i.e., the image that follows the current second reference image can be selected as the second reference image), the next second reference image is selected as illustrated in FIG. 3B. Specifically, the (k+3)th image is selected as the next second reference image.

Whether or not the images situated between the first reference image and the second reference image can be deleted is then determined. When it has been determined that the determination target image cannot be deleted (see FIG. 3B) (i.e., all of the images situated between the first reference image and the current second reference image are not covered by the first reference image and the current second reference image) (i.e., the determination target image that cannot be deleted is not covered by the first reference image and the current second reference image), it is considered that the update of the second reference image (increment in the selection position) was inappropriate (i.e., the interval between the first reference image and the second reference image was increased to a large extent).

Therefore, the image that immediately precedes the current second reference image (corresponding to the second reference image in FIG. 3A) is allowed to remain as the similarity summary image. Specifically, the image that immediately precedes the current second reference image is selected as the next first reference image, and the second reference image and the determination target image are selected to continue the process.

Figure 4:
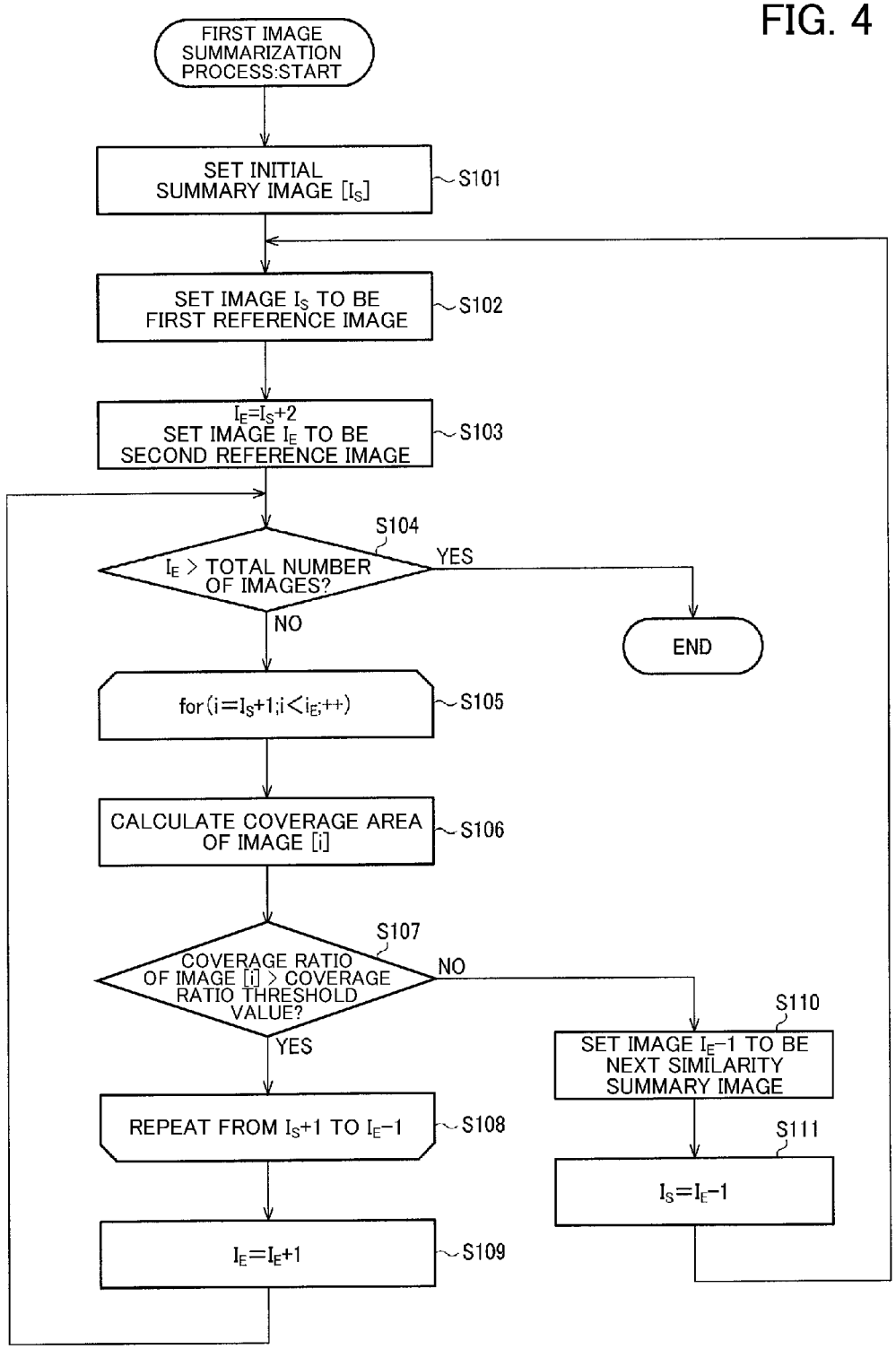
FIG. 4 is a flowchart illustrating a first image summarization process.

FIG. 4 is a flowchart illustrating the first image summarization process when using the coverage ratio as the similarity. When the first image summarization process has started, the $I_S$th image of the image sequence that is subjected to the image summarization process is set to be the first similarity summary image (S101). The value $I_S$ may be 1 (i.e., the first image of the image sequence may be set to be the similarity summary image), or may be a value other than 1.

The $I_S$th image is set to be the first reference image (S102), and the $I_E$th images is set to be the second reference image (S103). The initial value of the value $I_E$ is a value that satisfies $I_E=I_{S+}2$.

Whether or not the value $I_E$ is larger than the number of images included in the processing target image sequence is determined (S104). When it has been determined that the value $I_E$ is larger than the number of images included in the processing target image sequence, the image summarization process is terminated. When it has been determined that the value $I_E$ is not larger than the number of images included in the processing target image sequence (i.e., the second reference image could be appropriately set), the images situated between the first reference image and the second reference image are sequentially set to be the determination target image, and whether or not the determination target image can be deleted is determined. Specifically, the image that immediately follows the first reference image is set to be the first determination target image, and the coverage ratio is calculated using the method illustrated in FIG. 2, and compared with the threshold value (S106 and S107). When the coverage ratio is equal to or more than the threshold value (Yes in S107) (i.e., the determination target image can be deleted), the image that immediately follows the current determination target image is set to be the determination target image (i.e., the value i is incremented in FIG. 4). When it has been determined that the coverage ratio is equal to or more than the threshold value (Yes in S107), and the loop process in the steps S105 to S108 has ended (i.e., all of the images situated between the first reference image and the second reference image can be covered by the first reference image and the second reference image) (see FIG. 3A), the value $I_E$ is incremented to update the second reference image (S109), and the step S104 is performed.

When it has been determined that the coverage ratio is less than the threshold value (No in S107) (i.e., at least one image among the images situated between the first reference image and the second reference image cannot be sufficiently covered by the first reference image and the second reference image) (see FIG. 3B), it is necessary to allow the image that immediately precedes the current second reference image to remain as the summary image. Therefore, the $(I_E-1)$th image is set to be the next similarity summary image (S110). The value $I_S$ is set to $I_E-1$ (S111), the image set to be the similarity summary image is set to be the next first reference image (S102), and the process is performed again.

2.3 Second Image Summarization Process

The second image summarization process based on the target object/scene recognition process is described below. The recognition process may utilize the processing results of various image recognition/image detection processes (e.g., the processing results of a detection process based on the similarity with the reference image, or the recognition results obtained by a pattern recognition process using machine learning).

In the second image summarization process, the recognition process is performed on each image of the image sequence that is subjected to the image summarization process to determine whether or not the target object is captured within each image, or determine whether or not the target scene is captured within each image. Consecutive images among the images in which the target object is captured, or consecutive images among the images in which the target scene is captured, are set to be the consecutive image sequence (segment). At least one image is extracted from each segment, and set to be the object summary image that is allowed to remain in the second summary image sequence.

Figure 5:
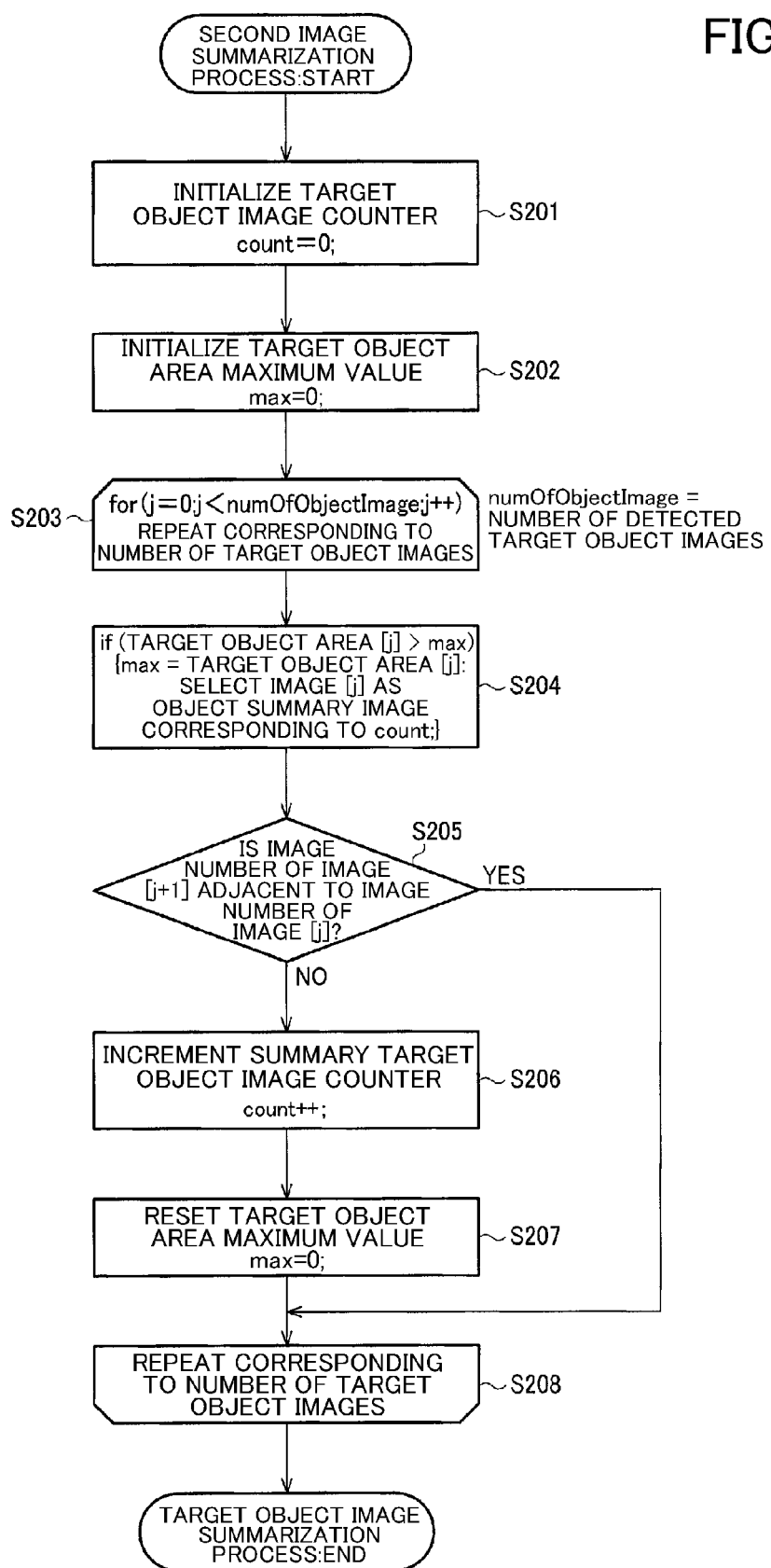
FIG. 5 is a flowchart illustrating a second image summarization process.

FIG. 5 is a flowchart illustrating the second image summarization process based on the target object/scene recognition process. Although an example in which an image in which the recognized target object has the maximum area is selected as the object summary image is described below, the method that selects the object summary image from the consecutive image sequence is not limited thereto.

Figure 6:
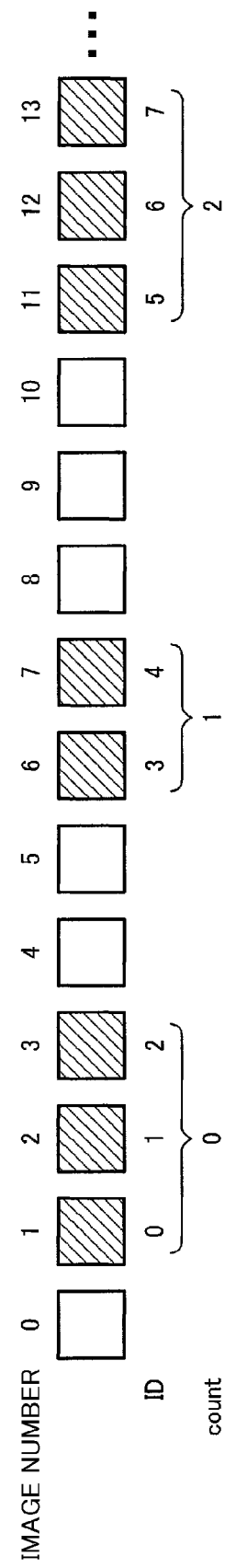
FIG. 6 is a view illustrating a second image summarization process.

Note that the recognition process has been performed before the process illustrated in FIG. 5 is performed. An ID is sequentially assigned to the images in which the target object or the like has been detected. The ID is linked to a number that represents the position of the image in the image sequence (input image sequence) that is subjected to the image summarization process. In FIG. 6, the target object or the like has been detected within the images indicated by the diagonal lines by the recognition process performed on the input image sequence, and an ID is sequentially assigned from the first image among the images indicated by the diagonal lines, for example. Note that the image number and the ID need not necessarily start from 0. Since the position of each image (to which the ID is assigned) in the input image sequence can be determined, information is stored that indicates that the image to which the ID=0 is assigned is the first image of the input image sequence image, and the image to which the ID=4 is assigned is the seventh image of the input image sequence image. FIG. 5 illustrates the subsequent segmentation process and representative image (summary image) selection process.

When the second image summarization process has started, a counter value count is initialized (S201). The counter value count corresponds to the number of object summary images. When one summary image is selected from one segment, the counter value count also corresponds to the segment that is set as a result of the segmentation process. A variable max that represents the maximum area of the target object is initialized (S202).

After initialization, a loop process (S203 to S208) is repeated to sequentially process the images to which the ID is assigned. Specifically, the initial value is set to J=0, and the area of the target object within the image to which the ID=j is assigned is compared with the variable max. When the area of the target object is larger than the variable max, the variable max is overwritten with the area of the target object, and the image to which the ID=j is assigned is set to be the summary image corresponding to the counter value count (S204). Since it is desirable to designate the summary image using the number in the input image sequence instead of using the ID value, information is stored that indicates the image of the input image sequence that corresponds to the summary image corresponding to the counter value count based on the relationship between the image number in the input image sequence and the ID.

Whether or not the image to which the ID=j is assigned is situated adjacent to the image of the input image sequence to which the ID=j+1 is assigned is determined (S205). It is determined that the image to which the ID=j is assigned is not situated adjacent to the image to which the ID=j+1 is assigned (No in S205) when the processing target is the last image of the segment (e.g., ID=2 or ID=4 in FIG. 6). Therefore, the process on the current segment is terminated, the counter value count is incremented (S206), and the variable max is initialized (S207) (i.e., a preliminary process on the next segment).

It is determined that the image to which the ID=j is assigned is situated adjacent to the image to which the ID=j+1 is assigned (Yes in S205) when the processing target is the first image or the intermediate image of the segment (e.g., ID=1 or ID=3 in FIG. 6). In this case, the steps S206 and S207 are not performed. When the processing target is the first image of the segment (max=0), the current image is selected in the step S204 as a provisional object summary image. When the processing target is the intermediate image of the segment, a given image that is included in the current segment and precedes the processing target is provisionally selected as the object summary image corresponding to the counter value count, and the area of the target object is stored as the variable max. Therefore, the area of the target object within the provisional object summary image is compared in the step S204 with the area of the target object within the image to which the ID=j is assigned. When the area of the target object within the image to which the ID=j is assigned is larger than the area of the target object within the provisional object summary image, the object summary image corresponding to the counter value count is overwritten with the image to which the ID=j is assigned. When the area of the target object within the provisional object summary image is larger than the area of the target object within the image to which the ID=j is assigned, the object summary image is maintained.

Specifically, the loop process (S203 to S208) performs the segmentation process, and selects the image of each segment in which the target object has the maximum area as the object summary image. When the above process has been performed on each image in which the target object has been detected, the process is terminated.

Although an example in which the image in which the target object has the maximum area is selected as the object summary image has been described above, the image summarization process may be similarly performed utilizing information about the results of the image recognition process or the image detection process (e.g., the position of the target object within the image, color information, texture information, or recognition/detection accuracy).

2.4 Integration Process

The integration process according to the first embodiment is described below. The integration process selects an image that is included in at least one of the first summary image sequence obtained by the first image summarization process and the second summary image sequence obtained by the second image summarization process as the output summary image of the output summary image sequence.

Figure 7:
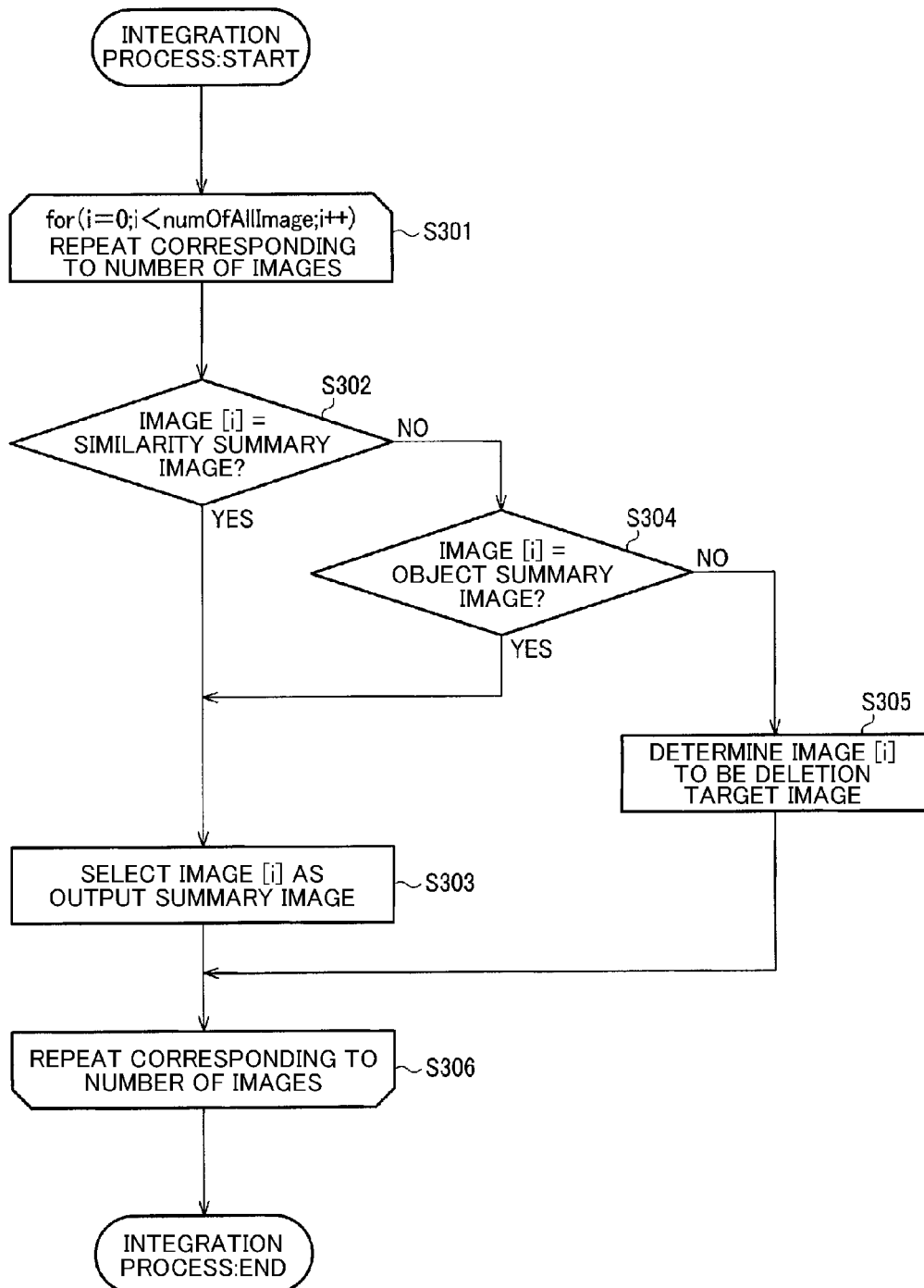
FIG. 7 is a flowchart illustrating an integration process according to a first embodiment.

FIG. 7 is a flowchart illustrating the integration process according to the first embodiment. As illustrated in FIG. 7, a loop process (S301 to S306) is performed during the integration process. The steps S302 to S305 are performed on all of the images of the input image sequence.

Specifically, whether or not the ith image of the input image sequence is included in the first summary image sequence (i.e., whether or not the ith image is the similarity summary image) is determined (S302). When the ith image is included in the first summary image sequence (Yes in S302), the ith image is selected as the output summary image of the output summary image sequence (S303). When the ith image is not included in the first summary image sequence (No in S302), whether or not the ith image is included in the second summary image sequence (i.e., whether or not the ith image is the object summary image) is determined (S304). When the ith image is included in the second summary image sequence (Yes in S304), the ith image is selected as the output summary image (S303). When the ith image is not included in the second summary image sequence (No in S304), the ith image is determined to be the deletion target image (S305). The above process is performed on the entire input image sequence while incrementing the value i (initial value: i=0).

According to the first embodiment, the image summarization device includes the first image summarization section 100 that performs the first image summarization process based on the similarity between a plurality of images to acquire the first summary image sequence, the second image summarization section 200 that performs the second image summarization process based on the target object/scene recognition process on each image among the plurality of images to acquire the second summary image sequence, and the integration processing section 300 that performs the integration process on the first summary image sequence and the second summary image sequence, or performs the integration process on the first image summarization process and the second image summarization process to acquire the output summary image sequence (see FIG. 1).

The plurality of images normally correspond to the entire image sequence acquired by the image sequence acquisition section 30. Note that the plurality of images may be part of the image sequence acquired by the image sequence acquisition section 30.

According to this configuration, since the summary image sequence obtained by the image summarization process based on the determination as to the similarity between the images, and the summary image sequence obtained by the image summarization process based on the target object/scene recognition process, can be integrated to acquire the output summary image sequence, it is possible to implement an image summarization process that achieves the advantages of each image summarization process. A summary image sequence that includes an appropriate image in which an important target object is captured can be generated by performing the second image summarization process that utilizes the target object/scene recognition process. However, it is difficult to detect all of the important target objects using the image recognition/detection process. It is possible to cause an important object that cannot be detected to be included in the first summary image sequence acquired by the first image summarization process by preventing a situation in which an area that cannot be observed occurs through the image summarization process based on the similarity (i.e., a different viewpoint), and generate a complementary output summary image sequence via the integration process.

The first image summarization section 100 may select the reference image and the determination target image from the plurality of images, calculate the coverage ratio of the determination target image by the reference image as the similarity based on the deformation information about the reference image and the determination target image, and perform the first image summarization process that determines whether or not the determination target image can be deleted based on the coverage ratio.

The coverage ratio is information that represents the degree by which the object captured within the determination target image is captured within the reference image. For example, when an image having an aspect ratio of 1:1 is acquired, a 10×10 m (dimensions in the real space) square object is captured over the entire determination target image, and a 5×5 m square object that is included in the 10×10 m square object is captured over the entire reference image. In this case, a 100 $m^2$ (area in the real space) area is captured within the determination target image, and a 25 $m^2$ (area in the real space) area (that is included in the 100 $m^2$ area) is captured within the reference image. Therefore, the reference image covers 25% of the determination target image. In this case, the coverage ratio is 25%, 25 $m^2$, or 0.25, for example. Since a planar object is rarely captured almost perpendicularly, the reference image and the determination target image normally differ in the shape of the object even if an identical object is captured within the reference image and the determination target image. According to the first embodiment, the deformation information corresponding to such a deformation is acquired using the method disclosed in JP-A-2011-24763 or the like, and the coverage ratio is calculated using the deformation information. Note that the coverage ratio is information that represents the degree of coverage of the determination target image by the reference image, and is not limited to a ratio and the like.

Whether or not the determination target image can be deleted is determined by performing a comparison process using a given threshold value, for example. It is expected that the degree by which an area that cannot be observed occurs due to deletion of an image can be reduced by increasing the threshold value (e.g., setting the threshold value to a value close to 100%). On the other hand, the number of images included in the summary image sequence can be reduced by decreasing the threshold value. Since the effect of reducing the degree by which an area that cannot be observed occurs due to deletion of an image and the effect of reducing the number of images included in the summary image sequence have a trade-off relationship, and can be controlled by appropriately setting the threshold value, it is desirable to appropriately set the threshold value corresponding to the situation.

The above configuration makes it possible to prevent a situation in which an object area that cannot be observed occurs due to deletion of an image during the first image summarization process, and control the degree by which occurrence of such an object area is prevented. Specifically, when a value that corresponds to x% is used as the threshold value used to determine whether or not the determination target image can be deleted (deletion determination process), the method according to the first embodiment ensures that x% of the object captured within the determination target image is covered by the reference image even when the determination target image is deleted. Note that an area of the determination target image that is covered by the reference image may be less than x% even when a value that corresponds to x% is used as the threshold value since it is difficult to accurately calculate the deformation of the object within the image as the deformation information without an error.

When the first to Nth (N is an integer equal to or larger than 2) images have been input as the input image sequence, the first image summarization section 100 may select the pth image as the first reference image, select the qth (q is an integer that satisfies p+2≤q≤N−1) image as the second reference image, and select the rth (r is an integer that satisfies p+1≤r≤q−1) image as the determination target image. The first image summarization section 100 may calculate the coverage ratio based on the deformation information about the first reference image and the determination target image and the deformation information about the second reference image and the determination target image, and determine whether or not the determination target image can be deleted based on the calculated coverage ratio. When it has been determined that the (p+1)th to (q−1)th images can be deleted, the first image summarization section 100 may select the (q+1)th image as the second reference image.

This makes it possible to set the reference images to precede or follow the determination target image (see FIGS. 3A and 3B), and implement the image summarization process based on the coverage ratio. Since two reference images are used, it is likely that it is determined that the determination target image can be deleted as compared with the case where one reference image is set, for example, and the number of images included in the summary image sequence (the number of images after the summarization process) can be reduced.

The first image summarization section 100 may allow the image selected as the first reference image to remain in the first summary image sequence when it has been determined that at least one image among the (p+1)th to (q−1)th images cannot be deleted. The first image summarization section 100 may select the (q−1)th image as the first reference image, and perform the process again.

This makes it possible to allow the first reference image to remain in the first summary image sequence. Since the case where at least one of the determination target images situated between the first reference image and the second reference image cannot be deleted corresponds to the case where the interval between the first reference image and the second reference image is increased to a large extent, it is necessary to allow the image that precedes (immediately precedes in a narrow sense) the second reference image to remain in the first summary image sequence. Therefore, the (q−1)th image is selected as the next first reference image, and the process is performed again.

Note that the second reference image selection (update) process during the first image summarization process is not limited to the method that sequentially shifts the second reference image to the image of the input image sequence that follows the current second reference image.

For example, the second reference image is selected from the second reference image selection interval in which the starting point and the end point are set corresponding to the (p+2)th to Nth images, and whether or not the determination target image can be deleted is determined based on the first reference image and the second reference image. In this case, the first image summarization section 100 may select the xth (x is an integer that satisfies x>q) image included in the second reference image selection interval as the next second reference image when it has been determined that the (p+1)th to (q−1)th images can be deleted, and update the starting point of the second reference image selection interval with the qth image. The first image summarization section 100 may select the yth (y is an integer that satisfies y<q) image included in the second reference image selection interval as the next second reference image when it has been determined that at least one image among the (p+1)th to (q−1)th images cannot be deleted, and update the end point of the second reference image selection interval with the qth image.

The second reference image selection interval represents a candidate for the second reference image, and represents a candidate for the similarity summary image that is allowed to remain in the first summary image sequence (i.e., the next similarity summary image that follows the similarity summary image that has been found in a narrow sense). Therefore, the second reference image selection interval corresponds to the similarity summary image search range.

This makes it possible to flexibly determine the position of the next second reference image when updating the second reference image. Since the method that sequentially shifts the second reference image to the image that follows the current second reference image narrows the search range by thoroughly checking the search range from the first image, the amount of calculations may significantly increase depending on the position of the correct answer. In contrast, the search range can be significantly narrowed by the unit determination (one second reference image selection process and one deletion determination process) by allowing a non-adjacent image to be selected as the next second reference image. This makes it possible to reduce the amount of calculations, and reduce the load imposed on the system, or reduce the processing time. Since the backward search process is not limited to a process that selects the adjacent image, the range that precedes the current second reference image may not have been searched, and may include a correct answer depending on the deletion determination result. The forward search process is also enabled taking account of such a situation, and is not limited to a process that selects the adjacent image as the second reference image.

When the jth (j is an integer) image corresponds to the end point of the second reference image selection interval, the first image summarization section 100 may set the value x based on the value $(q+j)/2$. Alternatively, when the ith (i is an integer) image corresponds to the starting point of the second reference image selection interval, the first image summarization section 100 may set the value y based on the value $(i+q)/2$.

This makes it possible to use the binary search method when selecting the next second reference image. The image that is situated between the current second reference image and the end point is selected when performing the backward search process, and the image that is situated between the current second reference image and the starting point is selected when performing the forward search process. This makes it possible to halve the search range (corresponding to the length of the second reference image selection interval). It is expected that the entire search range is completely searched when $\log N$ images are selected as the second reference image. Therefore, the amount of calculations can be reduced to $N \times \log N$. When N is very large, the amount of calculations can be significantly reduced as compared with the method that sequentially shifts the second reference image to the image that follows the current second reference image (the amount of calculations is $N^2$). Note that the value $(q+j)/2$ and the value $(i+q)/2$ are not necessarily an integer, and an image corresponding to each value may be absent. In such a case, the maximum integer that does not exceed the value $(q+j)/2$, or an integer that is larger than the value $(q+j)/2$ by 1 may be used, for example. Note that the second reference image need not necessarily be updated using the binary search method, but may be updated using various other methods. For example, when the position of a correct answer within the search range is predicted to some extent, the amount of calculations is expected to be reduced by selecting the second reference image so that the predicted position and its peripheral positions can be mainly searched.

The first image summarization section 100 may calculate the coverage area that is an area in which the determination target image is covered by the reference image based on the deformation information about the reference image and the determination target image, and calculate the ratio of the coverage area to the determination target image as the coverage ratio.

This makes it possible to calculate the coverage ratio based on the coverage area. The coverage area is the area illustrated in FIG. 2. The coverage area is an area obtained by deforming the reference image based on the deformation information, and projecting the deformed reference image onto the determination target image. The object area captured within the reference image corresponds to (or coincides with (when the deformation information includes no error (ideal situation))) the object area captured within the calculated coverage area. Therefore, the coverage ratio can be calculated from the ratio (i.e., area ratio) of the coverage area to the determination target image. Note that the coverage area is calculated by deforming the reference image based on the deformation information, and the calculated coverage area need not necessarily be projected onto the determination target image. The coverage area need not necessarily be calculated based on the entirety of the reference image. The coverage area may be calculated by deforming part of the reference image based on the deformation information.

The second image summarization section 200 may set consecutive images among the plurality of images that include an identical target object, or consecutive images among the plurality of images that have been recognized to be an identical scene, to be the consecutive image sequence from which the summary image is extracted, based on the recognition process, and perform the second image summarization process that extracts at least one image from the consecutive image sequence as the summary image.

Note that at least one image extracted from the consecutive image sequence as the summary image refers to the object summary image that is allowed to remain in the second summary image sequence.

This makes it possible to implement the second image summarization process using the method that sets the consecutive image sequence (segment) described above with reference to FIGS. 5 and 6. Since the consecutive image sequence includes consecutive images that include an identical target object, or consecutive images that have been recognized to be an identical scene, it is possible to reduce the image redundancy while preventing a situation in which the target object or the scene is not included in the summary image sequence, by extracting images from the consecutive image sequence in a number smaller than the number of images included in the consecutive image sequence as the object summary image. Note that the redundancy can be further reduced by reducing the number of images extracted from the consecutive image sequence as the summary image. For example, only one image may be extracted from the consecutive image sequence as the summary image.

The second image summarization section 100 may select the summary image (object summary image) extracted from the consecutive image sequence based on the area of the target object.

According to this configuration, since an image in which the target object is captured to occupy a large area can be extracted as the summary image, observation by the user can be facilitated, for example. The user may not be able to easily observe the target object even if the target object has a large area, when the target object is dark due to a small brightness value, when the target object has an extreme shape and is not suitable for observation, or when the target object is situated in the peripheral area of the image, and affected by distortion to a large extent, for example. Therefore, information about the results of the image recognition process or the image detection process (e.g., the position of the target object within the image, color information, texture information, or recognition/detection accuracy) may be used in addition to the area of the target object. In this case, since the image summarization process can be performed taking account of the image features of the target object, an image in which the detected target object can be easily observed can be selected as the summary image, and the target object can be more easily determined.

The integration processing section 300 may perform the integration process on the first summary image sequence and the second summary image sequence by selecting an image that is included in at least one of the first summary image sequence and the second summary image sequence as the summary image (output summary image) of the output summary image sequence.

This makes it possible to implement the integration process illustrated in FIG. 7. Since the integration process according to the first embodiment can be implemented using a simple method (see FIG. 7 (flowchart)), the processing load can be reduced.

The first image summarization section 100 may detect a scene change based on the similarity between the plurality of images, and perform the first image summarization process based on the scene change.

According to this configuration, since consecutive similar images are deleted by performing the image summarization process based on a scene change, redundant similar scenes can be deleted, and the summary image sequence can be generated while efficiently reducing the number of images. Since the above process utilizes the similarity between a plurality of images, it suffices to detect that the a first scene captured within a first image differs from a second scene captured within a second image, and it is unnecessary to determine a specific scene that corresponds to the first scene or the second scene. On the other hand, the scene recognition process during the second image summarization process must determine whether or not the scene captured within the processing target image coincides with the detection target scene, and store the feature quantity and the like of the detection target scene, for example.

The plurality of images may be a capsule endoscopic image. The second image summarization section 200 may perform the recognition process on an in vivo attention area captured within the capsule endoscopic image as the target object.

The term "attention area" used herein refers to an area for which the user's observation priority is relatively higher than that of other areas. For example, when the user is a doctor, and desires to perform treatment, the attention area refers to an area in which a mucous membrane area or a lesion area is captured. If the doctor desires to observe bubbles or feces, the attention area refers to an area in which a bubble area or a feces area is captured. Specifically, the attention area for the user differs depending on the objective of observation, but is necessarily an area for which the user's observation priority is relatively higher than that of other areas.

This makes it possible to apply the image summarization process according to the first embodiment to an image captured using a capsule endoscope. In the medical field, it is necessary to prevent a situation in which a lesion or the like is missed as much as possible. When the attention area is used as the target object during the second image summarization process, it is possible to efficiently allow an image in which the attention area has been detected to remain in the summary image sequence. However, the attention area is not necessarily detected successfully. Therefore, the target object may not be detected by the recognition process from an image in which the attention area is captured, and the image may be deleted without being determined to be a candidate for the object summary image. Accordingly, it is advantageous to use the image summarization process that utilizes the similarity (coverage ratio in a narrow sense) in combination with the above process. In particular, since it is difficult for the doctor to externally operate a capsule endoscope that is situated inside the body, and efficiently change the imaging target, a large number of similar images may be acquired. The process is normally performed after a large number of images have been stored instead of sequentially checking the captured image in real time since the operation is difficult. Therefore, it is advantageous to perform the image summarization process according to the first embodiment on an image sequence acquired by a capsule endoscope.

The second image summarization section 200 may perform the recognition process on the in vivo attention area based on a special light image acquired by applying light within a specific wavelength band.

According to this configuration, since observation can be performed using the special light, the target object detection accuracy during the second image summarization process can be improved, and it is possible to prevent a situation in which an image in which an important object (attention area) is captured is deleted by the image summarization process. Note that it is desirable to use the first image summarization process that utilizes the similarity in combination with the above process even if the target object detection accuracy can be improved. In this case, it is possible to improve the effect of preventing a situation in which the attention area is missed.

The specific wavelength band may be a band that is narrower than the wavelength band of white light. Specifically, the special light image may be an in vivo image, and the specific wavelength band may be the wavelength band of light absorbed by hemoglobin in blood. More specifically, the specific wavelength band may be a wavelength band of 390 to 445 nm or 530 to 550 nm. This corresponds to narrow band imaging (NBI).

This makes it possible to observe the structure of a surface area of in vivo tissue and a blood vessel situated in a deep area. A lesion (e.g., epidermoid cancer) or the like that cannot be easily observed using normal light can be displayed in brown or the like by inputting the resulting signal to a specific channel (R, G, or B), so that a situation in which a lesion area is missed can be prevented. The wavelength band of 390 to 445 nm or 530 to 550 nm is selected from the viewpoint of absorption by hemoglobin and the ability to reach a surface area or a deep area of tissue.

Note that the light having the specific wavelength band is not limited to light corresponding to NBI, but may be light corresponding to autofluorescence imaging (AFI) or infrared imaging (IRI).

The first embodiment may also be applied to a program that causes a computer to function as the first image summarization section 100 that performs the first image summarization process based on the similarity between a plurality of images to acquire the first summary image sequence, the second image summarization section 200 that performs the second image summarization process based on the target object/scene recognition process on each image among the plurality of images to acquire the second summary image sequence, and the integration processing section 300 that performs the integration process on the first summary image sequence and the second summary image sequence, or performs the integration process on the first image summarization process and the second image summarization process to acquire the output summary image sequence.

This makes it possible to implement a program that implements the above image summarization process. For example, when the image summarization process is implemented by an information processing system such as a PC, the program is read and executed by a processing section (e.g., CPU or GPU) included in the PC. The program is stored in an information storage medium. The information storage medium may be an arbitrary recording medium that is readable by an information processing system (e.g., PC), such as an optical disk (e.g., DVD and CD), a magnetooptical disk, a hard disk (HDD), or a memory (e.g., nonvolatile memory and RAM).

3. Second Embodiment

The second embodiment is described below. A system configuration example of an image summarization device according to the second embodiment is the same as that illustrated in FIG. 1 (see the first embodiment), and detailed description thereof is omitted. The second embodiment differs from the first embodiment as to the integration process performed by the integration processing section 300. The difference from the first embodiment is described in detail below.

The first summary image sequence is acquired by the first image summarization process, and the second summary image sequence is acquired by the second image summarization process in the same manner as described above in connection with the first embodiment. In the second embodiment, the second summary image sequence is updated based on the first summary image sequence before integrating the first summary image sequence and the second summary image sequence.

Figure 8A:
FIGS. 8A and 8B are views illustrating a second summary image sequence update process.
Figure 8B:
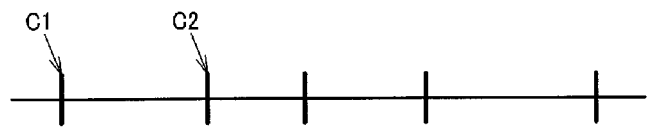

FIGS. 8A and 8B are views illustrating the integration process according to the second embodiment. In FIG. 8A, the continuous horizontal straight line indicates the input image sequence (i.e., a plurality of images included in the input image sequence). Each vertical line indicates the object summary image selected as a result of the second image summarization process. Each horizontal arrow in FIG. 8A indicates that the target object or the like was successively detected in the images included in the range. Each arrow corresponds to the consecutive image sequence (segment). In FIG. 8B, the continuous horizontal straight line indicates the input image sequence, and each vertical line indicates the similarity summary image.

The integration process according to the second embodiment integrates (combines) a plurality of consecutive image sequences that have been set as a result of the second image summarization process into one integrated (combined) consecutive image sequence, and extracts at least one summary image from the integrated consecutive image sequence to reduce the number of object summary images included in the second summary image sequence.

A specific example of the integration process according to the second embodiment is described below. Two adjacent images among the similarity summary images included in the first summary image sequence are selected. When a plurality of consecutive image sequences set by the second image summarization process are included between the two similarity summary images, whether or not the plurality of consecutive image sequences can be integrated is determined.

Alternatively, adjacent consecutive image sequences may be selected instead of using adjacent similarity summary images, and whether or not the consecutive image sequences can be integrated may be determined based on whether or not the adjacent consecutive image sequences are situated between adjacent similarity summary images.

It is determined that the consecutive image sequence is situated between two similarity summary images when at least one image included in the consecutive image sequence is situated between the two similarity summary images. Specifically, all of the images included in the consecutive image sequence need not necessarily be situated between the two similarity summary images.

When a given image included in the consecutive image sequence has been extracted, and the extracted image is situated between two similarity summary images, the consecutive image sequence from which the given image has been extracted may be subjected to the integration determination process. In this case, the image selected as the object summary image is normally extracted from the consecutive image sequence. Note that another image included in the consecutive image sequence may be extracted.

An example is described below with reference to FIGS. 8A and 8B. The consecutive image sequence B1 and the consecutive image sequence B2 illustrated in FIG. 8A are situated between two adjacent similarity summary images C1 and C2 illustrated in FIG. 8A according to the above definition. Therefore, whether or not the consecutive image sequence B1 and the consecutive image sequence B2 can be integrated is determined.

Figure 9A:
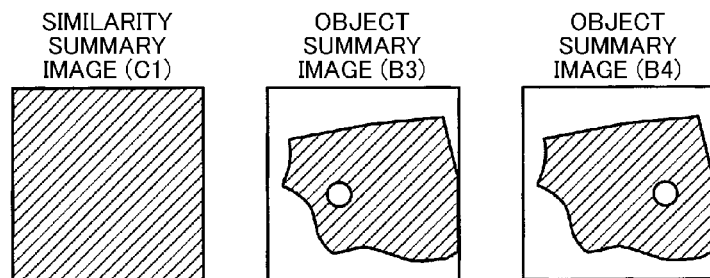
FIGS. 9A and 9B are views illustrating a second summary image sequence update determination process.

FIG. 9A illustrates a specific example of the consecutive image sequence integration determination process. The integration determination process is performed using the similarity summary image, and the object summary images selected from a plurality of processing target consecutive image sequences. Specifically, the similarity summary image is deformed, and projected onto each of a plurality of object summary images (in a number at least equal to the number of integration determination target consecutive image sequences) to calculate the coverage area. This process may be performed based on the deformation information about the images in the same manner as the first image summarization process that utilizes the coverage ratio.

Whether or not the target object detected from each object summary image is situated within the coverage area is determined, and it is determined that the determination target consecutive image sequences can be integrated into the integrated consecutive image sequence when the target object detected from each object summary image is situated within the coverage area. Since an identical object range is captured within the similarity summary image and each coverage area, it is likely that the target object is an identical object when the target object detected from each object summary image is situated within the coverage area. In this case, it is unnecessary to extract the object summary images in a number at least equal to the number of consecutive image sequences from a plurality of consecutive image sequences, and it suffices to integrate the plurality of consecutive image sequences, and extract at least one object summary image from the integrated consecutive image sequence.

Note that the object summary image extracted from the integrated consecutive image sequence (corresponding to the sum-set of the consecutive image sequence B1 and the consecutive image sequence B2 illustrated in FIG. 8A) coincides with one of the object summary images extracted from the consecutive image sequences before integration as long as the selection reference feature quantity is not changed.

Specifically, since the image B3 or B4 is extracted from the integrated consecutive image sequence as the object summary image (see FIG. 8A), the consecutive image sequence integration process in a narrow sense corresponds to a process that deletes the object summary image.

Figure 9B:
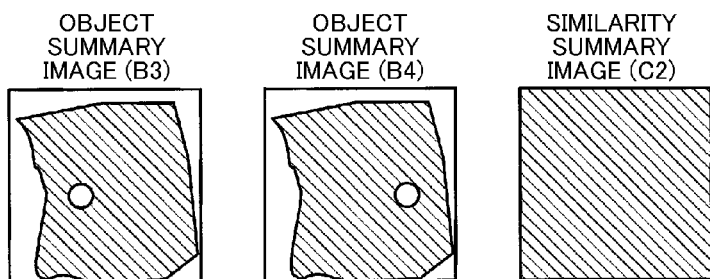

Since the similarity summary image is also present to follow the object summary image, a similar process is performed as illustrated in FIG. 9B. When it has been determined that the consecutive image sequences can be integrated as a result of the process illustrated in FIG. 9A or 9B, the consecutive image sequences are integrated.

Figure 10:
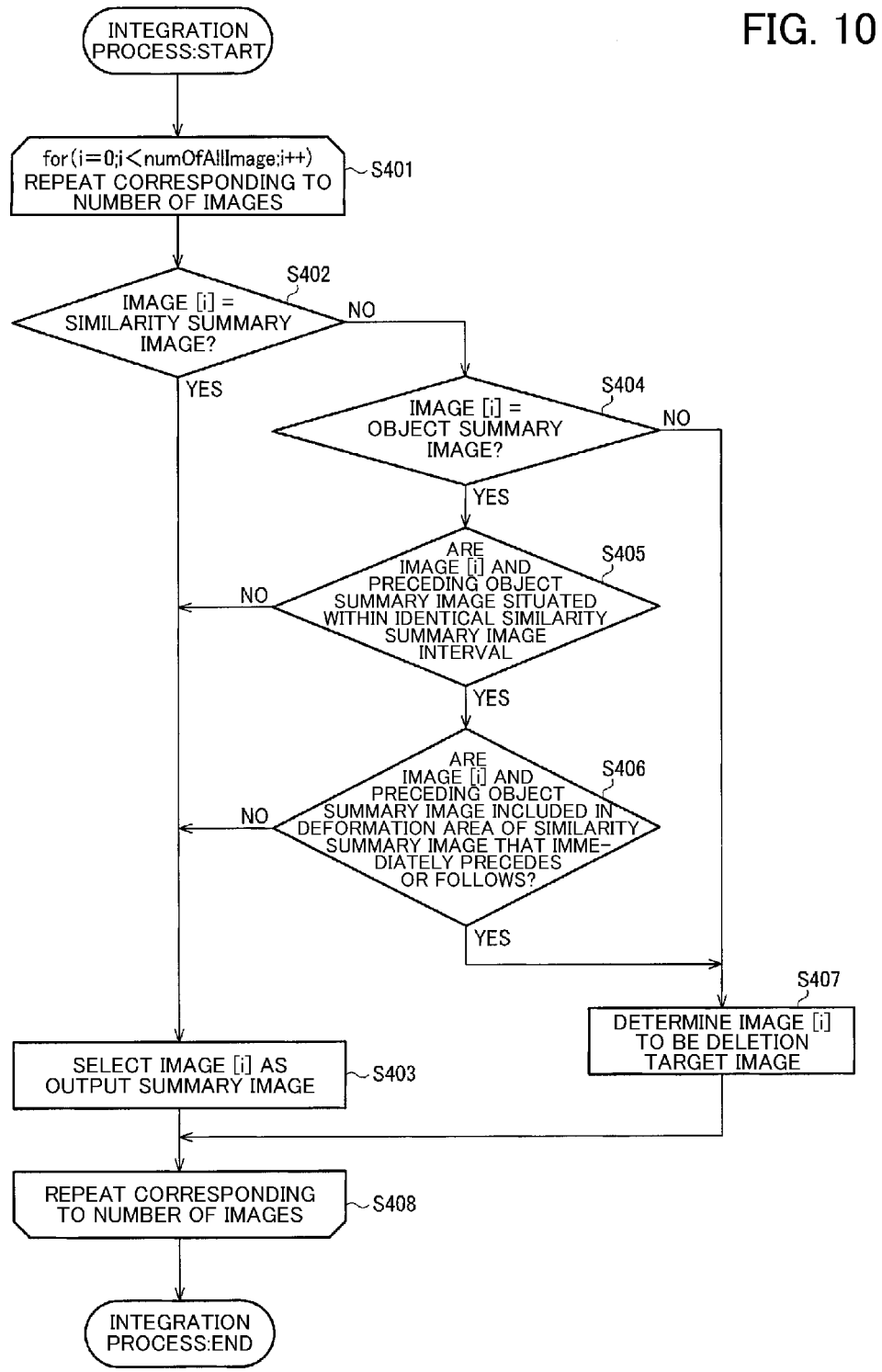
FIG. 10 is a flowchart illustrating an integration process according to a second embodiment.

FIG. 10 is a flowchart illustrating the integration process according to the second embodiment. As illustrated in FIG. 10, a loop process (S401 to S408) is performed during the integration process. The steps S402 to S407 are performed on all of the images of the input image sequence.

Specifically, whether or not the ith image of the input image sequence is included in the first summary image sequence is determined (S402). When the ith image is included in the first summary image sequence (Yes in S402), the ith image is selected as the output summary image (S403). When the ith image is not included in the first summary image sequence (No in S402), whether or not the ith image is included in the second summary image sequence is determined (S404). When the ith image is not included in the second summary image sequence (No in S404), the ith image is determined to be the deletion target image (S407). When the ith image is included in the second summary image sequence (Yes in S404), the determination process based on the relationship with the similarity summary image is performed on the ith image and the preceding object summary image (S405). Specifically, whether or not the ith image and the preceding object summary image are situated between the adjacent similarity summary images is determined (see FIGS. 8A and 8B). When the ith image and the preceding object summary image are not situated between the adjacent similarity summary images (No in S405), the consecutive image sequences are not integrated, and the ith image is not deleted from the second summary image sequence. Therefore, the ith image is selected as the output summary image in the step S403.

When the ith image and the preceding object summary image are situated between the adjacent similarity summary images (Yes in S405) (i.e., when it may be possible to integrate the consecutive image sequences), the determination process illustrated in FIGS. 9A and 9B is performed (S406). When the determination result in the step S406 is No (i.e., the consecutive image sequences are not integrated), the ith image is not deleted from the second summary image sequence. Therefore, the ith image is selected as the output summary image in the step S403. When the determination result in the step S406 is Yes (i.e., the consecutive image sequences are integrated), the ith image is determined to be the deletion target image in the step S407. The above process is performed on the entire input image sequence while incrementing the value i (initial value: i=0).

Note that the flowchart illustrated in FIG. 10 merely illustrates an example of the process according to the second embodiment in that the number of consecutive image sequences that are integrated at a time is limited to two, and the object summary image corresponding to the backward consecutive image sequence is deleted when the consecutive image sequences are integrated, for example. The process according to the second embodiment may be implemented by a process that differs from the process illustrated in FIG. 10.

According to the second embodiment, the integration processing section 300 integrates a plurality of consecutive image sequences that have been set during the second image summarization process into one integrated consecutive image sequence based on the first summary image sequence, and extracts at least one image from the integrated consecutive image sequence as the summary image (object summary image) to update the second summary image sequence.

This makes it possible to update the second summary image sequence based on the first summary image sequence. The second summary image sequence is updated in a narrow sense by deleting an object summary image among the object summary images to reduce the number of images included in the second summary image sequence. The consecutive image sequences may be integrated by performing the process illustrated in FIGS. 8A, 8B, and 9, or may be integrated using another method.

The integration processing section 300 may perform the integration process on the first summary image sequence and the second summary image sequence by selecting an image that is included in at least one of the first summary image sequence and the updated second summary image sequence as the summary image (output summary image) of the output summary image sequence.

This makes it possible to perform the integration process on the first summary image sequence and the second summary image sequence using the updated second summary image sequence. Therefore, it is possible to reduce the number of images included in the output summary image sequence as compared with the case where the update process is not performed (e.g., first embodiment) while achieving the advantages of the image summarization process that utilizes the similarity and the image summarization process that utilizes the target object/scene recognition process, and improve convenience to the user who utilizes the output summary image sequence, for example.

4. Third Embodiment

The third embodiment is described below. FIG. 11 illustrates a system configuration example of an image summarization device according to the third embodiment. As illustrated in FIG. 11, the basic configuration is the same as that described above in connection with the first embodiment, except that the first image summarization section 100 and the integration processing section 300 are bidirectionally connected.

In the third embodiment, the integration processing section 300 acquires the results of the second image summarization process, and causes the first image summarization section 100 to perform the first image summarization process based on the acquired results.

Figure 12A:
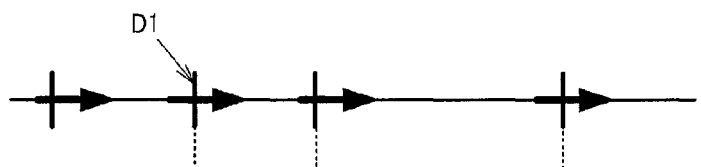
FIGS. 12A to 12C are views illustrating a method according to a third embodiment.
Figure 12B:
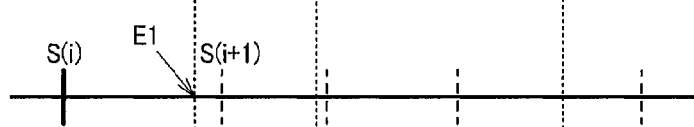
Figure 12C:
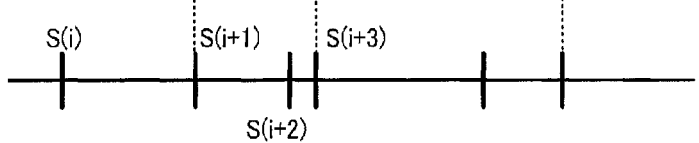

FIGS. 12A to 12C illustrate a specific example of the above process. The description given above in connection with FIGS. 8A and 8B also applies to FIGS. 12A to 12C. As illustrated in FIG. 12A, the second summary image sequence is acquired by extracting at least one summary image from the consecutive image sequence based on the target object/scene recognition process (see the first embodiment), for example. The first image summarization process is performed as illustrated in FIG. 12B (see the first embodiment, for example). When the image S(i) has been selected as the similarity summary image (first reference image), the image S(i+1) (i.e., the next similarity summary image) is searched by performing the determination process based on the coverage ratio after setting the second reference image.

However, an image that has been determined to be deleted based on the similarity (coverage ratio) should be selected as the output summary image when the target object (observation target) is captured within the image, and the image represents the consecutive image sequence. The first embodiment implements such an integration process. Therefore, the same effects as described above can be expected to be achieved by selecting the similarity summary image (or the first reference image) during the first image summarization process using the results of the second image summarization process in addition to the similarity.

In the third embodiment, when searching the next similarity summary image after setting the similarity summary image (first reference image), an image that has been set to the object summary image is selected as the similarity summary image regardless of the similarity. As illustrated in FIG. 12B, the image indicated by E1 is determined to be the deletion target image based on the similarity. However, the image indicated by E1 has been selected as the object summary image (see D1 in FIG. 12A). Therefore, the image indicated by E1 is set to be the similarity summary image S(i+1) during the first image summarization process according to the second embodiment.

The summary image may be set when a given condition has been satisfied based on the similarity, or when the summary image of the second summary image sequence has been found. In the example illustrated in FIG. 12C, the image S(i+2) has been selected based on the similarity, and the image S(i+3) has been selected based on the object summary image. The position of the similarity summary image in a narrow sense (the result of the first image summarization process according to the first embodiment) in the image sequence is determined depending on another similarity summary image (the preceding similarity summary image in a narrow sense). Therefore, when the similarity summary image has been selected taking account of the results of the second image summarization process, the images selected as the similarity summary image normally differ to a large extent as compared with the case where the results of the second image summarization process are not used.

Since the image sequence that takes account of both the target object/scene recognition process and the similarity can be acquired by the first image summarization process based on the results of the second image summarization process, the output summary image sequence may be generated using the results of the first image summarization process.

Figure 13:
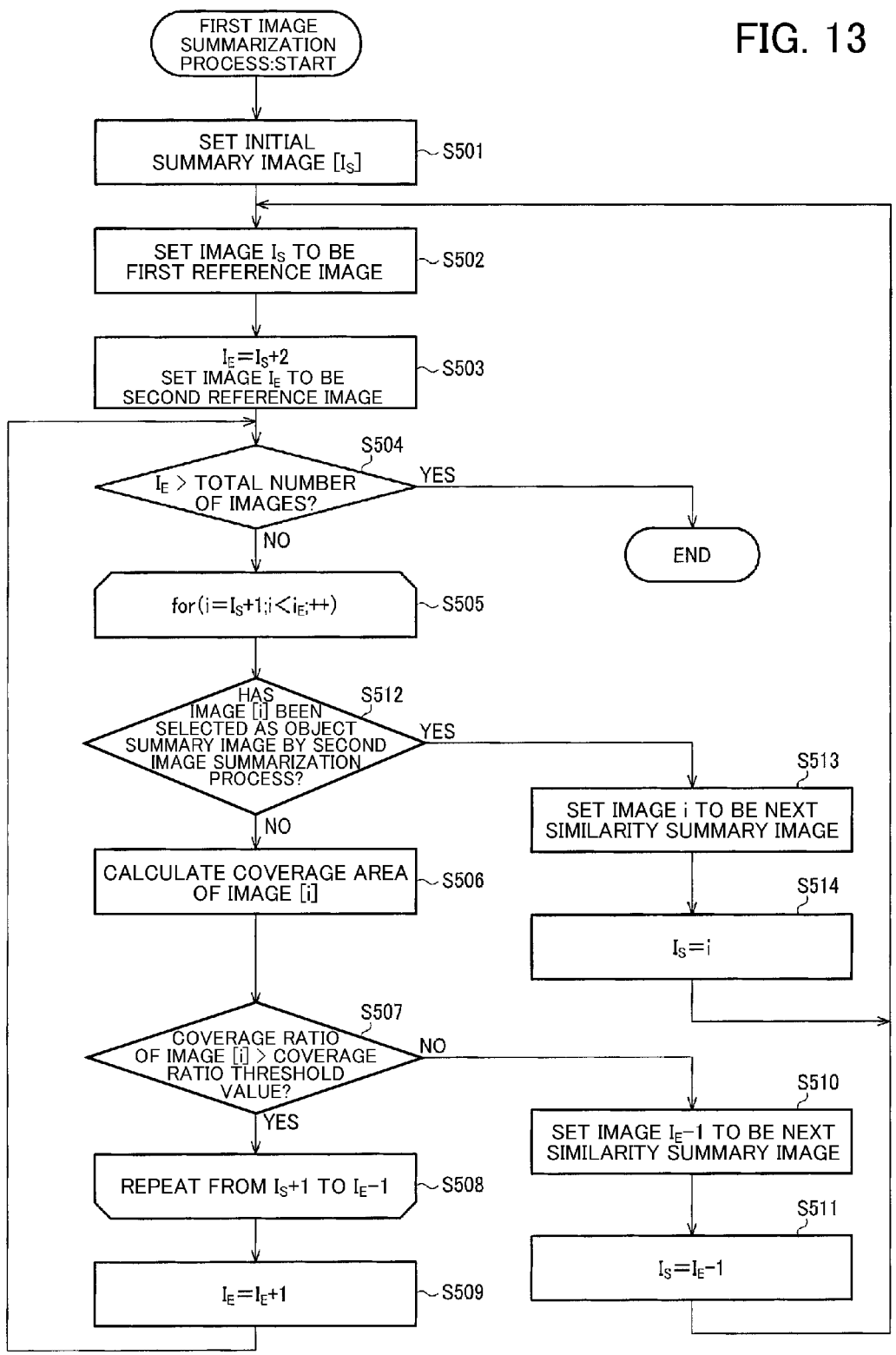
FIG. 13 is a flowchart illustrating an integration process according to the third embodiment.

FIG. 13 is a flowchart illustrating the integration process according to the third embodiment. Note that FIG. 13 actually illustrates the first image summarization process based on the results of the second image summarization process (see FIG. 4).

Steps S501 to S511 illustrated in FIG. 13 are performed in the same manner as the steps S101 to S111 illustrated in FIG. 4, respectively, and detailed description thereof is omitted. In FIG. 13, steps S512 to S514 are added after the step S505 illustrated in FIG. 4. In the step S512, whether or not the processing target ith image has been selected as the object summary image as a result of the second image summarization process is determined. When it has been determined that the ith image has been selected as the object summary image as a result of the second image summarization process (Yes in S512), the ith image is set to be the next similarity summary image (S513), $I_S$ is set to i (S514), and the similarity summary image set in the step S514 is set to be the next first reference image (S502).

According to the third embodiment, the integration processing section 300 performs the integration process on the first image summarization process and the second image summarization process by causing the first image summarization section to perform the first image summarization process based on the results of the second image summarization process.

According to this configuration, since the image summarization process based on the determination as to the similarity between the images, and the image summarization process based on the target object/scene recognition process, can be integrated to acquire the output summary image sequence, it is possible to implement an image summarization process that achieves the advantages of each image summarization process.

The first image summarization section 100 may select the image (object summary image) included in the second summary image sequence from the plurality of images as the reference image based on the integration process, select the determination target image from the plurality of images, calculate the coverage ratio of the determination target image by the reference image as the similarity based on the deformation information about the reference image and the determination target image, and perform the first image summarization process that determines whether or not the determination target image can be deleted based on the coverage ratio.

This makes it possible to perform the reference image selection process during the first image summarization process based on the results of the second image summarization process as the integration process on the first image summarization process and the second image summarization process. More specifically, the object summary image included in the second summary image sequence may be selected as the reference image, and the image other than the object summary image may be processed based on the similarity.

The integration processing section 300 may acquire the first summary image sequence generated by the first image summarization section as the output summary image sequence via the integration process.

This makes it possible to utilize the results of the first image summarization process based on the second image summarization process as the output summary image sequence. According to the third embodiment, an image that has been selected as the summary image (object summary image) as a result of the second image summarization process is selected as the summary image (similarity summary image) during the first image summarization process. Therefore, since the image based on the target object/scene recognition process is allowed to remain during the first image summarization process, it is unnecessary to take account of the integration process on the first summary image sequence and the second summary image sequence, for example.

5. Fourth Embodiment

The fourth embodiment is described below. A system configuration example of an image summarization device according to the fourth embodiment is the same as that illustrated in FIG. 11 (see the third embodiment), and detailed description thereof is omitted. The fourth embodiment utilizes a method that combines the method according to the third embodiment with the second summary image sequence update process (consecutive image sequence integration process) according to the second embodiment. Specifically, the first image summarization process based on the results of the second image summarization process is performed in the same manner as in the third embodiment, and whether or not the second summary image sequence can be updated is determined based on the acquired first summary image sequence. When the second summary image sequence can be updated, the first image summarization process is performed based on the results of the second image summarization process after the update process, and the acquired new first summary image sequence is acquired as the output summary image sequence.

Figure 14A:
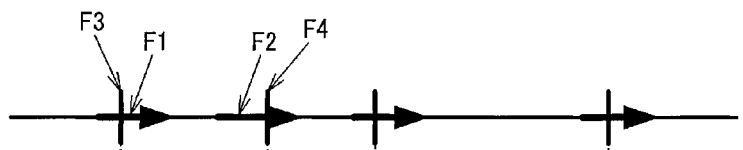
FIGS. 14A to 14E are views illustrating a method according to a fourth embodiment.
Figure 14B:
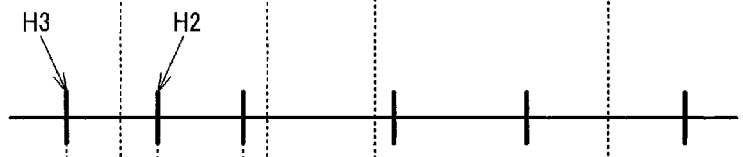
Figure 14C:

FIGS. 14A to 14E illustrate a specific example of the above process. FIG. 14A illustrates the second summary image sequence that is acquired first, and FIG. 14B illustrates the first summary image sequence when the results of the second image summarization process are not used. Since the first image summarization process is performed using the results of the second image summarization process in the same manner as in the third embodiment, the first summary image sequence illustrated in FIG. 14C is acquired.

After the first summary image sequence illustrated in FIG. 14C has been acquired, whether or not the second summary image sequence (see FIG. 14A) can be updated is determined using the first summary image sequence. Specifically, whether or not a plurality of consecutive image sequences can be integrated into the integrated consecutive image sequence is determined in the same manner as described above in connection with the second embodiment. For example, the consecutive image sequences F1 and F2 illustrated in FIG. 14A are situated between adjacent similarity summary images G1 and G2, and subjected to the integration determination process.

Figure 14D:

When the second summary image sequence has been updated as illustrated in FIG. 14D, the object summary image indicated by F3 in FIG. 14A is deleted. Therefore, the image corresponding to the object summary image indicated by F3 need not be allowed to remain in the output summary image. Specifically, since the image G1 included in the first summary image sequence illustrated in FIG. 14C is unnecessary, it is necessary to change the first summary image sequence. In this case, the first image summarization process is performed again based on the updated second summary image sequence illustrated in FIG. 14D, and the new first summary image sequence illustrated in FIG. 14E is acquired.

Figure 14E:

Note that the process may be performed on the entire input image sequence when acquiring the first summary image sequence illustrated in FIG. 14E. However, since the deletion target image in FIG. 14C can be determined by updating the second summary image sequence, it can be determined that the images that precede the similarity summary image (G3) that precedes the deletion target image G1 do not change without performing the first image summarization process again. Therefore, the process may be performed on only the images that follow the image G3 illustrated in FIG. 14C.

Figure 15:
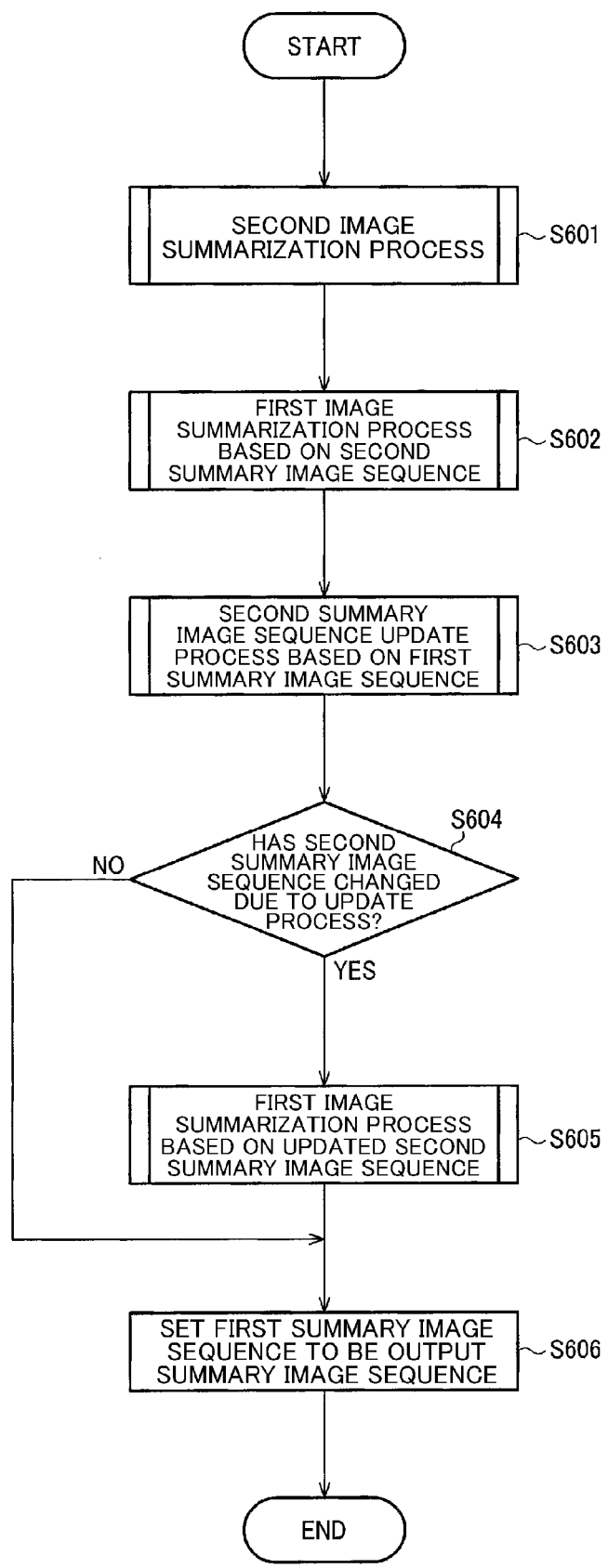
FIG. 15 is a flowchart illustrating an integration process according to the fourth embodiment.

FIG. 15 is a flowchart illustrating the integration process according to the fourth embodiment. The second image summarization process is performed (S601). The process in the step S601 corresponds to the process illustrated in FIG. 5. The first image summarization process is performed based on the results (the second summary image sequence in a narrow sense) of the second image summarization process (S602). The process in the step S602 corresponds to the process illustrated in FIG. 13.

The second summary image sequence is updated based on the first summary image sequence (S603). The process in the step S603 corresponds to the process in the steps S404 to S406 illustrated in FIG. 10, for example. Whether or not the second summary image sequence has changed as a result of the update process (whether or not a summary image among the summary images included in the second summary image sequence has been deleted in a narrow sense) is determined (S604). When the second summary image sequence has changed as a result of the update process, the first image summarization process is performed based on the updated second summary image sequence (S605). After completion of the step S605, or when the second summary image sequence has not changed as a result of the update process (No in S604), the corresponding first summary image sequence is set to be the output summary image sequence (S606), and the process is terminated. When the second summary image sequence has changed as a result of the update process (Yes in S604), the processing results in the step S605 are set to be the output summary image sequence. When the second summary image sequence has not changed as a result of the update process (No in S604), the processing results in the step S602 are set to be the output summary image sequence.

When the first image summarization process based on the results of the second image summarization process is referred to as "step A", and the second summary image sequence update process based on the first summary image sequence is referred to as "step B", the first step A (corresponding to the S602 illustrated in FIG. 15) and the step B (S603) using the results of the first step A are performed, and the second step A (S605) is performed using the results of the step B. Note that it is likely that the second step B can be performed using the results of the second step A (i.e., the second summary image sequence changes as a result of the update process) depending on the input image sequence.

As a modification of the fourth embodiment, the step A and the step B may be repeated an arbitrary number of times using the results of the preceding step. In this case, the process may be terminated when the step A has been performed N (N is an integer equal to or larger than 2) times, and the results may be set to be the output summary image sequence. Alternatively, when it has been detected that the step B could not be performed (or when it has been detected that the second summary image sequence did not change although the step B was performed), the results of the preceding the step A may be set to be the output summary image sequence.

According to the fourth embodiment, the integration processing section 300 determines whether or not the second summary image sequence update process that reduces the number of images included in the second summary image sequence can be performed based on the first summary image sequence generated by the first image summarization section via the integration process.

This makes it possible to determine whether or not the second summary image sequence update process (see the second embodiment) can be performed using the first summary image sequence when using the method according to the third embodiment (the first summary image sequence is set directly to be the output summary image sequence in the third embodiment). The integration process on the first image summarization process and the second image summarization process has been performed when the first summary image sequence has been calculated (see the third embodiment). However, the results of the integration process do not take account of a reduction in the number of images included in the output summary image sequence. Since convenience to the user can be improved by reducing the number of images included in the output summary image sequence, it is advantageous to reduce the number of images included in the output summary image sequence. The number of images included in the output summary image sequence can be reduced by the second summary image sequence update process (e.g., consecutive image sequence integration process) used in the second embodiment.

The integration processing section 300 may perform the second summary image sequence update process when it has been determined that the second summary image sequence update process can be performed. The integration processing section 300 may perform the integration process on the first image summarization process and the second image summarization process by causing the first image summarization section to perform the first image summarization process based on the results of the second image summarization process after the second summary image sequence update process.

This makes it possible to perform the first image summarization process based on the results (updated second summary image sequence) of the second image summarization process after the second summary image sequence update process. The number of object summary images included in the second summary image sequence can be reduced (from FIG. 14A to FIG. 14D) by performing the second summary image sequence update process. However, the deletion process is not reflected directly in the first summary image sequence (FIG. 14 C) corresponding to the output summary image sequence. When the image F3 in FIG. 14 A has been deleted by the update process, it is undesirable to merely delete the corresponding image (G1 in FIG. 14C) from the first summary image sequence. This is because the images situated between the image G3 and the image G2 cannot be covered based on the similarity when the image H2 (or the image that is closer to the image H3 than the image H2) is not selected as the next similarity summary image that follows the image H3 (see FIG. 14B (i.e., the results of the first image summarization process that does not take account of the second image summarization process). However, when the image G1 in FIG. 14C is deleted, the images situated between the image G3 and the image G2 cannot be covered since the interval between the image G3 and the image G2 is too long. Therefore, when the second summary image sequence update process has been performed (see FIGS. 14A and 14D), it is desirable to perform the first image summarization process again using the updated second summary image sequence to acquire the first summary image sequence illustrated in FIG. 14E instead of merely deleting the image G1 (see FIG. 14C).

The integration processing section 300 may acquire the first summary image sequence generated by the first image summarization section as the output summary image sequence via the integration process.

This makes it possible to set the first summary image sequence acquired by the first image summarization process based on the updated second summary image sequence to be the output summary image sequence. Since the image based on the target object/scene recognition process is allowed to remain during the first image summarization process in the same manner as in the third embodiment, it is unnecessary to take account of the integration process on the first summary image sequence and the second summary image sequence, for example. The second summary image sequence may not change (i.e., the number of object summary images cannot be reduced) even when the second summary image sequence update process has been performed. In this case, even if the first image summarization process is performed based on the updated second summary image sequence, the output results are the same as those obtained by the first image summarization process based on the second summary image sequence that is not updated. Therefore, it is desirable to skip the first image summarization process based on the updated second summary image sequence (see the flowchart illustrated in FIG. 15). In this case, the first summary image sequence based on the original second summary image sequence is acquired as the output summary image sequence (i.e., the processing results in the step S602 in FIG. 15).

6.. Fifth Embodiment

The fifth embodiment is described below. A system configuration example of an image processing device will be described first, the flow of the process will then be described using a flowchart, and the details of the first deletion determination process and the second deletion determination process will be described thereafter.

6.1 System Configuration Example

Figure 17:
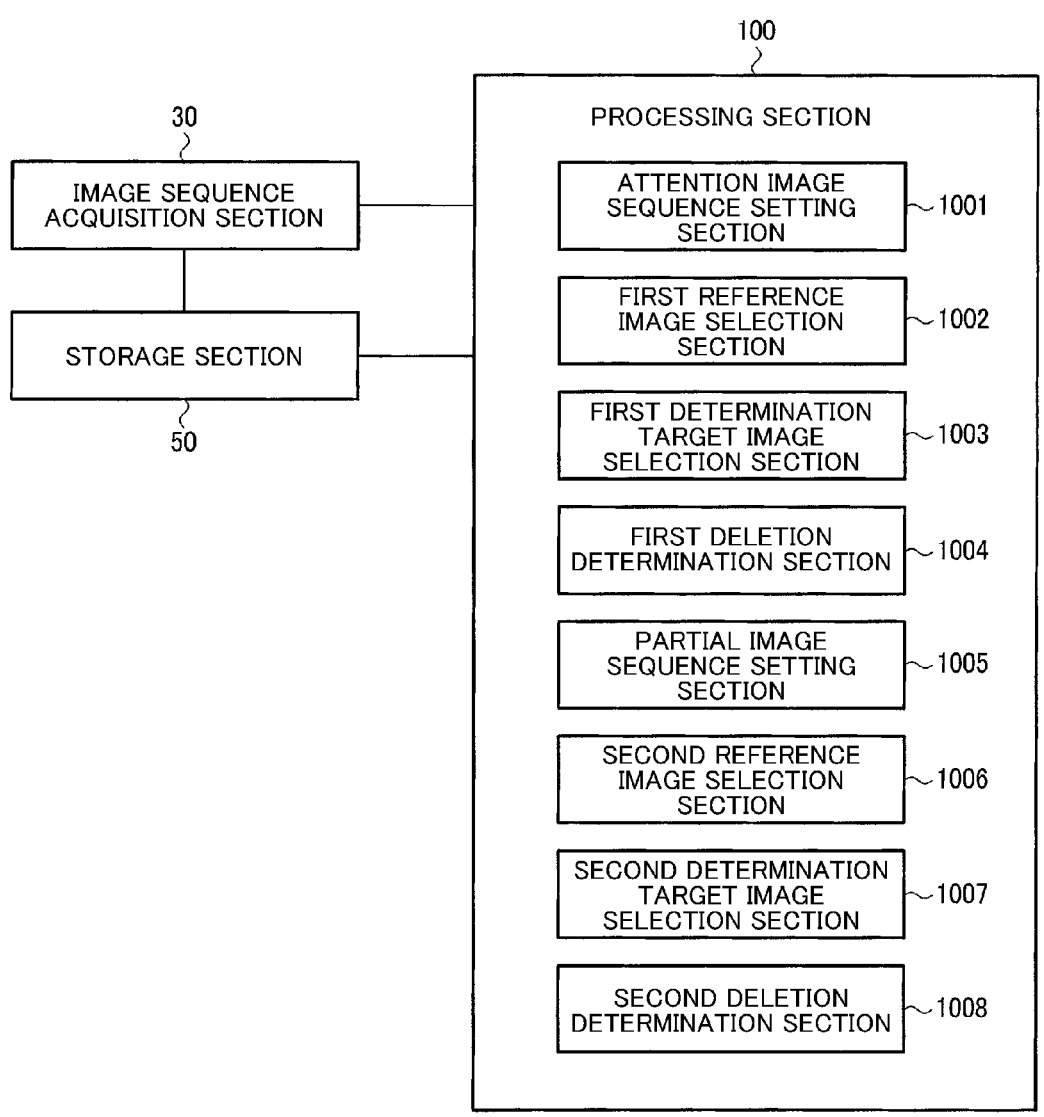
FIG. 17 illustrates a configuration example of an image processing device according to a fifth embodiment.

FIG. 17 illustrates a system configuration example of an image processing device according to the fifth embodiment. The image processing device includes a processing section 100, an image sequence acquisition section 30, and a storage section 50.

The processing section 100 performs an image summarization process that deletes some of a plurality of images included in an image sequence acquired by the image sequence acquisition section 30. The function of the processing section 100 may be implemented by hardware such as a processor (e.g., CPU) or an ASIC (e.g., gate array), a program, or the like.

The image sequence acquisition section 30 acquires the image sequence that is subjected to the image summarization process. The image sequence acquired by the image sequence acquisition section 30 may include RGB channel images that are arranged in time series. Alternatively, the image sequence acquired by the image sequence acquisition section 30 may be a spatially consecutive image sequence (e.g., an image sequence that includes spatially arranged images that have been captured using imaging devices arranged in a row). Note that the images included in the image sequence are not limited to RGB channel images. Another color space (e.g., gray channel image) may also be used.

The storage section 50 stores the image sequence acquired by the image sequence acquisition section 30, and serves as a work area for the processing section 100 and the like. The function of the storage section 50 may be implemented by a memory (e.g., RAM), a hard disk drive (HDD), or the like.

As illustrated in FIG. 17, the processing section 100 may include an attention image sequence setting section 1001, a first reference image selection section 1002, a first determination target image selection section 1003, a first deletion determination section 1004, a partial image sequence setting section 1005, a second reference image selection section 1006, a second determination target image selection section 1007, and a second deletion determination section 1008. Note that the configuration of the processing section 100 is not limited to the configuration illustrated in FIG. 17. Various modifications may be made, such as omitting some of the elements illustrated in FIG. 17, or adding other elements. Note that each section illustrated in FIG. 17 is provided to describe each subroutine when the image summarization process performed by the processing section 100 is divided into a plurality of subroutines. The processing section 100 does not necessarily include each section illustrated in FIG. 17 as an element.

The attention image sequence setting section 1001 extracts an attention image from a plurality of images included in the image sequence (hereinafter may be referred to as "acquired image sequence" in order to clearly distinguish the image sequence from the attention image sequence, the summary image sequence, and the like) acquired by the image sequence acquisition section 30, and sets an attention image sequence that includes one extracted attention image or a plurality of extracted attention images. The term "attention image" used herein refers to an image in which an attention area (e.g., lesion) is captured. The processing section 100 may detect the attention area. For example, the processing section 100 may perform given image processing on each image of the acquired image sequence to determine whether or not the attention area has been captured, and determine the image in which the attention area is captured to be the attention image. The attention area may be detected in various ways. For example, the attention area may be detected by extracting an edge component from the image, or determining the color or the like from the pixel value.

Note that the attention area need not necessarily be detected by the image processing device. For example, the image sequence acquisition section 30 may acquire an image sequence in which metadata is added to each image, the metadata indicating whether or not each image is the attention image. In this case, the attention image sequence setting section 1001 does not perform the attention area detection process, and sets the attention image sequence based on a metadata readout process.

The first reference image selection section 1002 selects a first reference image from the plurality of images included in the attention image sequence. The first determination target image selection section 1003 selects an image among the plurality of images included in the acquired image sequence that differs from the first reference image as a first determination target image. Note that the first determination target image selection section 1003 selects the first determination target image from images among the plurality of images included in the acquired image sequence that differ from the attention image.

The first deletion determination section 1004 determines whether or not the first determination target image can be deleted based on the selected first reference image and the selected first determination target image. The details thereof are described later.

The partial image sequence setting section 1005 sets a partial image sequence that includes a plurality of images among the plurality of images included in the acquired image sequence based on the result of the first deletion determination process performed by the first deletion determination section 1004. The number of partial image sequences is not limited to one. The partial image sequence setting section 1005 may set a plurality of partial image sequences. The details thereof are described later.

When a plurality of partial image sequences have been set, the process performed by the second reference image selection section 1006, the process performed by the second determination target image selection section 1007, and the process performed by the second deletion determination section 1008 are independently performed on each partial image sequence. Specifically, a second reference image is selected from the plurality of images included in the partial image sequence. The second determination target image selection section 1007 selects an image among the plurality of images included in the partial image sequence that differs from the second reference image as a second determination target image. The second deletion determination section 1008 determines whether or not the second determination target image can be deleted based on the selected second reference image and the selected second determination target image. The details of each process are described later.

6.2 Flow of Process

Figure 18:
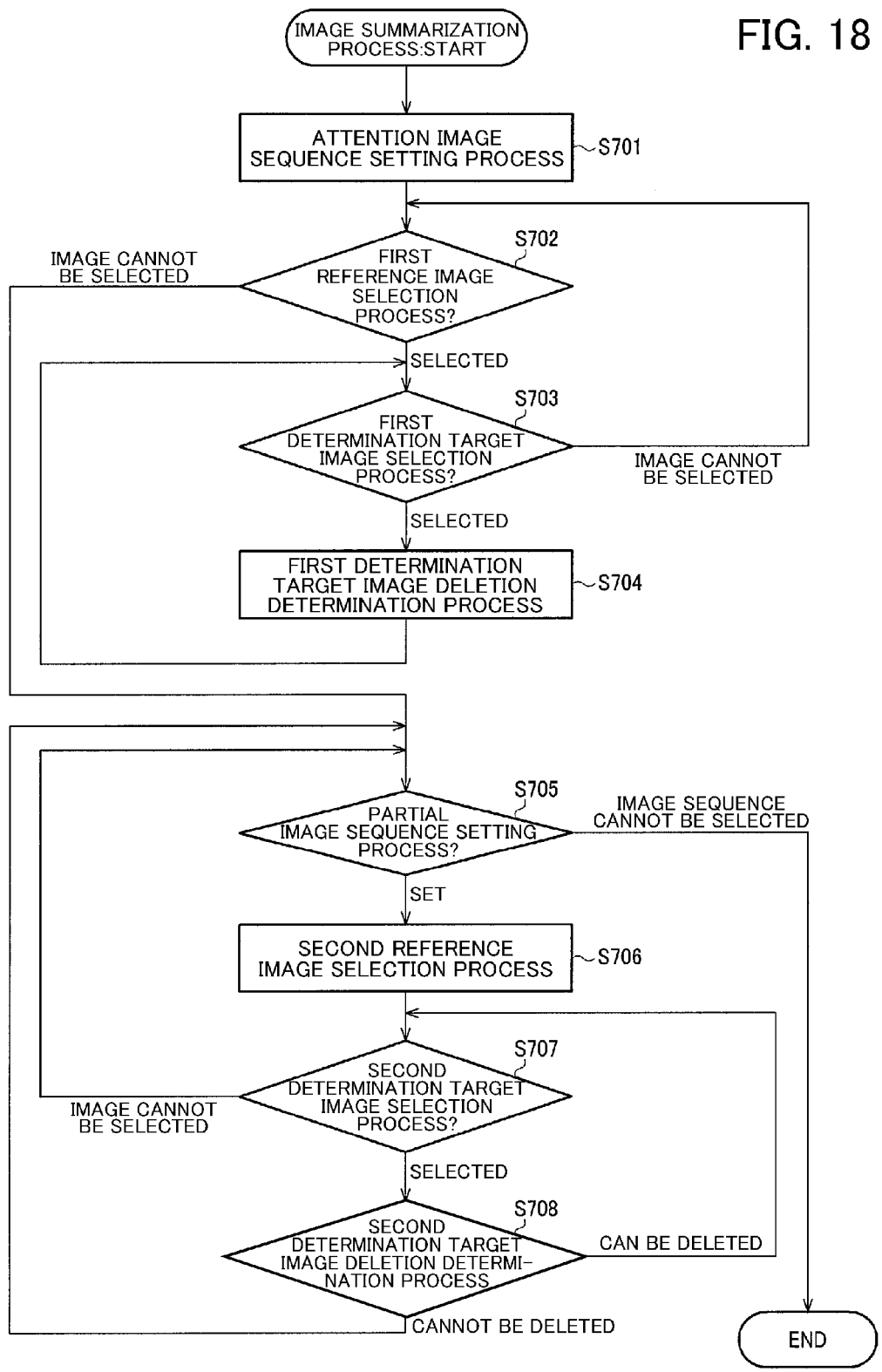
FIG. 18 is a flowchart illustrating an image summarization process according to the fifth embodiment.

FIG. 18 is a flowchart illustrating the image summarization process according to the fifth embodiment. When the image summarization process has started, the attention image is extracted from the plurality of images included in the acquired image sequence to set the attention image sequence (S701). The first reference image is selected from the attention image sequence (S702). When the process in the step S702 is performed for the first time, the first image of the attention image sequence may be selected as the first reference image. In the example illustrated in FIG. 16A, the attention image indicated by J1 is selected as the first reference image. When the process in the step S702 is performed subsequently, the first reference image is updated based on the position of the current first reference image in the attention image sequence. Specifically, the image of the attention image sequence that immediately follows the current first reference image may be selected as the next first reference image. In the example illustrated in FIG. 16A, the image indicated by J2 is selected as the next first reference image when the current first reference image is the image indicated by J1.

When the first reference image has been selected, the first determination target image is selected from the acquired image sequence. When the process in the step S702 is performed for the first time, the first image among the images that are included in the acquired image sequence and are not included in the attention image sequence is selected as the first determination target image. When the process in the step S702 is performed subsequently, the first determination target image is updated based on the position of the current first determination target image in the acquired image sequence. Specifically, the image among the images that are included in the acquired image sequence and are not included in the attention image sequence that immediately follows the current first determination target image may be selected as the next first determination target image.

When the first reference image and the first determination target image have been selected, the first deletion determination process is performed (S704). The first deletion determination process is performed based on the coverage ratio.

The details thereof are described later. After the step S704, information that indicates whether or not the current first determination target image can be deleted is stored, and the step S703 is performed. The images that are included in the acquired image sequence and are not included in the attention image sequence are sequentially selected as the first determination target image, and whether or not each selected image can be deleted is determined by repeating the steps S703 and S704.

When the step S704 has been performed on the last image among the images that are included in the acquired image sequence and are not included in the attention image sequence (i.e., the first determination target image cannot be selected in the step S703), the step S702 is performed again. The first reference image is updated in the step S702. When the first reference image has been updated, whether or not each image (each image other than the images indicated by J1 to J3 in the example illustrated in FIG. 16A) among the images that are included in the acquired image sequence and are not included in the attention image sequence can be deleted is determined using the updated first reference image.

When the last image of the attention image sequence (image indicated by J3 in the example illustrated in FIG. 16A) has been selected as the first reference image, and the process in the step S703 and the process in the step S704 using the first reference image have completed (i.e., the first reference image cannot be selected in the step S702), the first deletion determination process is terminated, and the step S705 is performed.

Whether or not each image that is included in the acquired image sequence and is not included in the attention image sequence can be deleted is determined by the above process. When a plurality of attention images have been detected, whether or not each image can be deleted is determined a plurality of times. Note that it is determined that an image that has been determined to be deleted at least once can be deleted. This is because all of the attention images are allowed to remain in the summary image sequence, and no problem occurs when an image is covered by one of the attention images even if the image is not covered by the remaining attention images.

It is thus determined that an image that has been determined to be deleted is not allowed to remain in the summary image sequence. Note that an image that has been determined to be allowed to remain in the summary image sequence is not necessarily allowed to remain in the summary image sequence, and the second deletion determination process is performed on the image. This is because an image that is not covered by each attention image is determined to be allowed to remain in the summary image sequence, and no problem occurs when an image among the images that have been determined to be allowed to remain in the summary image sequence is deleted provided that the image is covered by a given image.

Figure 16C:
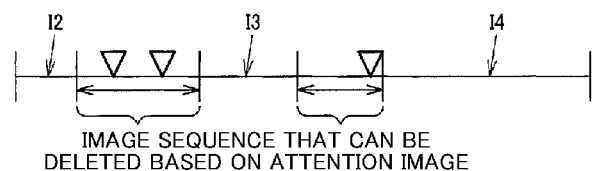

All of the images that have been determined to be allowed to remain in the summary image sequence by the first deletion determination process are not necessarily consecutive images. For example, when a deletion target interval based on the attention image has been determined by the first deletion determination process (see FIG. 16C), the images that cannot be deleted are divided into three sections (see I2 to I4). In this case, it is inefficient to perform the deletion determination process on each image that cannot be deleted. Specifically, since the first section and the second section are situated away from each other in the acquired image sequence, it is likely that the imaging target object changed.

Therefore, it is not likely that it is determined that the image included in the second section can be deleted based on the image included in the first section. Therefore, it is normally unnecessary to perform the process across a plurality of sections, and it suffices to perform the closed process on each section.

Figure 16D:

Therefore, an interval in which the images that have been determined to be allowed to remain in the summary image sequence by the first deletion determination process are situated consecutively in the acquired image sequence is detected, and a partial image sequence that includes the images that correspond to the detected interval is set (S705). In the example illustrated in FIG. 16D, three partial image sequences have been set (see I5 to I7). When only one image has been determined to be allowed to remain in the summary image sequence by the first deletion determination process, the image is not set to be the partial image sequence. Specifically, since the closed process is performed on each partial image sequence, it is impossible to determine whether or not each image included in the partial image sequence can be deleted based on another image when the partial image sequence includes only one image. Therefore, it is determined that one image that has been determined to be allowed to remain in the summary image sequence by the first deletion determination process and is not consecutive with another image is allowed to remain in the summary image sequence.

When the partial image sequence has been set, the first image of the partial image sequence is selected as the second reference image (S706). An image among the images included in the partial image sequence that differs from the second reference image is selected as the second determination target image (S707). When the process in the step S707 is performed for the first time after the second reference image has been set, the image that immediately follows the second reference image (i.e., the second image of the partial image sequence) is selected as the second determination target image. When the process in the step S702 is performed after the step S708, the second determination target image is updated based on the position of the current second determination target image in the partial image sequence. Specifically, the image included in the partial image sequence that immediately follows the current second determination target image may be selected as the next second determination target image.

When the second reference image and the second determination target image have been selected, the second deletion determination process is performed (S708). In the fifth embodiment, the determination process based on the coverage ratio is performed in the same manner as the first deletion determination process. The details thereof are described later.

When it has been determined that the second determination target image can be deleted in the step S708, the second determination target image is updated in the step S707. When the last image of the partial image sequence has been selected as the second determination target image, and it has been determined that the second determination target image cannot be deleted in the step S708 (i.e., all of the images of the partial image sequence other than the second reference image are covered by the second reference image), it is determined that the second reference image is allowed to remain in the summary image sequence, and all of the images of the partial image sequence other than the second reference image are deleted, and the process performed on the partial image sequence is terminated. Specifically, the second determination target image cannot be selected in the step S707, and the step S705 is performed again.

When it has been determined that at least one second determination target image cannot be deleted, the second determination target image must be allowed to remain in the summary image sequence since the second determination target image cannot be covered by the second reference image. Therefore, when it has been determined that the second determination target image cannot be deleted in the step S708, an image sequence that includes the current second determination target image and the subsequent images in the partial image sequence is set to be a new partial image sequence (S705). The processes in the steps S706 to S708 are performed on the new partial image sequence to set the first image of the new partial image sequence (i.e., the second determination target image that has been determined to be allowed to remain in the summary image sequence by the above process) to be the second reference image (i.e., the first image of the new partial image sequence is allowed to remain in the summary image sequence).

In the step S705, one partial image sequence or a plurality of partial image sequences that have been set as a result of the first deletion determination process, and the partial image sequence that has been set as a result of the processes in the steps S706 to S708 performed on the one partial image sequence or the plurality of partial image sequences are sequentially selected. When the process has been performed on all of the partial image sequences (i.e., when the partial image sequence cannot be selected in the step S705), the image summarization process is terminated. In the fifth embodiment, an image that has been set to be the second reference image is allowed to remain in the summary image sequence, and other images are deleted.

FIGS. 19A to 19D illustrate the flow of the process performed on one image sequence among a plurality of partial image sequences that have been set as a result of the first deletion determination process. When an image sequence that includes N images (see FIG. 19A) has been set to be the partial image sequence as a result of the first deletion determination process, the first image is selected as the second reference image, and the second image is selected as the second determination target image. Whether or not the second determination target image can be deleted is then determined.

When it has been determined that the second determination target image cannot be deleted, the next second determination target image is selected. Specifically, the position of the second determination target image is shifted backward, and the third image is selected as the second determination target image (see FIG. 19B). Whether or not the second determination target image can be deleted is then determined, and the image selected as the second determination target image is updated until the second determination target image that is determined to be allowed to remain in the summary image sequence is found.

When it has been determined that the second to (k−1)th images can be deleted (i.e., the second to (k−1)th images are covered by the second reference image to a certain extent), and the kth image cannot be deleted (see FIG. 19C), the second to (k−1)th images are deleted (i.e., the second to (k−1)th images are not allowed to remain in the summary image sequence). Since the kth image is not sufficiently covered by the second reference image, it is necessary to allow the kth image to remain in the summary image sequence. Therefore, the kth image and the subsequent images (kth to Nth images) are set to be a new partial image sequence.

Figure 19A:
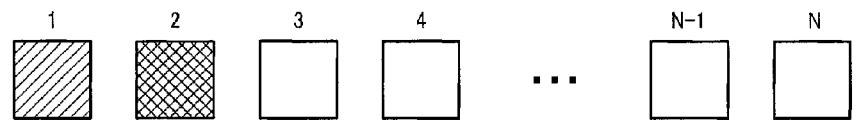
FIGS. 19A to 19D are views illustrating a reference image/determination target image selection method.
Figure 19B:
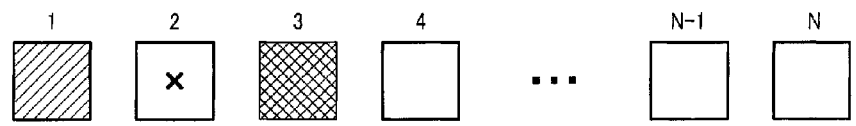
Figure 19C:
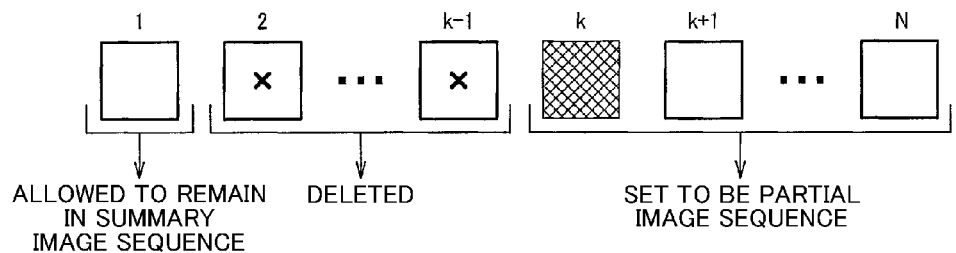
Figure 19D:
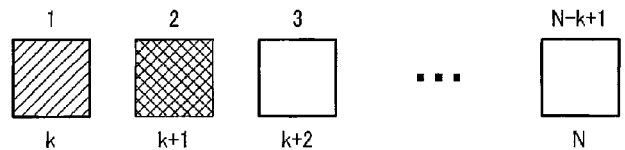

The process illustrated in FIGS. 19A to 19C is then performed on the new partial image sequence. Specifically, the process is performed on the new partial image sequence that includes N−x+1 images (see FIG. 19D) using the first image (i.e., the kth image in FIG. 19C) as the second reference image, and using the second image (i.e., the (k+1)th image in FIG. 19C) as the second determination target image. The subsequent process is performed in the same manner as described above. When it has been determined that the second determination target image can be deleted, the subsequent image is selected as the next second determination target image. When it has been determined that the second determination target image cannot be deleted, the second reference image is allowed to remain in the summary image sequence, the image that can be deleted is deleted, and the images that follow the current second determination target image are set to be a new partial image sequence. The process is terminated when it has been determined that the last image of the partial image sequence can be deleted, or when only one image is included in the partial image sequence (i.e., when the second determination target image cannot be selected).

Although FIG. 18 (flowchart) illustrates an example in which a plurality of partial image sequences that have been set as a result of the first deletion determination process are sequentially processed one by one, the configuration is not limited thereto. When the configuration of the processing section 100 is suitable for parallel processing (e.g., when a CPU that includes a plurality of cores is used as the processing section 100), or when the image processing device according to the fifth embodiment includes a plurality of computers, and distributed processing is performed by each computer, the second deletion determination process may be performed on the plurality of partial image sequences in parallel. This makes it possible to reduce the time required for the second deletion determination process, for example.

6.3 First Deletion Determination Process

Figure 20:
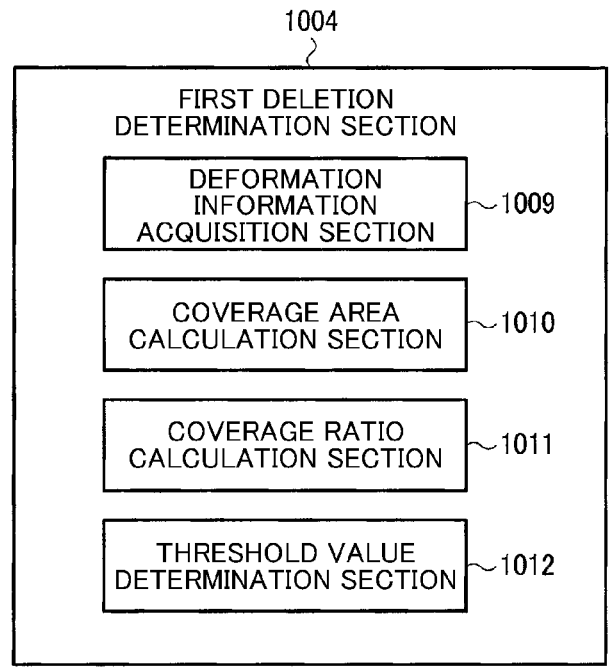
FIG. 20 illustrates a configuration example of a first deletion determination section.

A process that utilizes the coverage ratio is described below as a specific example of the first deletion determination process. As illustrated in FIG. 20, the first deletion determination section 1004 may include a deformation information acquisition section 1009, a coverage area calculation section 1010, a coverage ratio calculation section 1011, and a threshold value determination section 1012. Note that the configuration of the first deletion determination section 1004 is not limited to the configuration illustrated in FIG. 20. Various modifications may be made, such as omitting some of the elements illustrated in FIG. 20, or adding other elements.

The deformation information acquisition section 1009 acquires the deformation information about two images. The details of the deformation information are the same as described above. The deformation information acquisition section 1009 acquires the deformation information about the first reference image selected by the first reference image selection section 1002 and the first determination target image selected by the first determination target image selection section 1003.

The coverage area calculation section 1010 projects one of the two images onto the other image by utilizing the deformation information (deformation parameter) about the two images to calculate the coverage area. The coverage ratio calculation section 1011 calculates the coverage ratio based on the coverage area. The threshold value determination section 1012 compares the calculated coverage ratio with a given threshold value. The details of each process are the same as described above in connection with the first embodiment, and detailed description thereof is omitted.

6.4 Second Deletion Determination Process

Figure 21:
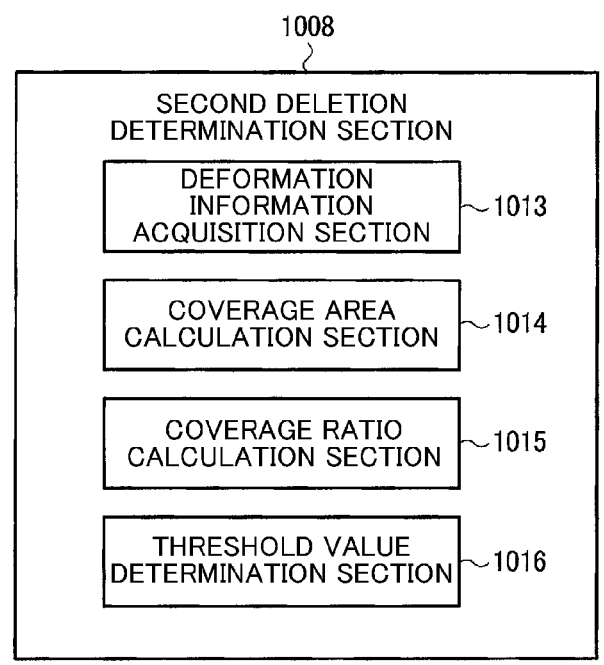
FIG. 21 illustrates a configuration example of a second deletion determination section.

The second deletion determination process is described below. In the fifth embodiment, the second deletion determination process is also performed based on the coverage ratio. As illustrated in FIG. 21, the second deletion determination section 1008 may include a deformation information acquisition section 1013, a coverage area calculation section 1014, a coverage ratio calculation section 1015, and a threshold value determination section 1016. Note that the configuration of the second deletion determination section 1008 is not limited to the configuration illustrated in FIG. 21. Various modifications may be made, such as omitting some of the elements illustrated in FIG. 21, or adding other elements.

The deformation information acquisition section 1013 acquires the deformation information about the second reference image and the second determination target image. The coverage area calculation section 1014 deforms the second reference image based on the deformation information about the second reference image and the second determination target image, and projects the second reference image onto the second determination target image to calculate the coverage area. The coverage ratio calculation section 1015 calculates the coverage ratio from the area ratio of the coverage area to the entire second determination target image, for example. The threshold value determination section 1016 compares the calculated coverage ratio with a given threshold value. Note that the threshold value used for the second deletion determination process may differ from the threshold value used for the first deletion determination process.

In the fifth embodiment, the first deletion determination process and the second deletion determination process are similar processes. Therefore, one deformation information acquisition section may be provided instead of separately providing the deformation information acquisition section 1009 and the deformation information acquisition section 1013. This also applies to the remaining sections. Specifically, the processing section 100 according to the fifth embodiment may include a deformation information acquisition section, a coverage area calculation section, a coverage ratio calculation section, and a threshold value determination section, and the deformation information acquisition section, the coverage area calculation section, the coverage ratio calculation section, and the threshold value determination section may implement both the first deletion determination process and the second deletion determination process.

According to the fifth embodiment, the image processing device includes the image sequence acquisition section 30 that acquires an image sequence that includes a plurality of images, and the processing section 100 that performs the image summarization process that acquires the summary image sequence based on the first deletion determination process and the second deletion determination process that delete some of the plurality of images included in the image sequence acquired by the image sequence acquisition section 30 (see FIG. 17). The processing section 100 sets the attention image sequence that includes one attention image or a plurality of attention images included in the plurality of images. The processing section 100 selects the first reference image from the attention image sequence, selects the first determination target image from the plurality of images, and performs the first deletion determination process that determines whether or not the first determination target image can be deleted based on first deformation information that represents deformation between the first reference image and the first determination target image. The processing section 100 sets the partial image sequence from the image sequence, a plurality of images that have been determined to be allowed to remain by the first deletion determination process being consecutively arranged in the partial image sequence. The processing section 100 selects the second reference image and the second determination target image from the partial image sequence, and performs the second deletion determination process that determines whether or not the second determination target image can be deleted based on second deformation information that represents deformation between the second reference image and the second determination target image.

The attention image is an image that requires attention from the user. The attention image may be an image in which a specific object is captured, or may be an image having a specific color, for example. Whether or not each image is the attention image need not necessarily be determined from the image (e.g., by image processing). For example, sensor information from a sensor provided to the imaging device may be added to each image as metadata, and whether or not each image is the attention image may be determined based on the metadata.

According to this configuration, since the image summarization process can be performed from the viewpoint of whether or not each image is the attention image, and the viewpoint of whether or not the deletion target image is covered by the image that is allowed to remain based on the deformation information about a plurality of images, it is possible to implement an effective image summarization process. Note that the effect of reducing of the number of images is insufficient (see FIG. 16B) when the results of the processes that differ in viewpoint are merely combined. According to the fifth embodiment, an efficient image summarization process can be implemented by utilizing the first deletion determination process that is performed based on the attention image that is allowed to remain, and the second deletion determination process that is performed on the partial image sequence that cannot be deleted based on the attention image. The first determination target image used during the first deletion determination process may be selected from the plurality of images included in the image sequence. Note that the first determination target image may be selected from images among the plurality of images that are not included in the attention image sequence taking account of the processing efficiency.

The processing section 100 may perform at least one of a first coverage ratio determination process and a first structural element determination process as the first deletion determination process. The processing section 100 may perform at least one of a second coverage ratio determination process and a second structural element determination process as the second deletion determination process. The first coverage ratio determination process is a process that calculates the coverage ratio of the first determination target image by the first reference image based on the first deformation information, and determines whether or not the first determination target image can be deleted based on the calculated coverage ratio. The first structural element determination process is a process that determines whether or not the first determination target image can be deleted based on the results of a process that utilizes a structural element that corresponds to the attention area and the first deformation information. The second coverage ratio determination process is a process that calculates the coverage ratio of the second determination target image by the second reference image based on the second deformation information, and determines whether or not the second determination target image can be deleted based on the calculated coverage ratio. The second structural element determination process is a process that determines whether or not the second determination target image can be deleted based on the results of a process that utilizes a structural element that corresponds to the attention area and the second deformation information.

The term "attention area" used herein refers to an area for which the user's observation priority is relatively higher than that of other areas. For example, when the user is a doctor, and desires to perform treatment, the attention area refers to an area in which a mucous membrane area or a lesion area is captured. If the doctor desires to observe bubbles or feces, the attention area refers to an area in which a bubble area or a feces area is captured. Specifically, the attention area for the user differs depending on the objective of observation, but is necessarily an area for which the user's observation priority is relatively higher than that of other areas.

This makes it possible to perform at least one of the process that utilizes the coverage ratio and the process that utilizes the structural element (see the second embodiment) as the process that utilizes the deformation information. When using the coverage ratio, it is possible to ensure that an area of a given image corresponding to a certain ratio (e.g., area ratio) is covered by the summary image that is allowed to remain in the summary image sequence even if the given image is deleted, and prevent a situation in which an area that cannot be observed occurs due to the image summarization process. When using the structural element, it is possible to ensure that at least part of an area captured within a given image having a size corresponding to the structural element is captured within the summary image even if the given image is deleted. Therefore, it is possible to prevent a situation in which an attention area that cannot be observed occurs due to the image summarization process by setting the structural element corresponding to the attention area.

The processing section 100 may detect the attention area from the plurality of images, and set an image among the plurality of images in which the attention area has been detected to be the attention image.

This makes it possible to set the attention image based on the attention area. The attention area is normally similar to the attention area that is used to set the structural element. Note that the attention area may be set to differ from the attention area that is used to set the structural element. For example, an area having a large amount of edge components may be set to be the attention area for the attention image (e.g., folds, a blood vessel structure, and the like are extracted), and a lesion may be set to be the attention area for the structural element (e.g., a situation in which a lesion larger than a given size is prevented).

The image sequence acquisition section 30 may acquire a plurality of in vivo images as the image sequence. The processing section 100 may detect a lesion area from the plurality of in vivo images as the attention area, and set an image among the plurality of in vivo images in which the lesion area has been detected to be the attention image.

According to this configuration, since the process can be performed using the lesion area as the attention area, the process can be used for diagnosis or the like that utilizes an image acquired by a capsule endoscope or the like.

The fifth embodiment may be applied to an endoscope apparatus that includes an imaging section (e.g., an imaging section that is provided in an end section of the endoscope) and the above image processing device.

When a plurality of partial image sequences have been set, the processing section 100 may perform the second deletion determination process on the plurality of partial image sequences in parallel.

According to this configuration, since the second deletion determination process can be implemented by parallel processing, the processing speed can be improved.

Note that part or most of the process performed by the image processing device and the like according to the fifth embodiment may be implemented by a program. In this case, the image processing device and the like according to the fifth embodiment are implemented by causing a processor (e.g., CPU) to execute a program. Specifically, a program stored in an information storage medium is read, and executed by a processor (e.g., CPU). The information storage medium (computer-readable medium) stores a program, data, and the like. The function of the information storage medium may be implemented by an optical disk (e.g., DVD or CD), a hard disk drive (HDD), a memory (e.g., memory card or ROM), or the like. The processor (e.g., CPU) performs various processes according to the first embodiment based on a program (data) stored in the information storage medium. Specifically, a program that causes a computer (i.e., a device including an operation section, a processing section, a storage section, and an output section) to function as each section according to the fifth embodiment (i.e., a program that causes a computer to execute the process implemented by each section) is stored in the information storage medium.

7. Sixth Embodiment

Another method that implements the first deletion determination process and the second deletion determination process is described below. A configuration example of an image processing device according to the sixth embodiment is the same as that illustrated in FIG. 17, and detailed description thereof is omitted. Note that the process performed by the first deletion determination section 1004 and the process performed by the second deletion determination section 1008 differ from those described above. The flow of the process is the same as that illustrated in FIG. 18 (flowchart), and detailed description thereof is omitted. Note that the process in the step S704 and the process in the step S708 differ from those described above.

7.1 Deletion Determination that Utilizes Structural Element

A process that utilizes the structural element that corresponds to an attention area is described below as an example of the first deletion determination process and the second deletion determination process. The attention area may or may not be the same as the attention area used to determine the attention image by the attention image sequence setting section 1001 (see FIG. 17). For example, when the attention image sequence is set using an image in which a lesion is captured as the attention image, the structural element is also set based on the lesion.

When the attention area used to set the attention image sequence is identical with the attention area used during the first deletion determination process, since an image in which the attention area is captured is included in the attention image sequence, and allowed to remain in the summary image sequence, it may be considered that it is meaningless to determine the possibility that the attention area is missed during the first deletion determination process. However, since a large number of images that require the image summarization process are processed, the attention area is normally automatically detected by the system. In this case, it is difficult to detect the attention area with an accuracy of 100%, and an image may occur in which the attention area is captured, but cannot be detected (i.e., cannot be set to be the attention image). Therefore, it is considered that it is effective to make a determination based on the possibility that the attention area is missed in order to prevent a situation in which the attention area captured within such an image is missed, and it is advantageous to use an attention area similar to the attention area used to set the attention image sequence when setting the structural element (see below).

Note that the second deletion determination process is performed in the same manner as the first deletion determination process, and detailed description thereof is omitted.

Figure 22:
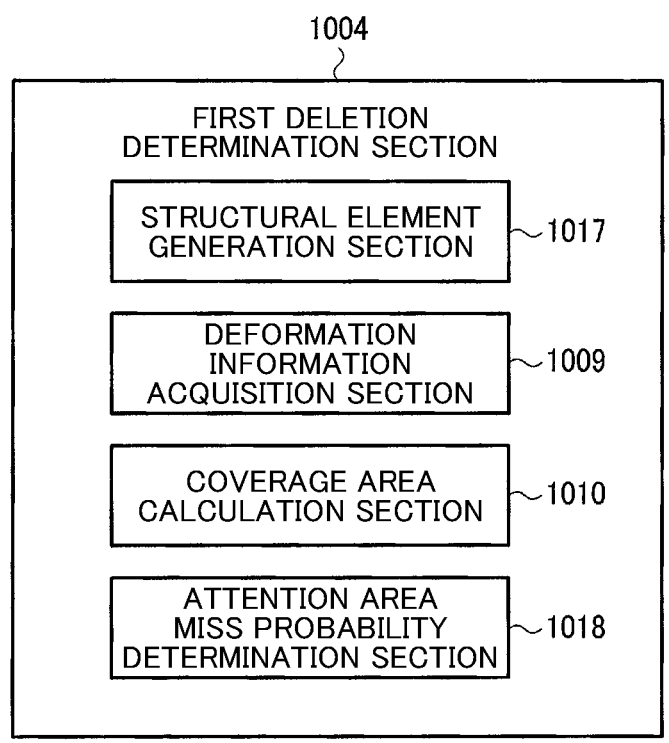
FIG. 22 illustrates another configuration example of a first deletion determination section.

As illustrated in FIG. 22, the first deletion determination section 1004 may include a structural element generation section 1017, a deformation information acquisition section 1009, a coverage area calculation section 1010, and an attention area miss probability determination section 1018. Note that the configuration of the first deletion determination section 1004 is not limited to the configuration illustrated in FIG. 22. Various modifications may be made, such as omitting some of the elements illustrated in FIG. 22, or adding other elements.

The structural element generation section 1017 generates the structural element used for the process performed by the attention area miss probability determination section 1018 based on the attention area. For example, an area having the same shape and the same size as those of the attention area is set to be the structural element. Note that the structural element is not limited thereto.

The coverage area calculation section 1010 may calculate the coverage area, and set an area of the second determination target image other than the coverage area to be a non-coverage area.

The attention area miss probability determination section 1018 determines the probability that the attention area captured within the first determination target image is not observed (captured) within the first reference image (i.e., the attention area is missed) when the first determination target image is deleted.

A specific flow of the process is described below. The structural element generation section 1017 generates the structural element based on the attention area. The structural element generation section 1017 sets an area having a size and a shape that should not be missed to be the structural element taking account of a typical size and the like of the attention area. For example, when the attention area is a lesion, and a lesion that is larger than a circle having a diameter of 30 pixels within the image is severe, and should not be missed, a circle having a diameter of 30 pixels is set to be the structural element.

When the first reference image and the first determination target image have been selected, the deformation information acquisition section 1009 acquires the deformation information about the first reference image and the first determination target image. The coverage area calculation section 1010 projects the first reference image onto the first determination target image by utilizing the acquired deformation information to calculate the coverage area.

When the coverage area has been calculated, the attention area miss probability determination section 1018 determines the probability that the attention area is missed. Specifically, the attention area miss probability determination section 1018 performs a erosion process that utilizes the structural element on the non-coverage area of the first determination target image other than the coverage area to determine whether or not a residual area is present.

A specific example of the erosion process is described below with reference to FIGS. 23A to 23E. As illustrated in FIG. 23A, the non-coverage area is necessarily a closed area, and the boundary of the non-coverage area can be set. For example, an outer boundary BO1 and an inner boundary BO2 are set in FIG. 23A.

The erosion process that utilizes the structural element removes the overlapping area of the non-coverage area and the structural element when a reference point of the structural element is set at the boundary of the non-coverage area. For example, when a circular area is set to be the structural element, and the reference point of the structural element is the center of the circle, the erosion process draws a circle so that the center of the circle is situated at the boundary of the non-coverage area, and excludes the overlapping area of the circle and the non-coverage area from the non-coverage area. Specifically, a circle is drawn around a point situated at the outer boundary BO1 of the non-coverage area (see FIG. 23A), and the overlapping area of the circle and the non-coverage area (i.e., the semicircular area indicated by the diagonal lines in FIG. 23A) is excluded from the non-coverage area.

Since the outer boundary BO1 is processed discretely, and includes a plurality of points, the above process may be performed on each point among the plurality of points. For example, a circle may be sequentially drawn around each point situated at the outer boundary BO1 in a given direction (see FIG. 23A), and the overlapping area of each circle and the non-coverage area may be excluded from the non-coverage area.

When part of the boundary of the non-coverage area coincides with the boundary of the determination target image, for example, the non-coverage area may have only a single boundary. In such a case, the above process may be performed on the single boundary. When the non-coverage area has the outer boundary BO1 and the inner boundary BO2 (see FIG. 23A), the above process is performed on the outer boundary BO1 and the inner boundary BO2. Specifically, a circle is drawn around each point situated at the inner boundary BO2 (see FIG. 23B), and the overlapping area of each circle and the non-coverage area is excluded from the non-coverage area.

The non-coverage area is reduced through the erosion process. For example, the left part of the non-coverage area illustrated in FIG. 23A is completely deleted (i.e., no residual area is present) by the erosion process performed on the outer boundary BO1 (see FIG. 23A) and the erosion process performed on the inner boundary BO2 (see FIG. 23B). On the other hand, a residual area RE that is not excluded by the erosion process performed on the outer boundary BO1 and the erosion process performed on the inner boundary BO2 occurs in the lower right part of the non-coverage area (see FIG. 23C). Specifically, only the residual area RE remains as a result of performing the erosion process that utilizes the structural element over the entire non-coverage area (see FIG. 23D).

The meaning of the erosion process when using a circle having a radius r as the structural element is discussed below. The non-coverage area (i.e., closed area) is considered to be an area that is surrounded by a boundary (different boundaries (e.g., BO1 and BO2) or a single boundary). When the erosion process is performed on the boundary, a point among the points included in the non-coverage area that is situated at a distance equal to or shorter than r from each point situated at the boundary is determined to be the deletion target. Specifically, the distance from the point included in the residual area (that is excluded from the deletion target) to an arbitrary point situated at the boundary is longer than r. Therefore, a circle having a radius r that is drawn around an arbitrary point within the residual area does not intersect each boundary. This means that the entirety of the attention area represented by a circle having a radius R (=r) that is drawn around a point within the residual area is included within the non-coverage area. Note that the above basic idea is also applied even when the structural element has a shape (e.g., quadrangle) other than a circle.

Figure 23C:
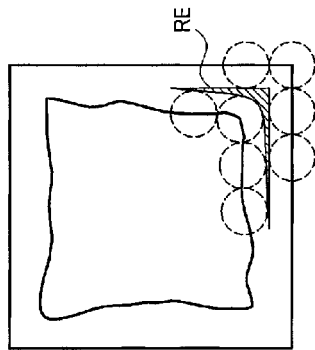
FIGS. 23A to 23E are views illustrating a erosion process that utilizes a structural element and is performed on a non-coverage area.
Figure 23B:
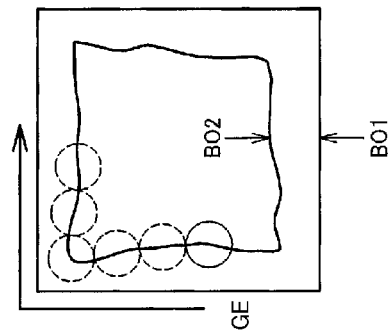
Figure 23E:
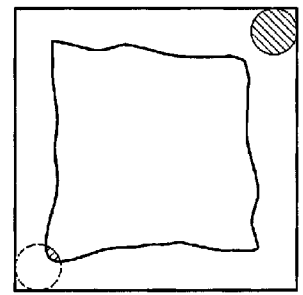
Figure 23A:
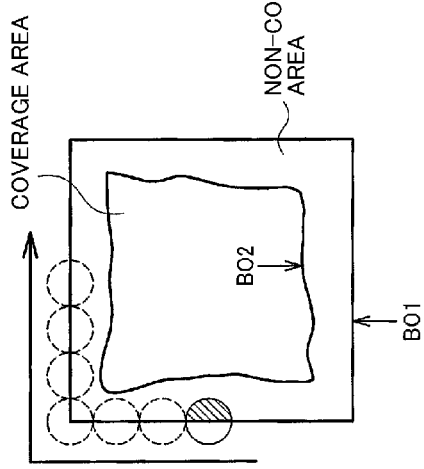
Figure 23D:
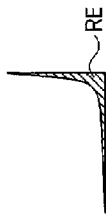

Specifically, when the residual area is present, an area that corresponds to the structural element is included within the non-coverage area (see the lower right part in FIG. 23E). When the attention area (e.g., lesion) is situated at such a position, and the first determination target image is deleted, it is likely that the attention area cannot be observed even if the first reference image is allowed to remain. When the residual area is not present, at least part of the attention area is included within the coverage area (see the upper left part in FIG. 23E). In this case, at least part of the attention area remains in the first reference image even if the first determination target image is deleted. Therefore, the attention area miss probability determination section 1018 performs the erosion process that utilizes the structural element on the non-coverage area, and determines whether or not the first determination target image can be deleted based on whether or not the residual area is present.

7.2 Modification of Deletion Determination

The first deletion determination process and the second deletion determination process may be implemented by the process that utilizes the coverage ratio or the process that utilizes the structural element, as described above. Note that the first deletion determination process and the second deletion determination process need not necessarily be implemented by independently using the process that utilizes the coverage ratio or the process that utilizes the structural element. The process that utilizes the coverage ratio and the process that utilizes the structural element may be used in combination.

For example, the first deletion determination process may be implemented by performing both the process that utilizes the coverage ratio and the process that utilizes the structural element, and the second deletion determination process may also be implemented by performing both the process that utilizes the coverage ratio and the process that utilizes the structural element. In this case, it may be determined that the first determination target image can be deleted when it has been determined that the first determination target image can be deleted by the determination process based on the coverage ratio and the determination process based on the structural element in order to prevent a situation in which an area that cannot be observed occurs, and prevent a situation in which the attention area is missed to improve the utility of the summary image sequence. Note that the threshold value that is compared with the coverage ratio during the first deletion determination process may or may not be identical with the threshold value that is compared with the coverage ratio during the second deletion determination process. The structural element (the size thereof in a narrow sense) used for the first deletion determination process may or may not be identical with the structural element (the size thereof in a narrow sense) used for the second deletion determination process.

The first deletion determination process and the second deletion determination process may be implemented by a different process. For example, the first deletion determination process may be implemented by the process based on the coverage ratio, and the second deletion determination process may be implemented by the process based on the coverage ratio and the process based on the structural element. In this case, since at least one of the first deletion determination process and the second deletion determination process is performed from a plurality of viewpoints (i.e., the coverage ratio and the structural element in the above example), it is expected that the determination accuracy is improved as compared with a process based on a single viewpoint. Moreover, since a process from a given viewpoint (i.e., the structural element in the above example) can be omitted during one of the first deletion determination process and the second deletion determination process, the processing load can be reduced as compared with the case where both the first deletion determination process and the second deletion determination process are performed from a plurality of viewpoints.

When using two viewpoints, it is desirable that at least one of the first deletion determination process and the second deletion determination process be performed based on the two viewpoints. For example, it is desirable to avoid a situation in which the first deletion determination process utilizes the coverage ratio, and the second deletion determination process utilizes the structural element. Specifically, sufficient accuracy may not be achieved depending on the processing target image when only the coverage ratio or the structural element is used. The determination accuracy is improved using both the coverage ratio and the structural element when both the process that utilizes the coverage ratio and the process that utilizes the structural element are performed on a combination of the reference image and the determination target image. However, a combination of the first reference image and the first determination target image during the first deletion determination process does not overlap a combination of the second reference image and the second determination target image during the second deletion determination process, taking account of the above selection method. Specifically, when the first deletion determination process utilizes the coverage ratio, and the second deletion determination process utilizes the structural element, the coverage ratio and the structural element are used independently although the image summarization process utilizes the coverage ratio and the structural element, and the determination accuracy may not be sufficiently improved. In such a case, however, since the processing section 100 must perform a plurality of different deletion determination processes, the system configuration efficiency decreases.

Note that the deletion determination process may be performed from three or more viewpoints using an element other than the coverage ratio and the structural element. In this case, it is desirable that at least one of the first deletion determination process and the second deletion determination process be performed using all of the three or more viewpoints.

According to the sixth embodiment, the processing section 100 may perform a second coverage ratio determination process as the second deletion determination process when performing a first coverage ratio determination process as the first deletion determination process. The processing section 100 may perform a second structural element determination process as the second deletion determination process when performing a first structural element determination process as the first deletion determination process.

This makes it possible to perform a determination process based on the coverage ratio as the first deletion determination process and the second deletion determination process. It is also possible to perform a determination process based on the structural element as the first deletion determination process and the second deletion determination process. In this case, since the first deletion determination process and the second deletion determination process can be implemented from a single viewpoint, the processing load can be reduced as compared with the case of using both the coverage ratio and the structural element.

The processing section 100 may perform both the first coverage ratio determination process and the first structural element determination process as the first deletion determination process. The processing section 100 may perform both the second coverage ratio determination process and the second structural element determination process as the second deletion determination process.

According to this configuration, since at least one of the first deletion determination process and the second deletion determination process is implemented by both the coverage ratio determination process and the structural element determination process, the determination accuracy can be improved as compared with the case where both the first deletion determination process and the second deletion determination process are implemented by the coverage ratio determination process, or both the first deletion determination process and the second deletion determination process are implemented by the structural element determination process. Note that both the coverage ratio determination process and the structural element determination process may be performed during both the first deletion determination process and the second deletion determination process. However, the processing load can be reduced by simplifying (e.g., omitting the structural element determination process) one of the first deletion determination process and the second deletion determination process.

The first coverage ratio determination process may be a determination process based on the result of a comparison between a value that represents the coverage ratio of the first determination target image by the first reference image and a first coverage ratio threshold value. The first structural element determination process may be a process that sets an element having a first size to be the structural element, and performs the erosion process that utilizes the set structural element, or determines whether or not the set structural element is included in an area in which the first determination target image is not covered by the first reference image.

The second coverage ratio determination process may be a determination process based on the result of a comparison between a value that represents the coverage ratio of the second determination target image by the second reference image and a second coverage ratio threshold value. The second structural element determination process may be a process that sets an element having a second size to be the structural element, and performs the erosion process that utilizes the set structural element, or determines whether or not the set structural element is included in an area in which the second determination target image is not covered by the second reference image.

This makes it possible to perform a process that compares the calculated coverage ratio and the threshold value as the determination process based on the coverage ratio. When the coverage ratio is calculated as illustrated in FIG. 2, it suffices that the determination process compare the calculated coverage ratio with the threshold value. Therefore, the process is easy. It is also possible to perform the erosion process that utilizes the structural element (see FIGS. 23A to 23E) as the determination process based on the structural element. Note that the target of the erosion process that utilizes the structural element is not limited to the non-coverage area.

Figure 24A:
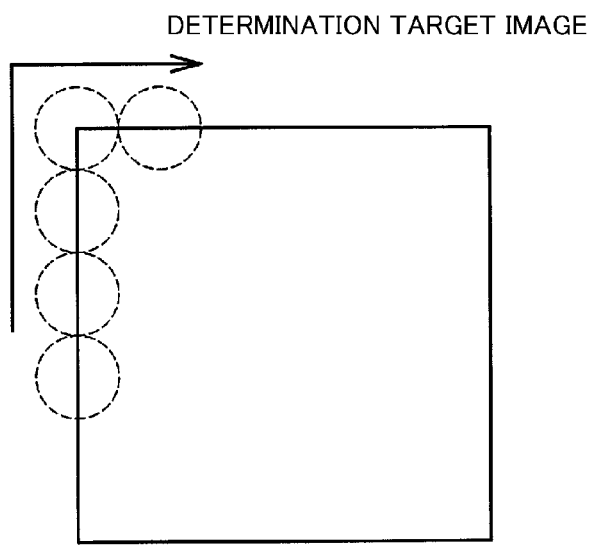
FIGS. 24A and 24B are views illustrating a erosion process that utilizes a structural element and is performed on a determination target image.
Figure 24B:
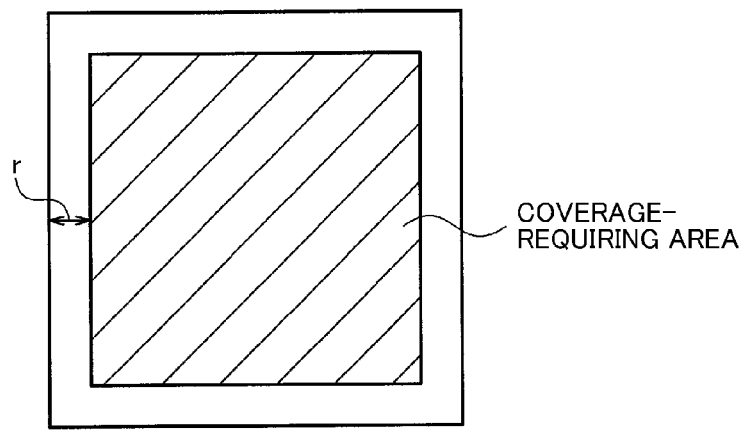
Figure 25A:
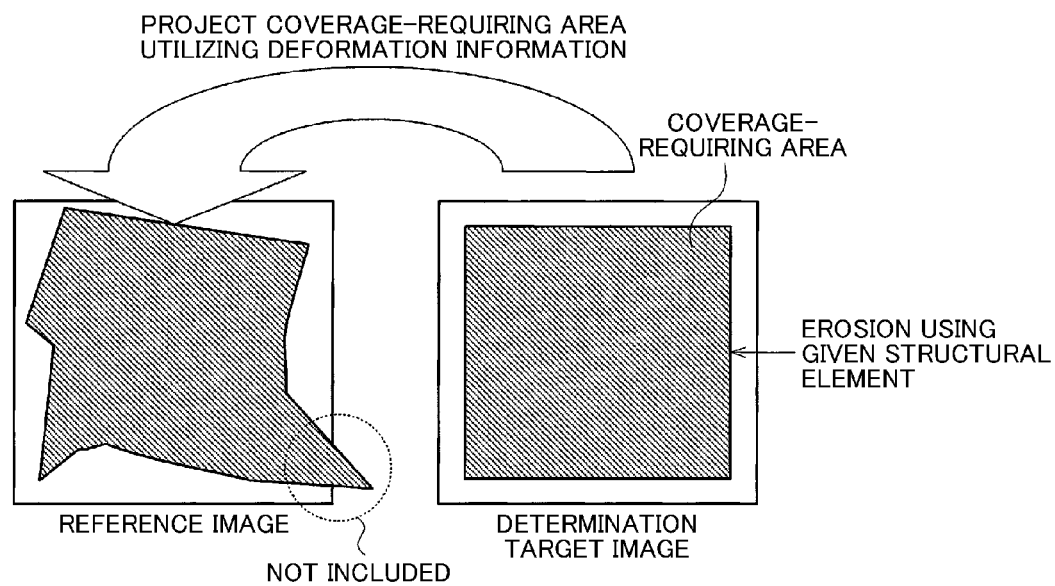
FIGS. 25A and 25B are views illustrating an inclusion determination process on a reference image and a coverage-requiring area.
Figure 25B:
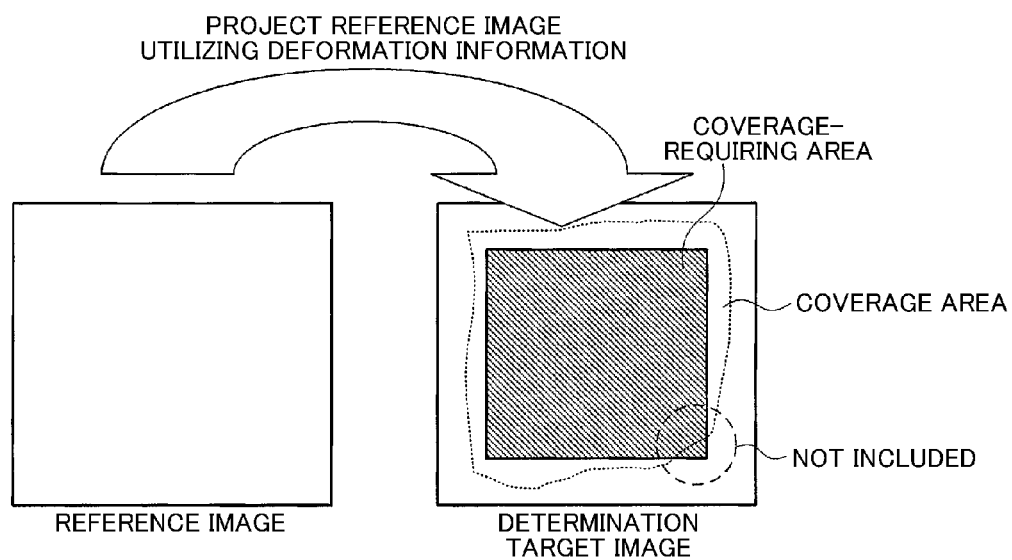

For example, the erosion process that utilizes the structural element may be performed on the determination target image (see FIG. 24A). In this case, the coverage-requiring area that must be covered by the reference image remains by setting the structural element so that the entirety of the attention area is not included within the area that is removed by the erosion process (e.g., setting an element having a size twice that of the attention area as the structural element). Specifically, whether or not the determination target image can be deleted may be determined based on whether or not the entirety of the coverage-requiring area is covered by the reference image. More specifically, one of the reference image and the coverage-requiring area may be deformed using the deformation information, and the inclusion determination process may be performed using the deformed area (see FIGS. 25A and 25B). The determination target image can be deleted when the coverage-requiring area is included in the reference image, and cannot be deleted when the entirety of the coverage-requiring area is not included in the reference image.

Figure 26A:
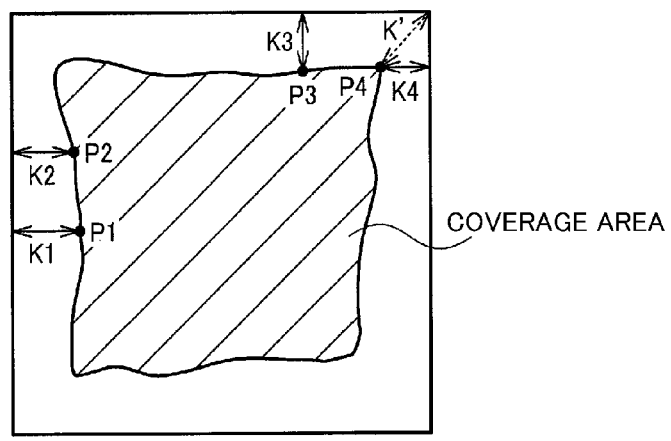
FIGS. 26A and 26B are views illustrating another process that utilizes a structural element.
Figure 26B:
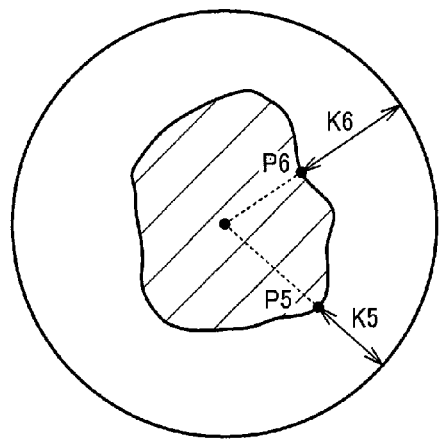

The deletion determination process that utilizes the structural element is not limited to the deletion determination process that utilizes the erosion process. It suffices that the deletion determination process that utilizes the structural element determine whether or not the structural element is included in the non-coverage area. For example, the deletion determination process that utilizes the structural element may be implemented using a simple method that calculates a value that corresponds to the maximum size (diameter) of the non-coverage area based on the distance (e.g., k1 to k6) from the point (e.g., p1 to p6) at the boundary of the coverage area to the boundary of the determination target image, or the distance from the point at the boundary of the determination target image to the boundary of the coverage area, and compares the calculated value with the minimum size of the structural element (e.g., a structural element having the size as that of the attention area) (see FIGS. 26A and 26B).

The processing section 100 may set a value that differs from the first coverage ratio threshold value to be the second coverage ratio threshold value. The processing section 100 may set a size that differs from the first size to be the second size.

This makes it possible to change the determination reference value corresponding to the first deletion determination process and the second deletion determination process even when a process from a single viewpoint is used, and implement a flexible two-step determination process.

8. Seventh Embodiment

The fifth embodiment has been described above taking the method illustrated in FIGS. 19A to 19D as an example of the method that selects the second reference image and the second determination target image during the second deletion determination process. Note that the method that selects the second reference image and the second determination target image is not limited to the method illustrated in FIGS. 19A to 19D. The seventh embodiment illustrates a method that sets two images (forward reference image and backward reference image) to be the second reference image, and sets an image between the two second reference images to be the second determination target image.

In this case, the coverage area may be an area that corresponds to the sum-set of an area calculated by deforming the forward reference image based on the deformation information about the forward reference image and the second determination target image, and an area calculated by deforming the backward reference image based on the deformation information about the backward reference image and the second determination target image (see FIG. 2). Specifically, no problem occurs even if the second determination target image is deleted when the second determination target image is covered by at least one of the forward reference image and the backward reference image. The process performed after calculating the coverage area is the same as described above irrespective of whether the coverage ratio or the structural element is used.

When it has been determined that all of the images situated between the forward reference image and the backward reference images can be deleted, all of the images situated between the forward reference image and the backward reference images may be deleted as long as the forward reference image and the backward reference image are allowed to remain in the summary image sequence. However, it is desirable to set the forward reference image and the backward reference image at positions situated away from each other as much as possible while the condition whereby all of the images situated between the forward reference image and the backward reference images can be deleted is satisfied, in order to improve the effect of reducing the number of images through the image summarization process. Therefore, an optimum position is searched while fixing the forward reference image, and changing the position of the backward reference image. Specifically, the method illustrated in FIGS. 3A and 3B is used The expression "the qth image is OK" is used when the qth image has been selected as the backward reference image, and it has been determined by the deletion determination process that all of the images situated between the forward reference image and backward reference image can be deleted, and the expression "the qth image is NG" is used when the qth image has been selected as the backward reference image, and it has been determined by the deletion determination process that at least one of the images situated between the forward reference image and backward reference image cannot be deleted, for convenience of description.

When the first to Nth images have been input as the partial image sequence, the first image has been selected as the forward reference image, and the qth image has been selected as the backward reference image to search an optimum position of the backward reference image, the second to (q−1)th images are sequentially selected as the second determination target image, and whether the qth image is OK or NG is determined. When the qth image is OK (i.e., when the interval between the forward reference image and the backward reference image can be increased), the next backward reference image is selected from the (q+1)th image and the subsequent images. When the qth image is NG (i.e., when the interval between the forward reference image and the backward reference image is too large), the image that precedes the qth image is basically selected as the next backward reference image.

Specifically, the next summary image that follows the forward reference image is searched by updating the backward reference image with the subsequent image when the qth image is OK, and updating the backward reference image with the preceding image when the qth image is NG, until the end condition is satisfied. The number of images selected as the backward reference image until the next summary image is found can be reduced while reducing the amount of calculations by appropriately updating the position of the next backward reference image. The method according to the seventh embodiment is described in detail below.

Figure 27:
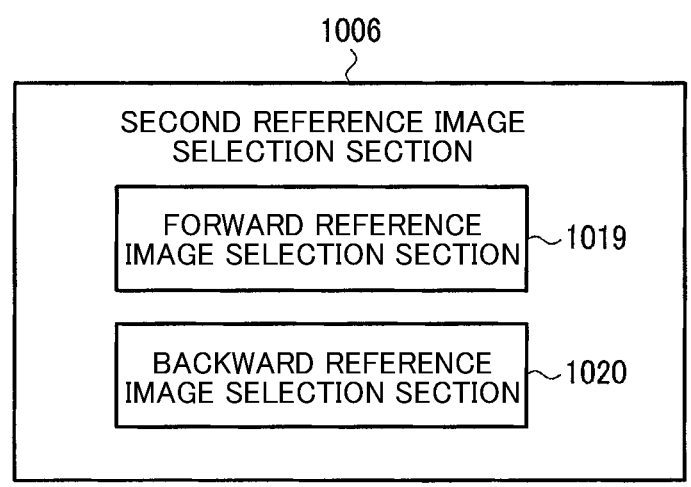
FIG. 27 illustrates a configuration example of a second reference image selection section.

In the seventh embodiment, the second reference image selection section 1006 includes a forward reference image selection section 1019 and a backward reference image selection section 1020 (see FIG. 27). The forward reference image selection section 1019 selects the forward reference image, and the backward reference image selection section 1020 selects the backward reference image.

For example, the first image of the partial image sequence is selected as the forward reference image. When the partial image sequence is a partial image sequence acquired by the first deletion determination process (i.e., when the forward reference image selection process is performed for the first time), an image other than the first image may be selected as the forward reference image. Note that the following description is given on the assumption that the forward reference image is the first image of the partial image sequence unless otherwise specified.

The backward reference image is then selected. For example, a backward reference image selection interval is set that corresponds to the images from which the backward reference image is selected (corresponding to the range in which the next summary image that follows the forward reference image is searched). A semi-open interval [i, j) corresponding to the ith to jth images is set to be the backward reference image selection interval. i corresponds to the image that immediately follows the forward reference image (i=2 in a narrow sense), and j is set to N+2. j is set to N+2 since a virtual (N+1)th image can be set to be the backward reference image. When the backward reference image is the (N+1)th image, all of the subsequent images can be covered by the forward reference image, and whether or not the backward reference image is unnecessary is determined.

The backward reference image is selected from the backward reference image selection interval. The backward reference image is determined based on a given condition in order to efficiently perform the process. Specifically, when the backward reference image is selected for the first time after the forward reference image has been set, the (i+1)th image (third image in a narrow sense) is selected as the backward reference image.

Figure 28A:
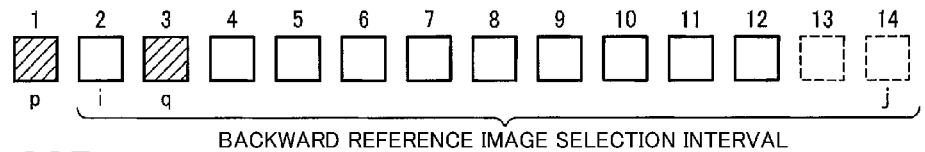
FIGS. 28A to 28G are views illustrating a backward reference image update method.

FIG. 28A illustrates the process described above. FIG. 28A illustrates an image sequence in which N=12. The forward reference image is the first image, the backward reference image selection interval corresponds to the second to fourteenth images (i=2, j=14), and the backward reference image is the third image.

After the backward reference image has been selected, the second determination target image selection process, the coverage ratio calculation process, and the deletion determination process are performed (repeated) in the same manner as described above (detailed description thereof is omitted). In the example illustrated in FIG. 28A, it suffices to select the second image as the second determination target image.

When a given image (the third image during the first process) has been selected as the backward reference image, and the given image is OK (i.e., the position of the backward reference image can be further shifted away from the forward reference image), the image that follows the current backward reference image is selected as the next backward reference image.

Figure 28B:
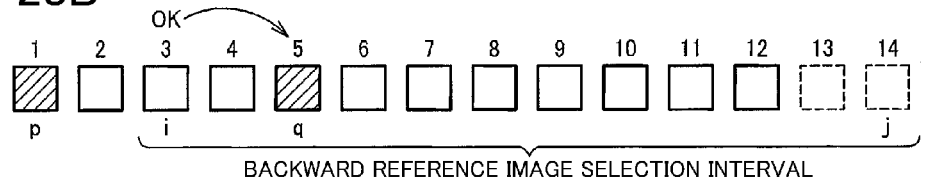

For example, when the current backward reference image is the ath image from the forward reference image, the (2×a)th image from the forward reference image may be selected as the next backward reference image. Specifically, when the third image (i.e., the second image from the forward reference image) has been selected as the backward reference image, and the third image is OK, the fifth image (i.e., the fourth image from the forward reference image) is selected as the next backward reference image (see FIG. 28B).

When the qth image is OK, it is unnecessary to select the (q−1)th image and the images that precede the (q−1)th image as the summary image. In this case, the backward reference image selection interval may be updated since no advantage is obtained even if the image that precedes the qth image is selected as the backward reference image. Specifically, the starting point i of the backward reference image selection interval may be set to i=q. Since the backward reference image is selected from the backward reference image selection interval, the image that precedes the current backward reference image is not selected when the starting point i is set to i=q. For example, when the third image is OK (i.e., when the second image is not selected as the summary image), the second image is excluded from the backward reference image selection interval, and the starting point of the backward reference image selection interval is updated with the third image (see FIG. 28B).

Figure 28C:
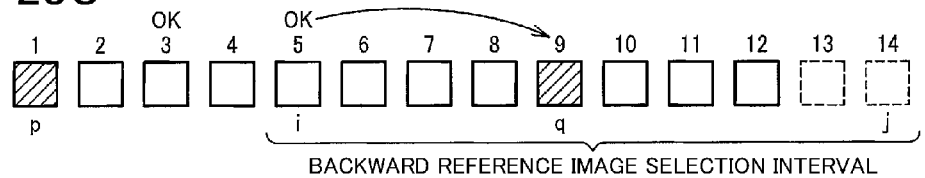

Likewise, when the fifth image is OK (i.e., the second to fourth images are selected as the second determination target image, and the second deletion determination process is performed), the ninth image is selected as the next backward reference image, and the starting point of the backward reference image selection interval is updated with the fifth image (see FIG. 28C).

However, when the qth image has been selected as the backward reference image, and the qth image is OK, it is likely that an image that is situated significantly away from the qth image is selected as the next backward reference image as the value q increases (see FIG. 28C). For example, a situation may occur in which an image that follows the (N+1)th image may be set to be a candidate for the backward reference image (i.e., the backward reference image cannot be selected), or the interval between the current backward reference image and the next backward reference image increases to a large extent, and the next summary image search process becomes inefficient.

Therefore, another method may be used in combination with the above method when selecting an image that follows the current backward reference image as the next backward reference image. For example, the next backward reference image may be determined based on the value (q+j)/2. For example, when the ninth image is OK, the starting point of the backward reference image selection interval is updated with the ninth image (i.e., the backward reference image selection interval is a semi-open interval [9, 14)). Specifically, the center of the search range can be set to be the processing target by selecting an image around the center of the search range as the next backward reference image. The method that halves the search range by determining the center of the search range is a widely known binary search method, and it is known that the binary search method is advantageous from the viewpoint of the amount of calculations. The binary search method can be applied to the backward reference image selection interval since all of the images that precede a given image are determined to be OK when the given image is OK, and all of the images that follow a given image are determined to be NG when the given image is NG. Specifically, it is considered that an efficient process can be implemented by selecting the next backward reference image from approximately the center point between the current backward reference image and the end point of the backward reference image selection interval.

A method that doubles the distance from the forward reference image, and a method that corresponds to the binary search method may be used in combination. For example, when the qth image is the current backward reference image, the kth image that satisfies the following expression (1) may be selected as the next backward reference image. Note that min(a, b) outputs the smaller of a and b.

$$k = \min\left(2q - 1, \frac{q+j}{2}\right) \quad (1)$$

Figure 28D:
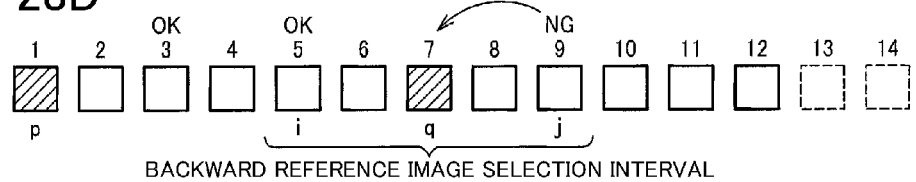

When the qth image is NG the next backward reference image is selected from the images that precede the current backward reference image. The next backward reference image may be determined using various methods. For example, the next backward reference image may be determined using a method that corresponds to the binary search method. In this case, since the starting point of the backward reference image selection interval is the ith image, the next backward reference image is determined based on the value (i+q)/2. Since the qth image is NG, the qth image and the images that follow the qth image are not selected as the summary image. Therefore, the end point of the backward reference image selection interval may be updated (i.e., j=q). FIG. 28D illustrates an example when the ninth image is NG. The seventh image is selected as the next backward reference image, and the end point j of the backward reference image selection interval is updated with j=9.

Note that a semi-open interval is used as the backward reference image selection interval for convenience of explanation. Specifically, since the qth image may be selected as the summary image when the qth image is OK, it is desirable that the starting point i (i=q) of the backward reference image selection interval be included in the backward reference image selection interval. Since the qth image is not selected as the summary image when the qth image is NG, it is desirable that the end point j (j=q) of the backward reference image selection interval not be included in the backward reference image selection interval. Therefore, the backward reference image selection interval is represented by [i, j). The backward reference image selection interval may be represented by an open interval or a closed interval depending on the sign or the expression.

Figure 28E:
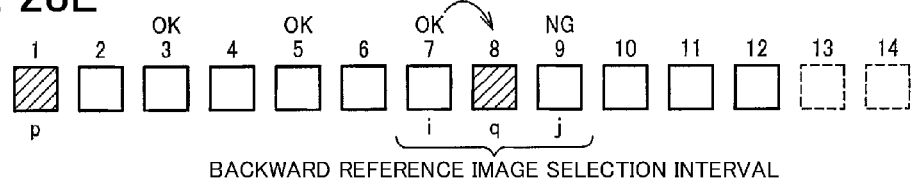
Figure 28F:
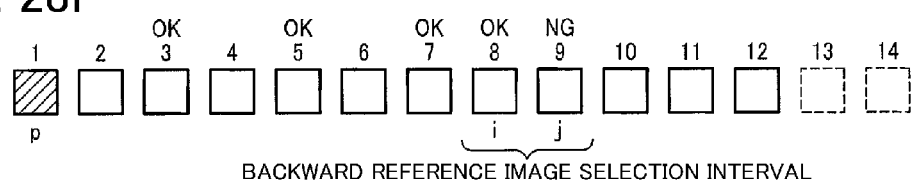
Figure 28G:
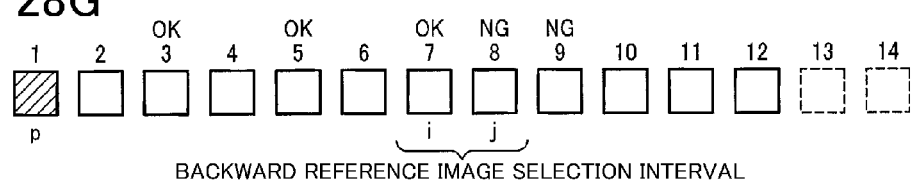

The backward reference image selection interval (i.e., the next summary image search range in a narrow sense) is narrowed by the above process. Since the next summary image is the kth image when the kth image is OK and the (k+1)th image is NG, the process is terminated when an image that is OK and an image that is NG are adjacent to each other. In the above example, it is considered that the process is performed in a binary search manner immediately before the process is terminated (see FIG. 28E). In FIG. 28E, the ith image is OK, the jth image is NG and the qth image between the ith image and the jth image is selected as the backward reference image. FIG. 28F illustrates the case where the qth image is OK, and FIG. 28G illustrates the case where the qth image is NG. In FIGS. 28F and 28G the starting point and the end point of the backward reference image selection interval are adjacent to each other, the image corresponding to the starting point is OK, and the image corresponding to the end point is NG. In this case, the image corresponding to the starting point is selected as the next summary image, and the search process performed on the partial image sequence is terminated.

When the next summary image has been found, an image sequence that includes the next summary image and the images that follow the next summary image is set to be a new partial image sequence. The subsequent process is performed in the same manner as described above, and detailed description thereof is omitted.

Figure 29:
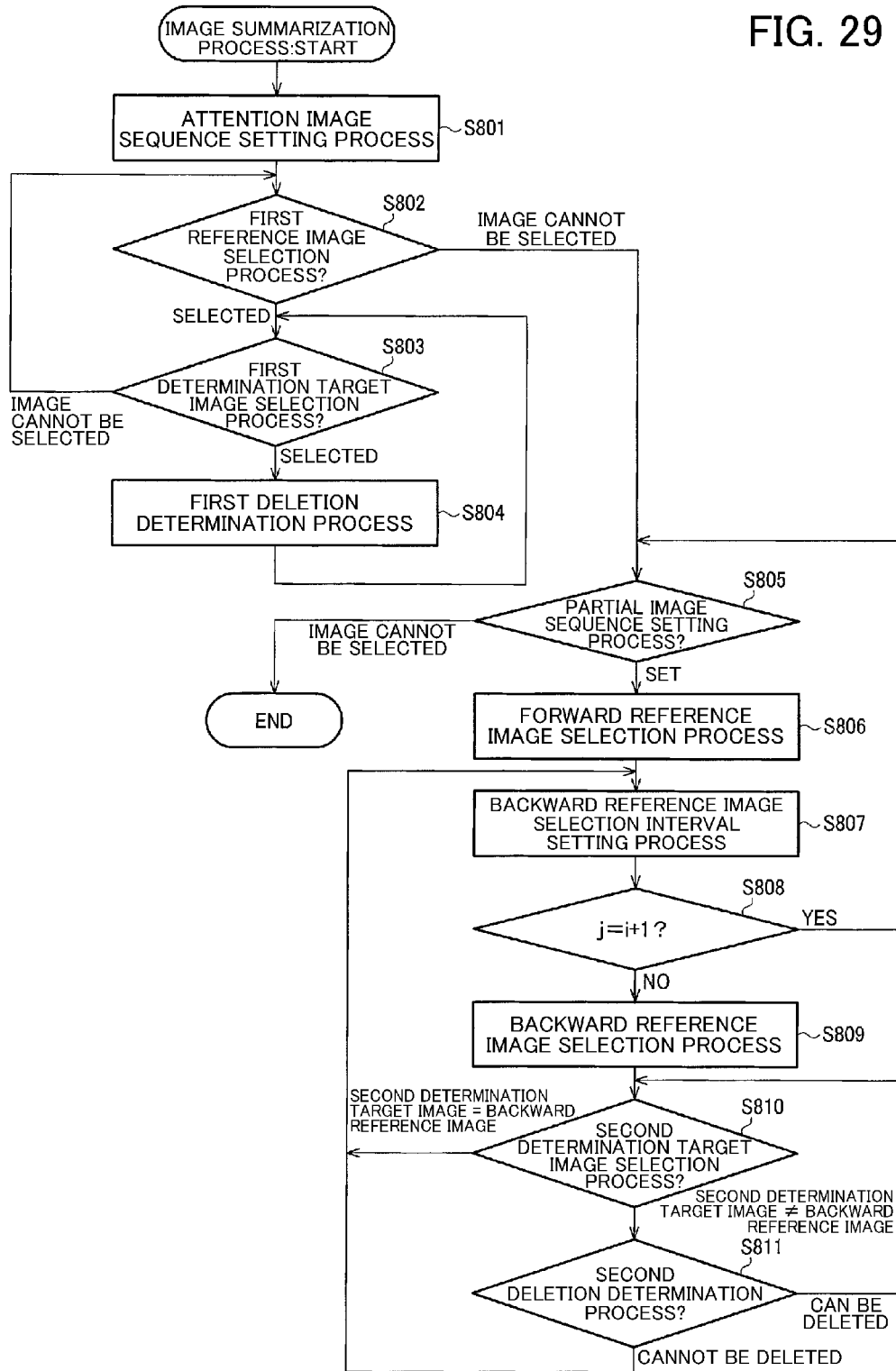
FIG. 29 is a flowchart illustrating an image summarization process according to a seventh embodiment.

FIG. 29 is a flowchart illustrating the image summarization process according to the seventh embodiment. Steps S801 to S805 are performed in the same manner as the steps S701 to S705 illustrated in FIG. 18, respectively, and detailed description thereof is omitted. When the partial image sequence has been set, the first image of the processing target partial image sequence is selected as the forward reference image (S806), and the backward reference image selection interval is set (S807). When the step S807 is performed immediately after the step S806, a semi-open interval [i, j) that satisfies i=2 and j=N+2 may be set, for example. When the step S807 is performed after the step S810 or S811, the backward reference image selection interval is updated.

When the backward reference image selection interval has been set (or updated) in the step S807, whether or not the starting point and the end point of the backward reference image selection interval are adjacent to each other (i.e., whether or not j=i+1 is satisfied) is determined (S808). When it has been determined that the starting point and the end point of the backward reference image selection interval are adjacent to each other in the step S808 (i.e., when it has been determined that the ith image is the next summary image that follows the first image (forward reference image)), the ith image and the subsequent images are set to be the partial image sequence in the step S805.

When it has been determined that the starting point and the end point of the backward reference image selection interval are not adjacent to each other in the step S808 (i.e., when the next summary image has not been found), the backward reference image is selected from the backward reference image selection interval set in the step S807 (S809). When the process in the step S809 is performed for the first time after the forward reference image has been set in the step S806, the (i+1)th image (i.e., the image that follows the forward reference image at an interval of one image) may be selected, for example. When the process in the step S809 is not performed for the first time after the forward reference image has been set in the step S806, the next backward reference image is selected corresponding to the position of the current forward reference image.

After the backward reference image has been selected in the step S809, the second determination target image is selected (S810). When the process in the step S810 is performed for the first time after the backward reference image has been selected in the step S809, the first image (the second image in FIG. 28A) among the images situated between the forward reference image and the backward reference image is selected. The second deletion determination process (e.g., coverage area calculation process, coverage ratio calculation process, and threshold value determination process) after the second determination target image has been selected is performed in the same manner as in the step S708 illustrated in FIG. 18. When it has been determined that the second determination target image can be deleted in the step S811, the second determination target image is updated with the image that immediately follows the current second determination target image (S809), and the process is performed in the same manner as described above. Whether or not all of the images situated between the forward reference image and the backward reference image can be deleted, or at least one of the images situated between the forward reference image and the backward reference image cannot be deleted, is determined by repeating the steps S810 and S811. When it has been determined that all of the images situated between the forward reference image and the backward reference image can be deleted (second determination target image=backward reference image), the step S807 is performed again. When it has been determined that at least one of the images situated between the forward reference image and the backward reference image cannot be deleted, it is determined that the second determination target image cannot be deleted in the step S811, and the step S807 is performed again. It is necessary to store information that represents whether the step S807 is performed after the step S810 or S811, and change the process in the step S807 based on the information (not illustrated in FIG. 29).

When the step S807 is performed after the step S810 (i.e., when all of the images can be deleted), the starting point of the backward reference image selection interval is updated, and the image that follows the current backward reference image is selected as the next backward reference image in the step S807. When the step S807 is performed after the step S811 (i.e., when at least one of the images cannot be deleted), the end point of the backward reference image selection interval is updated, and the image that precedes the current backward reference image is selected as the next backward reference image in the step S807.

According to the seventh embodiment, when the first to Nth (N is an integer equal to or larger than 2) images have been set to be the partial image sequence, the processing section 100 selects the forward reference image and the backward reference image as the second reference image, the forward reference image being the pth (p is an integer that satisfies 1≤p≤N) image, and the backward reference image being the qth (q is an integer equal to or larger than p+2) image. The processing section 100 selects the rth (r is an integer that satisfies p+1≤r≤q−1) image as the second determination target image. The processing section 100 calculates forward deformation information that represents deformation between the forward reference image and the second determination target image, and backward deformation information that represents deformation between the backward reference image and the second determination target image, as the second deformation information, and determines whether or not the second determination target image can be deleted based on the calculated forward deformation information and the calculated backward deformation information.

This makes it possible to set the forward reference image and the backward reference image during the second deletion determination process. The process according to the seventh embodiment that utilizes the deformation information basically aims to ensure that the image that is deleted is covered by the image that is allowed to remain (i.e., the area ratio or the like is high when using the coverage ratio, and at least part of the attention area is observed (captured) when using the structural element). Therefore, no problem occurs when the determination target image is deleted provided that the determination target image cannot be covered by one of a plurality of images that are allowed to remain, but can be covered by combining the plurality of images that are allowed to remain. According to the seventh embodiment, the probability that it is determined that the determination target image can be deleted is increased by utilizing two reference images to improve the effect of reducing the number of images due to the image summarization process.

The processing section 100 may select the backward reference image from the backward reference image selection interval in which the starting point and the end point are set corresponding to the (p+2)th to Nth images, and determine whether or not the second determination target image can be deleted based on the forward reference image and the backward reference image. The processing section 100 may select the xth (x is an integer that satisfies x>q) image included in the backward reference image selection interval as the next backward reference image, and update the starting point of the backward reference image selection interval with the qth image when it has been determined that the (p+1)th to (q−1)th images can be deleted.

The backward reference image selection interval includes the (p+2)th to Nth images that are candidates for the backward reference image. However, since a virtual image (e.g., (N+1)th image) can be selected as the backward reference image, the end point of the backward reference image selection interval may be larger than N. Since the backward reference image selection interval is used as the next summary image (i.e., the next summary image that follows the forward reference image that has been determined to be the summary image) search range, an image that is not selected as the backward reference image, but may be selected as the summary image, may be included in the backward reference image selection interval. In this case, the image ((p+1)th image) that immediately follows the forward reference image may be set to be the starting point of the backward reference image selection interval.

This makes it possible to flexibly determine the position of the next backward reference image when updating the backward reference image. The search range may be narrowed by thoroughly checking the search range from the first image (e.g., by sequentially updating the backward reference image with the image that immediately follows the current backward reference image). Alternatively, the search range may be significantly narrowed by the unit determination that determines whether the qth image is OK or NG by allowing a non-adjacent image to be selected as the next backward reference image. An effective update method may be determined corresponding to the characteristics of the partial image sequence (processing target) and the like. For example, when the correct answer position can be predicted to some extent, the backward reference image may be shifted one by one since it is necessary to mainly search the vicinity of the predicted position. When the correct answer position cannot be predicted, the above binary search or the like may be used taking account of a reduction in the amount of calculations, for example.

When it has been determined that at least one of the (p+1)th to (q−1)th images cannot be deleted, the processing section 100 may select the yth (y is an integer that satisfies y<q) image included in the backward reference image selection interval as the next backward reference image. The processing section 100 may update the end point of the backward reference image selection interval with the qth image.

This makes it possible to select the image that precedes the current backward reference image as the next backward reference image when updating the backward reference image. Since the search process is not limited to a process that selects the adjacent image, the range that precedes the current backward reference image may not have been searched, and may include a correct answer depending on the deletion determination result. In this case, it is possible to perform an appropriate process by performing a forward search process. The next backward reference image need not necessarily be selected from the adjacent image in the same manner as in the case of performing a backward search process.

When the jth (j is an integer) image corresponds to the end point of the backward reference image selection interval, the processing section 100 may set the value x based on the value (q+j)/2. Alternatively, when the ith (i is an integer) image corresponds to the starting point of the backward reference image selection interval, the processing section 100 may set the value y based on the value (i+q)/2.

This makes it possible to use the binary search method when selecting the next backward reference image. The image that is situated between the current backward reference image and the end point is selected when performing a backward search process, and the image that is situated between the current backward reference image and the starting point is selected when performing a forward search process. This makes it possible to halve the search range (corresponding to the length of the backward reference image selection interval). It is expected that the entire search range can be completely searched when log N images are selected as the backward reference image. Therefore, the amount of calculations can be reduced to N×log N. When N is very large, the amount of calculations can be significantly reduced as compared with the method that sequentially shifts the backward reference image in the backward direction (the amount of calculations is $N^2$). Note that the value (q+j)/2 and the value (i+q)/2 are not necessarily an integer, and an image corresponding to each value may be absent. In such a case, the maximum integer that does not exceed the value (q+j)/2, or an integer that is larger than the value (q+j)/2 by 1 may be used, for example.

The processing section 100 may perform a process that allows an image among a plurality of images selected as the forward reference image to remain in the summary image sequence when the starting point and the end point of the backward reference image selection interval are adjacent to each other as a result of updating the starting point or the end point of the backward reference image selection interval. The processing section 100 may set one image among the plurality of images that corresponds to the starting point, and an image that follows the one image among the plurality of images that corresponds to the starting point in the partial image sequence to be a new partial image sequence, and process the new partial image sequence after setting the value p to 1.

The expression "the starting point and the end point of the second reference image selection interval are adjacent to each other" means that the image corresponding to the starting point and the image corresponding to the end point are adjacent to each other in the partial image sequence. When N images have been set to be the partial image sequence, it is considered that the partial image sequence is a set of temporally or spatially continuous images. Therefore, the position within the image sequence can be defined based on the continuity. For example, an image acquired at an earlier time precedes an image acquired at a later time. Specifically, when the images included in the partial image sequence are referred as first to Nth images, it is determined that an image is situated at a forward position when the number assigned to the image is small. Therefore, j=i+1 is satisfied when the ith image and the jth (>i) mage included in the image sequence are adjacent to each other.

This makes it possible to set a condition based on the starting point and the end point of the backward reference image selection interval as a condition whereby the process on the partial image sequence is terminated. An image among the images that are determined to be OK when selected as the backward reference image that is expected to be situated farthest from the forward reference image can be selected as the first image (corresponding to the next summary image) of the partial image sequence by setting the termination condition. This is because the termination condition is equivalent to the condition whereby the position at which the image that is OK and the image that is NG are adjacent to each other is searched (see FIG. 28F, for example). This makes it possible to reduce the number of summary images included in the summary image sequence that is output finally, and reduce the burden imposed on the user, for example.

The first to seventh embodiments according to the invention and the modifications thereof have been described above. Note that the invention is not limited to the first to seventh embodiments and the modifications thereof. Various modifications and variations may be made of first to seventh embodiments according to the invention and the modifications thereof without departing from the scope of the invention. A plurality of elements described in connection with the first to seventh embodiments and the modifications thereof may be appropriately combined to implement various configurations. For example, an arbitrary element may be omitted from the elements described above in connection with the first to seventh embodiments and the modifications thereof. Some of the elements described above in connection with different embodiments and/or modifications may be appropriately combined. Any term cited with a different term having a broader meaning or the same meaning at least once in the specification and the drawings can be replaced by the different term in any place in the specification and the drawings. Specifically, various modifications and applications are possible without materially departing from the novel teachings and advantages of the invention.

What is claimed is:

1. An image processing device comprising:
a first image summarization section that performs a first image summarization process based on a similarity between a plurality of images to acquire a first summary image sequence;
a second image summarization section that performs a second image summarization process based on a target object/scene recognition process on each image among the plurality of images to acquire a second summary image sequence; and
an integration processing section that performs an integration process on the first summary image sequence and the second summary image sequence, or performs an integration process on the first image summarization process and the second image summarization process to acquire an output summary image sequence,
wherein the first image summarization section selects a reference image and a determination target image from the plurality of images, calculates a coverage ratio of the determination target image by the reference image as the similarity based on deformation information about the reference image and the determination target image, and performs the first image summarization process that determines whether or not the determination target image can be deleted based on the coverage ratio.

2. The image processing device as defined in claim 1, wherein:
first to Nth (N is an integer equal to or larger than 2) images are input as an input image sequence,
the first image summarization section selects a pth (p is an integer that satisfies $1 \leq p \leq N$) image as a first reference image, selects a qth (q is an integer equal to or larger than p+2) image as a second reference image, and selects an rth (r is an integer that satisfies $p+1 \leq r \leq q-1$) image as the determination target image, and
the first image summarization section calculates the coverage ratio based on the deformation information about the first reference image and the determination target image and the deformation information about the second reference image and the determination target image, and determines whether or not the determination target image can be deleted based on the coverage ratio.

3. The image processing device as defined in claim 2, wherein the first image summarization section selects a (q+1)th image as the second reference image when it has been determined that (p+1)th to (q−1)th images can be deleted.

4. The image processing device as defined in claim 3, wherein the first image summarization section allows the image selected as the first reference image to remain in the first summary image sequence when it has been determined that at least one image among the (p+1)th to (q−1)th images cannot be deleted, selects the (q−1)th image as a next first reference image, and performs the process again.

5. The image processing device as defined in claim 1, wherein the first image summarization section calculates a coverage area based on the deformation information about the reference image and the determination target image, and calculates a ratio of the coverage area to the determination target image as the coverage ratio, the coverage area being an area in which the determination target image is covered by the reference image.

6. The image processing device as defined in claim 1, wherein the second image summarization section sets consecutive images among the plurality of images that include an identical target object, or consecutive images among the plurality of images that have been recognized to be an identical scene, to be a consecutive image sequence from which a summary image is extracted, based on the recognition process, and performs the second image summarization process that extracts at least one image from the consecutive image sequence as the summary image.

7. The image processing device as defined in claim 6, wherein the second image summarization section selects the summary image extracted from the consecutive image sequence based on an area of the target object.

8. The image processing device as defined in claim 6, wherein the integration processing section integrates a plurality of the consecutive image sequences that have been set during the second image summarization process into one integrated consecutive image sequence based on the first summary image sequence, and extracts at least one image from the integrated consecutive image sequence as the summary image to update the second summary image sequence.

9. The image processing device as defined in claim 8, wherein the integration processing section performs the integration process on the first summary image sequence and the second summary image sequence by selecting an image that is included in at least one of the first summary image sequence and the updated second summary image sequence as the summary image of the output summary image sequence.

10. The image processing device as defined in claim 1, wherein the integration processing section performs the integration process on the first summary image sequence and the second summary image sequence by selecting an image that is included in at least one of the first summary image sequence and the second summary image sequence as a summary image of the output summary image sequence.

11. The image processing device as defined in claim 1, wherein the integration processing section performs the integration process on the first image summarization process and the second image summarization process by causing the first image summarization section to perform the first image summarization process based on results of the second image summarization process.

12. The image processing device as defined in claim 11, wherein the first image summarization section selects an image included in the second summary image sequence from the plurality of images as a reference image based on the integration process, selects a determination target image from the plurality of images, calculates a coverage ratio of the determination target image by the reference image as the similarity based on deformation information about the reference image and the determination target image, and performs the first image summarization process that determines whether or not the determination target image can be deleted based on the coverage ratio.

13. The image processing device as defined in claim 11, wherein the integration processing section performs a second summary image sequence update process that reduces a number of images included in the second summary image sequence based on the first summary image sequence generated by the first image summarization section via the integration process.

14. The image processing device as defined in claim 13, wherein the integration processing section performs the integration process on the first image summarization process and the second image summarization process by causing the first image summarization section to perform the first image summarization process based on results of the second image summarization process after the second summary image sequence update process.

15. The image processing device as defined in claim 11, wherein the integration processing section acquires the first summary image sequence generated by the first image summarization section as the output summary image sequence via the integration process.

16. The image processing device as defined in claim 1, wherein the first image summarization section detects a scene change based on the similarity between the plurality of images, and performs the first image summarization process.

17. The image processing device as defined in claim 1, wherein:
the plurality of images are a capsule endoscopic image, and
the second image summarization section performs the recognition process on an in vivo attention area captured within the capsule endoscopic image as the target object.

18. The image processing device as defined in claim 17, wherein the second image summarization section performs the recognition process on the in vivo attention area based on a special light image acquired by applying light within a specific wavelength band.

19. A computer-readable storage device having stored thereon, a program that is executable by a computer to cause the computer to function as:
a first image summarization section that performs a first image summarization process based on a similarity between a plurality of images to acquire a first summary image sequence;
a second image summarization section that performs a second image summarization process based on a target object/scene recognition process on each image among the plurality of images to acquire a second summary image sequence; and
an integration processing section that performs an integration process on the first summary image sequence and the second summary image sequence, or performs an integration process on the first image summarization process and the second image summarization process to acquire an output summary image sequence,
wherein the first image summarization section selects a reference image and a determination target image from the plurality of images, calculates a coverage ratio of the determination target image by the reference image as the similarity based on deformation information about the reference image and the determination target image, and performs the first image summarization process that determines whether or not the determination target image can be deleted based on the coverage ratio.

20. An image processing method comprising:
performing a first image summarization process based on a similarity between a plurality of images to acquire a first summary image sequence;
performing a second image summarization process based on a target object/scene recognition process on each image among the plurality of images to acquire a second summary image sequence; and
performing an integration process on the first summary image sequence and the second summary image sequence, or performing an integration process on the first image summarization process and the second image summarization process to acquire an output summary image sequence;
wherein the first image summarization process comprises selecting a reference image and a determination target image from the plurality of images, calculating a coverage ratio of the determination target image by the reference image as the similarity based on deformation information about the reference image and the determination target image, and performing the first image summarization process that determines whether or not the determination target image can be deleted based on the coverage ratio.

* * * * *